United States Patent
Liddament et al.

(10) Patent No.: US 11,111,292 B2
(45) Date of Patent: Sep. 7, 2021

(54) ANTI-IL-5 ANTIBODIES

(71) Applicant: Cephalon, Inc., Frazer, PA (US)

(72) Inventors: Mark Terence Liddament, Haberfield (AU); Anthony Doyle, Macquarie Park (AU); Adam Clarke, Macquarie Park (AU); David Jose Simon Laine, Gladesvilie (AU); Bridget Ann Cooksey, Macquarie Park (AU)

(73) Assignee: CEPHALON, INC., Frazer, PA (US)

( * ) Notice: Subject to any disclaimer, the term of this patent is extended or adjusted under 35 U.S.C. 154(b) by 366 days.

(21) Appl. No.: 15/848,090

(22) Filed: Dec. 20, 2017

(65) Prior Publication Data

US 2018/0186873 A1    Jul. 5, 2018

Related U.S. Application Data

(60) Provisional application No. 62/438,502, filed on Dec. 23, 2016.

(51) Int. Cl.
| | |
|---|---|
| *C07K 16/24* | (2006.01) |
| *A61P 37/08* | (2006.01) |
| *A61K 39/00* | (2006.01) |
| *C07K 14/54* | (2006.01) |

(52) U.S. Cl.
CPC ............ *C07K 16/244* (2013.01); *A61P 37/08* (2018.01); *A61K 2039/505* (2013.01); *C07K 2317/21* (2013.01); *C07K 2317/24* (2013.01); *C07K 2317/33* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/75* (2013.01); *C07K 2317/92* (2013.01)

(58) Field of Classification Search
None
See application file for complete search history.

(56) References Cited

FOREIGN PATENT DOCUMENTS

| | | |
|---|---|---|
| CL | 201800499 | 2/2018 |
| EP | 1749840 | 2/2007 |
| WO | 88/01649 A1 | 3/1988 |
| WO | 92/01047 A1 | 1/1992 |
| WO | 94/13804 A1 | 6/1994 |
| WO | 96/21000 | 7/1996 |
| WO | 98/44001 A1 | 10/1998 |
| WO | 2003/085089 | 10/2003 |
| WO | 2009/085462 A1 | 7/2009 |
| WO | 2017/033121 A1 | 3/2017 |

OTHER PUBLICATIONS

Zhang, Ji et al. "Mapping and characterization of the epitope(s) of Sch 55700, a humanized mAb, that inhibits human IL-5" International Immunology, 1999, 1935-1943.

Wu, et al.; An Analysis of the Sequences of the Variable Regions of Bence Jones Proteins and Myeloma Light Chains and Their Implications for Anti-Body Complementarity; 1970, 132: 211-250.

Ward el al., Binding activities of a repertoire of single immunoglobulin variable domains secreted from *Escherichia coli*; Nature, 1989, 341: 544-546.

Shi et al., De Novo Selection of High-affinity Antibodies from Synthetic Fab libraries Displayed on Phage as pIX Fusion Proteins; J Mol Biol; 2010, 397: 385-396.

Mukherjee, M. et al."Anti-1L5 therapy for asthma and beyond", World Allergy Organization Journal, 2014, 32.

Liddament, M. et al., "P155 Higher binding addinity and in-vitro potency of reslizumab for interleukin-5 compared with mepolizumab", Annals of Allergy, Asthma & Immunology, 2016, abstract.

Lefranc, M. et al., "IMGT unique numbering for immunoglobulin and T cell receptor variable domains and Ig superfamily V-like domains", Developmental & Comparative Immunology, 2003, 27, 55-77.

Knappik, A. et al., "Fully synthetic human combinatorial antibody libraries (HuCAL) based on modular consensus frameworks and CDRs randomized with trinucleotides", J Mol Biol, 2000, 296, 57-86.

Hart, T. K. et al, "Preclinical efficacy and safety of mepolizumab (SB-240563), a humanized monoclonal antibody to IL-5, in cynomolgus monkeys", Journal of Allergy and Clinical Immunology, 2001, 250-257.

Chothia, C. et al., "Canonical structures for the hypervariable regions of immunoglobulins", J Mol Biol, 1987, 196, 901-917.

Almagro, J., "Identification of differences in the specificity-determining residues of antibodies that recognize antigens of different size: implications for the rational design of antibody repertoires" Journal of Molecular Recognition, 2004,17,132-143.

Gil, et al.; Anti-inflammatory actions of Chemoattractant Receptor-homologous molecule expressed on Th2 by the antagonist MK-7246 in a novel rat model of Alternaria alternata elicited pulmonary inflammation, European Journal of Pharmacology 743 (2014) 106-116.

Whitelegg, et al: WAM: an improved algorithm for modelling antibodies on the Web, Protein Engineering, vol. 13, No. 12, 2000, 819-824.

*Primary Examiner* — Gary B Nickol
*Assistant Examiner* — Jegatheesan Seharaseyon
(74) *Attorney, Agent, or Firm* — BakerHostetler

(57) ABSTRACT

Disclosed herein are fully human antibody molecules that immunospecifically bind to human IL-5. The antibody molecules can bind to human IL-5 with an equilibrium affinity constant ($K_D$) of at least about 40 pM as determined by surface plasmon resonance.

24 Claims, 18 Drawing Sheets

Specification includes a Sequence Listing.

```
                              CDR1                                              CDR2
                  24 25 26 27 28 29 30 31 32 33 34                  50 51 52 53 54 55 56
SYVLTQPPSVSVAPGQTARITC  G  G  N  N  I  G  S  K  N  V  Y  WYQQKPGQAPVLVVH  D  D  S  D  R  P  S
                        K  D  H  A  D  K  H  A                         L  S

CDR3
                  89 90 91 92 93 94 95 95A 95B 96 97
GIPERFSGSNSGNTATLTISRVEVGDEADYYC  Q  V  W  D  S  S  D   H   S   V  A  W  FGGGTKLTVLG [3A5.040 VL]
                                     L                  D   Y      W
```

FIG. 5

ANTI-IL-5 ANTIBODIES

CROSS REFERENCE TO RELATED APPLICATIONS

This application claims priority to U.S. Provisional Application No. 62/438,502, filed Dec. 23, 2016, the disclosure of which is hereby incorporated by reference in its entirety.

SEQUENCE LISTING

The instant application contains a sequence listing which has been submitted electronically in ASCII format and is hereby incorporated by reference in its entirety. Said ASCII copy, created on Nov. 30, 2017, is named 102085.000906_sl.txt and is 93,529 bytes in size.

TECHNICAL FIELD

Disclosed herein are novel antibody molecules that immunospecifically bind IL-5, and uses of the disclosed antibodies.

BACKGROUND

Interleukin-5 (IL-5) is a T-helper 2 (Th2) cytokine which causes the proliferation and differentiation of both B cells and eosinophils. In B cells, IL-5 also increases immunoglobulin secretion. IL-5 is a key modulator of eosinophils, where it also regulates maturation, migration to tissues, survival, and the prevention of apoptosis.

Through two separate motifs, IL-5 binds to its specific receptor (IL5-Rα) and a signaling receptor, a common β-chain (βc) shared between Interleukin-3 (IL-3) and granulocyte-macrophage colony stimulating factor (GMCSF). The affinity of IL-5 for IL5-Rα has been reported to be in the mid-low nM range (0.2-100 nM); this shifts into the mid-pM range (~100 pM) in the presence of βc. IL5-Rα binds to IL-5 specifically, which then recruits βc to IL-5R.

The therapeutic potential of targeting interleukin-5 (IL-5) has been demonstrated by extensive validation in the literature and recent positive Phase III clinical data for both reslizumab and mepolizumab.

SUMMARY

Disclosed herein are human antibody molecules that immunospecifically bind to human IL-5 with an equilibrium affinity constant ($K_D$) of at least about 40 pM as determined by surface plasmon resonance.

Also provided are antibody molecules comprising a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NOs: 5, 21, 24, 27, 30, 33, 36, 39, or 66, a light chain CDR2 comprising the amino acid sequence of SEQ ID NOs: 7, 42, or 45, and a light chain CDR3 comprising the amino acid sequence of SEQ ID NOs: 15, 48, 51, 54, 57, 60, or 63.

The disclosed antibody molecules can comprise a heavy chain variable region comprising an amino acid sequence that is at least 90%, 95%, 96%, 97%, 98%, 99%, or 100% identical to the amino acid sequence of SEQ ID NO: 16 and a light chain variable region comprising an amino acid sequence that is at least 90%, 95%, 96%, 97%, 98%, 99%, or 100% identical to the amino acid sequence of SEQ ID NO: 17, 22, 25, 28, 31, 34, 37, 40, 43, 46, 49, 52, 55, 58, 61, 64, or 67, wherein the variability (i.e. the at least 90%, 95%, 96%, 97%, 98%, 99%, or 100% identity) occurs outside of the CDR sequence.

The disclosed antibody molecules can comprise a heavy chain comprising an amino acid sequence that is at least 90%, 95%, 96%, 97%, 98%, 99%, or 100% identical to the amino acid sequence of SEQ ID NOs: 18 or 20 and a light chain comprising an amino acid sequence that is at least 90%, 95%, 96%, 97%, 98%, 99%, or 100% identical to the amino acid sequence of SEQ ID NO: 19, 23, 26, 29, 32, 35, 38, 41, 44, 47, 50, 53, 56, 59, 62, 65, or 68, wherein the variability (i.e. the at least 90%, 95%, 96%, 97%, 98%, 99%, or 100% identity) occurs outside of the CDR sequence.

Nucleic acid molecules encoding the disclosed antibody molecules, vectors comprising the nucleic acid molecules, and cells transformed to express the disclosed antibody molecules are also provided.

Also disclosed are pharmaceutical compositions comprising any of the antibody molecules disclosed herein.

Also provided are methods of treating a subject having eosinophilic asthma, hypereosinophilic syndrome, nasal polyposis with eosinophilic involvement, eosinophilic granulomatosis with polyangiitis, atopic dermatitis or eosinophilic esophagitis comprising administering to the subject a therapeutically effective amount of any of the herein disclosed antibody molecules, or pharmaceutical compositions comprising the same, to treat the eosinophilic asthma, hypereosinophilic syndrome, nasal polyposis with eosinophilic involvement, eosinophilic granulomatosis with polyangiitis, atopic dermatitis or eosinophilic esophagitis.

Use of an effective amount of any of the herein disclosed antibody molecules, or pharmaceutical compositions comprising the same, in the treatment of eosinophilic asthma, hypereosinophilic syndrome, nasal polyposis with eosinophilic involvement, eosinophilic granulomatosis with polyangiitis, atopic dermatitis, or eosinophilic esophagitis are also provided.

Further provided is the use of any of the herein disclosed antibody molecules, or pharmaceutical compositions comprising the same, in the manufacture of a medicament for the treatment of eosinophilic asthma, hypereosinophilic syndrome, nasal polyposis with eosinophilic involvement, eosinophilic granulomatosis with polyangiitis, atopic dermatitis or eosinophilic esophagitis.

BRIEF DESCRIPTION OF THE DRAWINGS

The summary, as well as the following detailed description, is further understood when read in conjunction with the appended drawings. For the purpose of illustrating the disclosed antibody molecules, methods, and uses, there are shown in the drawings exemplary embodiments of the antibody molecules, methods, and uses; however, the antibody molecules, methods, and uses are not limited to the specific embodiments disclosed. In the drawings:

FIG. 5 illustrates exemplary light chain CDR consensus sequences aligned to the 3A5.040 VL sequence (top sequence). 3A5.040 VL CDR single amino acid substitution variants which showed potential improvements according to the inclusion criteria described in the Examples of (the ratio of variant kd to 3A5.040 kd≥1.5) and (the ratio of variant expression level to 3A5.040 expression level ≥0.5) were included in the consensus sequences. CDR definitions and numbering are according to AbM and Kabat nomenclature, respectively. The boxes identify the positions of CDR residues. The various sequences recited in this figure are provided in SEQ ID NO:75.

FIG. 8B top panel: Donor 1, FIG. 8B middle panel: Donor 3; FIG. 8B bottom panel: Donor 4.

FIG. 13B illustrates further details of the blood eosinophil counts for animals treated with 3A5.046 antibody, up to 45 days post-challenge (52 days post-dose). Eosinophil counts remained below baseline for at least 45 days post-challenge following a single dose of 3A5.046 one week before challenge.

DETAILED DESCRIPTION OF ILLUSTRATIVE EMBODIMENTS

Figure 1:
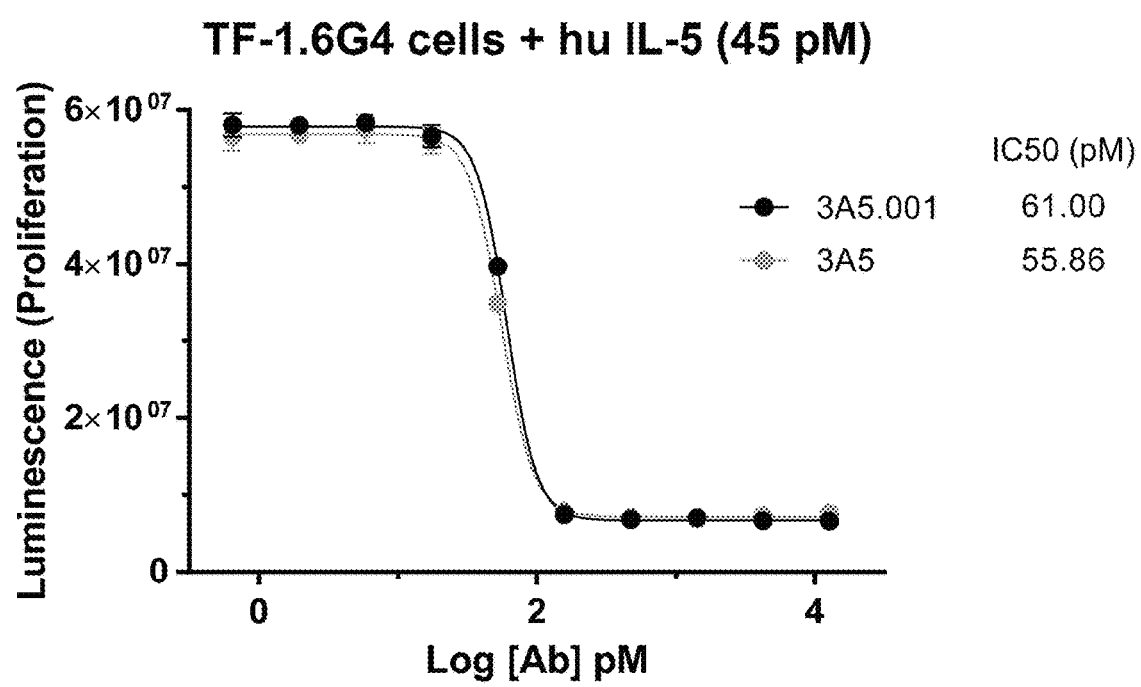
FIG. 1 illustrates a TF-1.6G4 assay showing that antibody variant 3A5.001 (in IgG4 format) retained an equivalent potency to the original antibody 3A5 (in IgG1 format).

The disclosed antibody molecules, methods, and uses may be understood more readily by reference to the following detailed description taken in connection with the accompanying figures, which form a part of this disclosure. It is to be understood that the disclosed antibody molecules, methods, and uses are not limited to the specific antibody molecules, methods, and uses described and/or shown herein, and that the terminology used herein is for the purpose of describing particular embodiments by way of example only and is not intended to be limiting of the claimed antibody molecules, methods, and uses.

Unless specifically stated otherwise, any description as to a possible mechanism or mode of action or reason for improvement is meant to be illustrative only, and the disclosed antibody molecules, methods, and uses are not to be constrained by the correctness or incorrectness of any such suggested mechanism or mode of action or reason for improvement.

Throughout this text, the descriptions refer to antibody molecules and methods of using said antibody molecules. Where the disclosure describes or claims a feature or embodiment associated with an antibody molecule, such a feature or embodiment is equally applicable to the methods of using said antibody molecule. Likewise, where the disclosure describes or claims a feature or embodiment associated with a method of using an antibody molecule, such a feature or embodiment is equally applicable to the antibody molecule.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

Reference to a particular numerical value includes at least that particular value, unless the context clearly dictates otherwise.

When values are expressed as approximations, by use of the antecedent "about," it will be understood that the particular value forms another embodiment. The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

It is to be appreciated that certain features of the disclosed antibody molecules, methods, and uses which are, for clarity, described herein in the context of separate embodiments, may also be provided in combination in a single embodiment. Conversely, various features of the disclosed antibody molecules, methods, and uses that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include, but is not necessarily limited to, examples encompassed by the terms "consisting essentially of" and "consisting of"; similarly, the term "consisting essentially of" is intended to include, but is not necessarily limited to, examples encompassed by the term "consisting of."

The term "antibody molecule" is meant in a broad sense and includes full length immunoglobulin molecules and antigen binding fragments thereof.

Immunoglobulins can be assigned to five major classes, namely IgA, IgD, IgE, IgG, and IgM, depending on the heavy chain constant domain amino acid sequence. IgA and IgG are further sub-classified as the isotypes IgA1, IgA2, IgG1, IgG2, IgG3, and IgG4. Antibody light chains of any vertebrate species can be assigned to one of two clearly distinct types, namely kappa (κ) and lambda (λ), based on the amino acid sequences of their constant domains.

"Antigen binding fragment" refers to a portion of an immunoglobulin molecule that retains the antigen binding properties of the parental full length antibody (i.e. "antigen binding fragment thereof"). Exemplary antigen binding fragments can have: heavy chain complementarity determining regions (HCDR) 1, 2, and/or 3; light chain complementarity determining regions (LCDR) 1, 2, and/or 3; a heavy chain variable region (VH); a light chain variable region (VL); and combinations thereof. Antigen binding fragments include: a Fab fragment, a monovalent fragment consisting of the VL, VH, constant light (CL), and constant heavy 1 (CH1) domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; and a domain antibody (dAb) fragment (Ward et al., Nature 341:544-546, 1989), which consists of a VH domain or a VL domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody, described for example in Int'l Pat. Pub. Nos. WO1998/44001, WO1988/01649, WO1994/13804, and WO1992/01047. These antibody fragments are obtained using techniques well known to those of skill in the art, and the fragments are screened for utility in the same manner as are full length antibodies.

The phrase "immunospecifically binds" refers to the ability of the disclosed antibody molecules to preferentially bind to its target (IL-5 in the case of anti-IL-5 antibody molecules) without preferentially binding other molecules in a sample containing a mixed population of molecules. Antibody molecules that immunospecifically bind IL-5 are substantially free of other antibodies having different antigenic specificities (e.g., an anti-IL-5 antibody is substantially free of antibodies that specifically bind antigens other than IL-5). Antibody molecules that immunospecifically bind IL-5, however, can have cross-reactivity to other antigens, such as orthologs of human IL-5, including *Macaca fascicularis* (cynomolgus monkey) IL-5. The antibody molecules disclosed herein are able to immunospecifically bind both naturally-produced human IL-5 and to IL-5 which is recombinantly produced in mammalian or prokaryotic cells.

An antibody variable region consists of four "framework" regions interrupted by three "antigen binding sites." The antigen binding sites are defined using various terms: (i) Complementarity Determining Regions (CDRs), three in the VH (HCDR1, HCDR2, HCDR3), and three in the VL (LCDR1, LCDR2, LCDR3) are based on sequence variability (Wu and Kabat J Exp Med 132:211-50, 1970; Kabat et al. Sequences of Proteins of Immunological Interest, 5th Ed. Public Health Service, National Institutes of Health, Bethesda, Md., 1991); and (ii) "Hypervariable regions" ("HVR" or "HV"), three in the VH (H1, H2, H3) and three in the VL (L1, L2, L3) refer to the regions of the antibody variable domains which are hypervariable in structure as defined by Chothia and Lesk (Chothia and Lesk Mol Biol 196:901-17, 1987). The AbM definition of CDRs is also widely used; it is a compromise between Kabat and Chothia numbering schemes and is so-called because it was used by Oxford Molecular's AbM antibody modelling software (Rees, A. R., Searle, S. M. J., Henry, A. H. and Pedersen, J. T. (1996) In Steinberg M. J. E. (ed.), Protein Structure Prediction. Oxford University Press, Oxford, 141-172). Other terms include "IMGT-CDRs" (Lefranc et al., Dev Comparat Immunol 27:55-77, 2003) and "Specificity Determining Residue Usage" (SDRU) (Almagro Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined. "Human antibody," "fully human antibody," and like terms refers to an antibody having heavy and light chain variable regions in which both the framework and the antigen binding sites are derived from sequences of human origin. If the antibody contains a constant region, the constant region also is derived from sequences of human origin. A human antibody comprises heavy and/or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to, for example, naturally occurring somatic mutations or intentional introduction of substitutions in the variable domain (framework and antigen binding sites), or constant domain. Typically, a "human antibody" is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical in amino acid sequence to an amino acid sequence encoded by a human germline or rearranged immunoglobulin gene. In some cases, a "human antibody" may contain consensus framework sequences derived from human framework sequence analyses, for example as described in Knappik et al., J Mol Biol 296:57-86, 2000, or synthetic HCDR3 incorporated into human immunoglobulin gene libraries displayed on phage, as described in, for example, Shi et al., J Mol Biol 397:385-96, 2010 and Int'l Pat. Pub. No. WO2009/085462. Antibodies in which antigen binding sites are derived from a non-human species are not included in the definition of "human antibody."

Human antibodies, while derived from human immunoglobulin sequences, may be generated using systems such as phage display incorporating synthetic CDRs and/or synthetic frameworks, or can be subjected to in vitro mutagenesis to improve antibody properties in the variable regions or the constant regions or both, resulting in antibodies that do not naturally exist within the human antibody germline repertoire in vivo.

"Recombinant antibody" includes all antibodies that are prepared, expressed, created, or isolated by recombinant means, such as: antibodies isolated from an animal (e.g., a mouse) that is transgenic or transchromosomal for human immunoglobulin genes or a hybridoma prepared therefrom (described further below); antibodies isolated from a host cell transformed to express the antibody; antibodies isolated from a recombinant, combinatorial antibody library; and antibodies prepared, expressed, created, or isolated by any other means that involve splicing of human immunoglobulin gene sequences to other DNA sequences, or antibodies that are generated in vitro using Fab arm exchange.

"Monoclonal antibody" refers to a population of antibody molecules of a single molecular composition. A monoclonal antibody composition displays a single binding specificity and affinity for a particular epitope, or in a case of a bispecific monoclonal antibody, a dual binding specificity to two distinct epitopes. Monoclonal antibody therefore refers to an antibody population with single amino acid composition in each heavy and each light chain, except for possible well known alterations such as removal of C-terminal lysine from the antibody heavy chain. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" refers to a portion of an antigen to which an antibody specifically binds. Epitopes usually consist of chemically active (such as polar, non-polar, or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions, or deletions. The term "mutation" as used herein is intended to mean one or more intentional substitutions which are made to a polypeptide or polynucleotide.

As used herein "90% identical to" encompasses at least 90% identical, 91% identical, 92% identical, 93% identical, 94% identical, 95% identical, 96% identical, 97% identical, 98% identical, 99% identical, or 100% identical to the reference item (e.g., a biological sequence). The current specification uses the term "% identical" to describe a number of sequences. As would be understood, the term "% identical" means that in a comparison of two sequences over the specified region the two sequences have the specified number of identical residues in the same position. The level of identity may be determined using CLUSTAL W with default parameters.

"Treat," "treatment," and like terms refer to both therapeutic treatment and prophylactic or preventative measures, and includes reducing the severity and/or frequency of symptoms, eliminating symptoms and/or the underlying cause of the symptoms, reducing the frequency or likelihood of symptoms and/or their underlying cause, improving or remediating damage caused, directly or indirectly, by the eosinophilic asthma, hypereosinophilic syndrome, nasal polyposis with eosinophilic involvement, eosinophilic granulomatosis with polyangiitis, atopic dermatitis or eosinophilic esophagitis. Treatment also includes prolonging survival as compared to the expected survival of a subject not receiving treatment. Subjects to be treated include those that have the condition or disorder as well as those prone to have the condition or disorder or those in which the condition or disorder is to be prevented.

As used herein, "administering to the subject" and similar terms indicate a procedure by which the disclosed antibody molecules or compositions comprising the same are injected into a patient such that target cells, tissues, or segments of the body of the subject are contacted with the disclosed antibody molecules.

The phrase "therapeutically effective amount" refers to an amount of the antibody molecules, as described herein, effective to achieve a particular biological or therapeutic result such as, but not limited to, biological or therapeutic results disclosed, described, or exemplified herein. The therapeutically effective amount may vary according to factors such as the disease state, age, sex, and weight of the individual, and the ability of the composition to cause a desired response in a subject. Exemplary indicators of a therapeutically effect amount include, for example, improved well-being of the patient, reduction of a disease symptom, arrested or slowed progression of disease symptoms, and/or absence of disease symptoms.

The following abbreviations are used herein: *Alternaria alternata* (*Alternaria*), *Ascaris suum* (*A. suum*); complementarity-determining region (CDR); heavy chain (HC); light chain (LC); heavy chain variable region (VH); light chain variable region (VL); surface plasmon resonance (SPR).

Antibody Molecules

Disclosed herein are human antibody molecules that immunospecifically bind to human IL-5. The human antibody molecules can immunospecifically bind to human IL-5 with an equilibrium affinity constant ($K_D$) of at least about 40 pM as determined by surface plasmon resonance (SPR). As used herein, "of at least about 40 pM" means that the disclosed antibodies immunospecifically bind human IL-5 with a $K_D$ of less than or equal to about 40 pM. For example, the disclosed antibodies can immunospecifically bind human IL-5 with a $K_D$ of about 40 pM, about 30 pM, about 20 pM, about 10 pM, or less than about 10 pM.

The disclosed human antibody molecules can comprise a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain consensus CDR1 comprising the amino acid sequence of SEQ ID NO: 1, a light chain consensus CDR2 comprising the amino acid sequence of SEQ ID NO: 2, and a light chain consensus CDR3 comprising the amino acid sequence of SEQ ID NO: 3.

The light chain consensus CDR1 comprises the amino acid sequence of $GX_1X_2X_3X_4X_5X_6KX_7X_8Y$ (SEQ ID NO: 1), wherein:
  $X_1$ is G or K;
  $X_2$ is N or D;
  $X_3$ is N or H;
  $X_4$ is I or A;
  $X_5$ is G or D;
  $X_6$ is S or K;
  $X_7$ is N or H; and
  $X_8$ is V or A.

In some embodiments, the light chain CDR1 amino acid sequence can comprise GGNNIGSKNVY (SEQ ID NO: 5). In some embodiments, the light chain CDR1 amino acid sequence can comprise GKNNIGSKNVY (SEQ ID NO: 21). In some embodiments, the light chain CDR1 amino acid sequence can comprise GGDNIGSKNVY (SEQ ID NO: 24). In some embodiments, the light chain CDR1 amino acid sequence can comprise GGNHIGSKNVY (SEQ ID NO: 27). In some embodiments, the light chain CDR1 amino acid sequence can comprise GGNNAGSKNVY (SEQ ID NO: 30). In some embodiments, the light chain CDR1 amino acid sequence can comprise GGNNIDSKNVY (SEQ ID NO: 66). In some embodiments, the light chain CDR1 amino acid sequence can comprise GGNNIGKKNVY (SEQ ID NO: 33). In some embodiments, the light chain CDR1 amino acid sequence can comprise GGNNIGSKHVY (SEQ ID NO: 36). In some embodiments, the light chain CDR1 amino acid sequence can comprise GGNNIGSKNAY (SEQ ID NO: 39).

The light chain CDR2 amino acid sequence comprises $DDX_8X_9RPS$ (SEQ ID NO: 2), wherein:
  $X_8$ is S or L; and
  $X_9$ is D or S.

In some embodiments, the light chain CDR2 amino acid sequence can comprise DDSDRPS (SEQ ID NO: 7). In some embodiments, the light chain CDR2 amino acid sequence can comprise DDLDRPS (SEQ ID NO: 42). In some embodiments, the light chain CDR2 amino acid sequence can comprise DDSSRPS (SEQ ID NO: 45).

The light chain CDR3 amino acid sequence comprises $QVWX_{10}SSSDX_{11}VX_{12}$ (SEQ ID NO: 3), wherein:
  $X_{10}$ is D or L;
  $X_{11}$ is H, S, Y, or D; and
  $X_{12}$ is V, A, or W.

In some embodiments, the light chain CDR3 amino acid sequence can comprise QVWDSSSDHVV (SEQ ID NO: 15). In some embodiments, the light chain CDR3 amino acid sequence can comprise QVWLSSSDHVV (SEQ ID NO: 48). In some embodiments, the light chain CDR3 amino acid sequence can comprise QVWDSSSDSVV (SEQ ID NO: 51). In some embodiments, the light chain CDR3 amino acid sequence can comprise QVWDSSSDYVV (SEQ ID NO: 54). In some embodiments, the light chain CDR3 amino acid sequence can comprise QVWDSSSDDVV (SEQ ID NO: 57). In some embodiments, the light chain CDR3 amino acid sequence can comprise QVWDSSSDHVA (SEQ ID NO: 60). In some embodiments, the light chain CDR3 amino acid sequence can comprise QVWDSSSDHVW (SEQ ID NO: 63).

The disclosed human antibody molecules can comprise a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NOs: 5, 21, 24, 27, 30, 33, 36, 39, or 66, a light chain CDR2 comprising the amino acid sequence of SEQ ID NOs: 7, 42, or 45, and a light chain CDR3 comprising the amino acid sequence of SEQ ID NOs: 15, 48, 51, 54, 57, 60, or 63. Exemplary antibody molecules comprise a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, and a. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 15;

b. a light chain CDR1 comprising the amino acid sequence of SEQ ID NO: 21, a light chain CDR2 comprising the amino acid sequence of SEQ ID NO: 7, and a light chain CDR3 comprising the amino acid sequence of SEQ ID NO: 15;

c. a light chain CDR1 comprising the amino acid sequence of SEQ ID NO: 24, a light chain CDR2 comprising the amino acid sequence of SEQ ID NO: 7, and a light chain CDR3 comprising the amino acid sequence of SEQ ID NO: 15;

d. a light chain CDR1 comprising the amino acid sequence of SEQ ID NO: 27, a light chain CDR2 comprising the amino acid sequence of SEQ ID NO: 7, and a light chain CDR3 comprising the amino acid sequence of SEQ ID NO: 15;

e. a light chain CDR1 comprising the amino acid sequence of SEQ ID NO: 30, a light chain CDR2 comprising the amino acid sequence of SEQ ID NO: 7, and a light chain CDR3 comprising the amino acid sequence of SEQ ID NO: 15;

f. a light chain CDR1 comprising the amino acid sequence of SEQ ID NO: 33, a light chain CDR2 comprising the amino acid sequence of SEQ ID NO: 7, and a light chain CDR3 comprising the amino acid sequence of SEQ ID NO: 15;

g. a light chain CDR1 comprising the amino acid sequence of SEQ ID NO: 36, a light chain CDR2 comprising the amino acid sequence of SEQ ID NO: 7, and a light chain CDR3 comprising the amino acid sequence of SEQ ID NO: 15;

h. a light chain CDR1 comprising the amino acid sequence of SEQ ID NO: 39, a light chain CDR2 comprising the amino acid sequence of SEQ ID NO: 7, and a light chain CDR3 comprising the amino acid sequence of SEQ ID NO: 15;

i. a light chain CDR1 comprising the amino acid sequence of SEQ ID NO: 66, a light chain CDR2 comprising the amino acid sequence of SEQ ID NO: 7, and a light chain CDR3 comprising the amino acid sequence of SEQ ID NO: 15;

j. a light chain CDR1 comprising the amino acid sequence of SEQ ID NO: 5, a light chain CDR2 comprising the amino acid sequence of SEQ ID NO: 42, and a light chain CDR3 comprising the amino acid sequence of SEQ ID NO: 15;

k. a light chain CDR1 comprising the amino acid sequence of SEQ ID NO: 5, a light chain CDR2 comprising the amino acid sequence of SEQ ID NO: 45, and a light chain CDR3 comprising the amino acid sequence of SEQ ID NO: 15;

l. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 48;

m. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 51;

n. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 54;

o. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 57;

p. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 60; or q. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 63;

wherein the position of the amino acid residues of the CDR is determined according to AbM.

The disclosed antibody molecules can comprise a heavy chain variable region comprising an amino acid sequence that is at least 90%, 95%, 96%, 97%, 98%, 99%, or 100% identical to the amino acid sequence of SEQ ID NO: 16 and a light chain variable region comprising an amino acid sequence that is at least 90%, 95%, 96%, 97%, 98%, 99%, or 100% identical to the amino acid sequence of SEQ ID NO: 17, 22, 25, 28, 31, 34, 37, 40, 43, 46, 49, 52, 55, 58, 61, 64, or 67, wherein the variability (i.e. the at least 90%, 95%, 96%, 97%, 98%, 99%, or 100% identity) occurs outside of the CDR sequence. Exemplary antibody molecules are provided in Table 1 and Table 15.

TABLE 1

Antibody chain/domain composition summary

| Antibody ID | VH protein/ (SEQ ID) | VL protein/ (SEQ ID) | HC protein/ (SEQ ID) | LC protein/ (SEQ ID) |
|---|---|---|---|---|
| 3A5 | 3A5 VH (SEQ ID NO: 10) | 3A5 VL (SEQ ID NO: 11) | 3A5 HC (SEQ ID NO: 12) | 3A5 LC (SEQ ID NO: 13) |
| 3A5.001 | 3A5 VH (SEQ ID NO: 10) | 3A5 VL (SEQ ID NO: 11) | 3A5.001 HC (SEQ ID NO: 14) | 3A5 LC (SEQ ID NO: 13) |
| 3A5.040 | 3A5.040 VH (SEQ ID NO: 16) | 3A5.040 VL (SEQ ID NO: 17) | 3A5.040 HC (SEQ ID NO: 18) | 3A5.040 LC (SEQ ID NO: 19) |
| 3A5.046 | 3A5.040 VH (SEQ ID NO: 16) | 3A5.040 VL (SEQ ID NO: 17) | 3A5.046 HC (SEQ ID NO: 20) | 3A5.040 LC (SEQ ID NO: 19) |
| 3A5.063 | 3A5.040 VH (SEQ ID NO: 16) | 3A5.040 VL + G25K (SEQ ID NO: 22) | 3A5.040 HC (SEQ ID NO: 18) | 3A5.040 LC + G25K (SEQ ID NO: 23) |
| 3A5.070 | 3A5.040 VH (SEQ ID NO: 16) | 3A5.040 VL + N26D (SEQ ID NO: 25) | 3A5.040 HC (SEQ ID NO: 18) | 3A5.040 LC + N26D (SEQ ID NO: 26) |
| 3A5.082 | 3A5.040 VH (SEQ ID NO: 16) | 3A5.040 VL + N27H (SEQ ID NO: 28) | 3A5.040 HC (SEQ ID NO: 18) | 3A5.040 LC + N27H (SEQ ID NO: 29) |
| 3A5.084 | 3A5.040 VH (SEQ ID NO: 16) | 3A5.040 VL + I28A (SEQ ID NO: 31) | 3A5.040 HC (SEQ ID NO: 18) | 3A5.040 LC + I28A (SEQ ID NO: 32) |
| 3A5.097 | 3A5.040 VH (SEQ ID NO: 16) | 3A5.040 VL + G29D (SEQ ID NO: 67) | 3A5.040 HC (SEQ ID NO: 18) | 3A5.040 LC + G29D (SEQ ID NO: 68) |
| 3A5.107 | 3A5.040 VH (SEQ ID NO: 16) | 3A5.040 VL + S30K (SEQ ID NO: 34) | 3A5.040 HC (SEQ ID NO: 18) | 3A5.040 LC + S30K (SEQ ID NO: 35) |
| 3A5.125 | 3A5.040 VH (SEQ ID NO: 16) | 3A5.040 VL + N32H (SEQ ID NO: 37) | 3A5.040 HC (SEQ ID NO: 18) | 3A5.040 LC + N32H (SEQ ID NO: 38) |
| 3A5.127 | 3A5.040 VH (SEQ ID NO: 16) | 3A5.040 VL + V33A (SEQ ID NO: 40) | 3A5.040 HC (SEQ ID NO: 18) | 3A5.040 LC + V33A (SEQ ID NO: 41) |
| 3A5.161 | 3A5.040 VH (SEQ ID NO: 16) | 3A5.040 VL + S52L (SEQ ID NO: 43) | 3A5.040 HC (SEQ ID NO: 18) | 3A5.040 LC + S52L (SEQ ID NO: 44) |

TABLE 1-continued

Antibody chain/domain composition summary

| Antibody ID | VH protein/ (SEQ ID) | VL protein/ (SEQ ID) | HC protein/ (SEQ ID) | LC protein/ (SEQ ID) |
|---|---|---|---|---|
| 3A5.169 | 3A5.040 VH (SEQ ID NO: 16) | 3A5.040 VL + D53S (SEQ ID NO: 46) | 3A5.040 HC (SEQ ID NO: 18) | 3A5.040 LC + D53S (SEQ ID NO: 47) |
| 3A5.232 | 3A5.040 VH (SEQ ID NO: 16) | 3A5.040 VL + D92L (SEQ ID NO: 49) | 3A5.040 HC (SEQ ID NO: 18) | 3A5.040 LC + D92L (SEQ ID NO: 50) |
| 3A5.276* | 3A5.040 VH (SEQ ID NO: 16) | 3A5.040 VL + H95bS (SEQ ID NO: 52) | 3A5.040 HC (SEQ ID NO: 18) | 3A5.040 LC + H95bS (SEQ ID NO: 53) |
| 3A5.278* | 3A5.040 VH (SEQ ID NO: 16) | 3A5.040 VL + H95bY (SEQ ID NO: 55) | 3A5.040 HC (SEQ ID NO: 18) | 3A5.040 LC + H95bY (SEQ ID NO: 56) |
| 3A5.279* | 3A5.040 VH (SEQ ID NO: 16) | 3A5.040 VL + H95bD (SEQ ID NO: 58) | 3A5.040 HC (SEQ ID NO: 18) | 3A5.040 LC + H95bD (SEQ ID NO: 59) |
| 3A5.294 | 3A5.040 VH (SEQ ID NO: 16) | 3A5.040 VL + V97A (SEQ ID NO: 61) | 3A5.040 HC (SEQ ID NO: 18) | 3A5.040 LC + V97A (SEQ ID NO: 62) |
| 3A5.302 | 3A5.040 VH (SEQ ID NO: 16) | 3A5.040 VL + V97W (SEQ ID NO: 64) | 3A5.040 HC (SEQ ID NO: 18) | 3A5.040 LC + V97W (SEQ ID NO: 65) |

*The lower case "b" in each of these sequences refers to the Kabat numbering for the CDR position. Kabat numbering allows for CDRs of variable sizes, by using alphanumeric numbering to denote amino acid insertions at certain positions. In these CDR sequences, additional amino acids were present, which were numbered as positions 95a and 95b (corresponding to Kabat positions 95A and 95B respectively). Thus, for antibody 3A5.276, for example, H95bS indicates a histidine ("H") to serine ("S") mutation at position 95B according to Kabat number relative to the 3A5.040 VL chain. The lower case notation is therefore used here to distinguish the Kabat number, separate from the mutation at the indicated Kabat position.

In some embodiments, the disclosed antibody molecules can comprise a heavy chain variable region comprising an amino acid sequence that is at least 90%, 95%, 96%, 97%, 98%, 99%, or 100% identical to the amino acid sequence of SEQ ID NO: 16 and a. a light chain variable region comprising an amino acid sequence that is at least 90%, 95%, 96%, 97%, 98%, 99%, or 100% identical to the amino acid sequence of SEQ ID NO: 17;
b. a light chain variable region comprising an amino acid sequence that is at least 90%, 95%, 96%, 97%, 98%, 99%, or 100% identical to the amino acid sequence of SEQ ID NO: 22;
c. a light chain variable region comprising an amino acid sequence that is at least 90%, 95%, 96%, 97%, 98%, 99%, or 100% identical to the amino acid sequence of SEQ ID NO: 25;
d. a light chain variable region comprising an amino acid sequence that is at least 90%, 95%, 96%, 97%, 98%, 99%, or 100% identical to the amino acid sequence of SEQ ID NO: 28;
e. a light chain variable region comprising an amino acid sequence that is at least 90%, 95%, 96%, 97%, 98%, 99%, or 100% identical to the amino acid sequence of SEQ ID NO: 31;
f. a light chain variable region comprising an amino acid sequence that is at least 90%, 95%, 96%, 97%, 98%, 99%, or 100% identical to the amino acid sequence of SEQ ID NO: 34;
g. a light chain variable region comprising an amino acid sequence that is at least 90%, 95%, 96%, 97%, 98%, 99%, or 100% identical to the amino acid sequence of SEQ ID NO: 37;
h. a light chain variable region comprising an amino acid sequence that is at least 90%, 95%, 96%, 97%, 98%, 99%, or 100% identical to the amino acid sequence of SEQ ID NO: 40;
i. a light chain variable region comprising an amino acid sequence that is at least 90%, 95%, 96%, 97%, 98%, 99%, or 100% identical to the amino acid sequence of SEQ ID NO: 43;
j. a light chain variable region comprising an amino acid sequence that is at least 90%, 95%, 96%, 97%, 98%, 99%, or 100% identical to the amino acid sequence of SEQ ID NO: 46;
k. a light chain variable region comprising an amino acid sequence that is at least 90%, 95%, 96%, 97%, 98%, 99%, or 100% identical to the amino acid sequence of SEQ ID NO: 49;
l. a light chain variable region comprising an amino acid sequence that is at least 90%, 95%, 96%, 97%, 98%, 99%, or 100% identical to the amino acid sequence of SEQ ID NO: 52;
m. a light chain variable region comprising an amino acid sequence that is at least 90%, 95%, 96%, 97%, 98%, 99%, or 100% identical to the amino acid sequence of SEQ ID NO: 55;
n. a light chain variable region comprising an amino acid sequence that is at least 90%, 95%, 96%, 97%, 98%, 99%, or 100% identical to the amino acid sequence of SEQ ID NO: 58;
o. a light chain variable region comprising an amino acid sequence that is at least 90%, 95%, 96%, 97%, 98%, 99%, or 100% identical to the amino acid sequence of SEQ ID NO: 61;
p. a light chain variable region comprising an amino acid sequence that is at least 90%, 95%, 96%, 97%, 98%, 99%, or 100% identical to the amino acid sequence of SEQ ID NO: 64; or
q. a light chain variable region comprising an amino acid sequence that is at least 90%, 95%, 96%, 97%, 98%, 99%, or 100% identical to the amino acid sequence of SEQ ID NO: 67, wherein the variability (i.e. the at least 90%, 95%, 96%, 97%, 98%, 99%, or 100% identity) occurs outside of the CDR sequence.

The disclosed antibody molecules can comprise one or more mutations, deletions, or insertions, in the framework and/or constant regions. In some embodiments, an IgG4 antibody molecule can comprise a S228P mutation. S228 is located in the hinge region of the IgG4 antibody molecule. Mutation of the serine ("S") to a proline ("P") serves to stabilize the hinge of the IgG4 and prevent Fab arm exchange in vitro and in vivo. In some embodiments, the antibody molecules can comprise one or more modifications which increase the in vivo half life of the antibody molecules. For instance in certain embodiments the antibody can comprise a M252Y mutation, a S254T mutation, and a T256E mutation (collectively referred to as the "YTE" mutation). M252, S254, and T256 are located in the CH2 domain of the heavy chain. Mutation of these residues to tyrosine ("Y"), threonine ("T"), and glutamate ("E"), respectively, protects the antibody molecules from lysosomal degradation, thereby enhancing the serum half-life of the antibody molecules. Based on the example of other antibodies, it is contemplated that the introduction of the YTE mutation in an anti-IL-5 antibody may provide sufficient extension of serum half life to allow for administration regimes with 3 months or longer inter-dosing intervals. In some embodiments, the antibody molecules can comprise a deletion of the heavy chain C-terminal lysine residue. Deletion of the heavy chain C-terminal lysine residue reduces heterogeneity of the antibody molecules when produced by mammalian cells. In some embodiments, the antibody molecules can comprise a combination of mutations, deletions, or insertions. For example, in some aspects, the disclosed antibody molecules can comprise a S228P mutation and a deletion of a heavy chain C-terminal lysine residue. The disclosed antibodies comprising a heavy chain sequence of SEQ ID NO: 18, for example, comprise a S228P mutation and a deletion of a heavy chain C-terminal lysine residue. In some aspects, the disclosed antibody molecule can comprise a S228P mutation, a M252Y mutation, a S254T mutation, a T256E mutation, and a deletion of a heavy chain C-terminal lysine residue. The 3A5.046 antibody, for example, which comprises a heavy chain of SEQ ID NO: 20, comprises a S228P mutation, a M252Y mutation, a S254T mutation, a T256E mutation, and a deletion of a heavy chain C-terminal lysine residue.

The antibody molecule can comprise an IgG1 or IgG4 heavy chain constant region and a lambda light chain constant region. In some embodiments, the antibody molecule comprises an IgG1 heavy chain constant region and a lambda light chain constant region (antibody 3A5, for example). In some embodiments, the antibody molecule comprises an IgG4 heavy chain constant region and a lambda light chain constant region.

The disclosed antibody molecules can comprise a heavy chain comprising an amino acid sequence that is at least 90%, 95%, 96%, 97%, 98%, 99%, or 100% identical to the amino acid sequence of SEQ ID NOs: 18 or 20 and a light chain comprising an amino acid sequence that is at least 90%, 95%, 96%, 97%, 98%, 99%, or 100% identical to the amino acid sequence of SEQ ID NO: 19, 23, 26, 29, 32, 35, 38, 41, 44, 47, 50, 53, 56, 59, 62, 65, or 68, wherein the variability (i.e. the at least 90% identity) occurs outside of the CDR sequence. Exemplary antibody molecules are provided in Table 1 and Table 15. In some embodiments, the antibody molecules can comprise a heavy chain comprising an amino acid sequence that is at least 90%, 95%, 96%, 97%, 98%, 99%, or 100% identical to the amino acid sequence of SEQ ID NO: 18 and a. a light chain comprising an amino acid sequence that is at least 90%, 95%, 96%, 97%, 98%, 99%, or 100% identical to the amino acid sequence of SEQ ID NO: 19;

b. a light chain comprising an amino acid sequence that is at least 90%, 95%, 96%, 97%, 98%, 99%, or 100% identical to the amino acid sequence of SEQ ID NO: 23;

c. a light chain comprising an amino acid sequence that is at least 90%, 95%, 96%, 97%, 98%, 99%, or 100% identical to the amino acid sequence of SEQ ID NO: 26;

d. a light chain comprising an amino acid sequence that is at least 90%, 95%, 96%, 97%, 98%, 99%, or 100% identical to the amino acid sequence of SEQ ID NO: 29;

e. a light chain comprising an amino acid sequence that is at least 90%, 95%, 96%, 97%, 98%, 99%, or 100% identical to the amino acid sequence of SEQ ID NO: 32;

f. a light chain comprising an amino acid sequence that is at least 90%, 95%, 96%, 97%, 98%, 99%, or 100% identical to the amino acid sequence of SEQ ID NO: 35;

g. a light chain comprising an amino acid sequence that is at least 90%, 95%, 96%, 97%, 98%, 99%, or 100% identical to the amino acid sequence of SEQ ID NO: 38;

h. a light chain comprising an amino acid sequence that is at least 90%, 95%, 96%, 97%, 98%, 99%, or 100% identical to the amino acid sequence of SEQ ID NO: 41;

i. a light chain comprising an amino acid sequence that is at least 90%, 95%, 96%, 97%, 98%, 99%, or 100% identical to the amino acid sequence of SEQ ID NO: 44;

j. a light chain comprising an amino acid sequence that is at least 90%, 95%, 96%, 97%, 98%, 99%, or 100% identical to the amino acid sequence of SEQ ID NO: 47;

k. a light chain comprising an amino acid sequence that is at least 90%, 95%, 96%, 97%, 98%, 99%, or 100% identical to the amino acid sequence of SEQ ID NO: 50;

l. a light chain comprising an amino acid sequence that is at least 90%, 95%, 96%, 97%, 98%, 99%, or 100% identical to the amino acid sequence of SEQ ID NO: 53;

m. a light chain comprising an amino acid sequence that is at least 90%, 95%, 96%, 97%, 98%, 99%, or 100% identical to the amino acid sequence of SEQ ID NO: 56;

n. a light chain comprising an amino acid sequence that is at least 90%, 95%, 96%, 97%, 98%, 99%, or 100% identical to the amino acid sequence of SEQ ID NO: 59;

o. a light chain comprising an amino acid sequence that is at least 90%, 95%, 96%, 97%, 98%, 99%, or 100% identical to the amino acid sequence of SEQ ID NO: 62;

p. a light chain comprising an amino acid sequence that is at least 90%, 95%, 96%, 97%, 98%, 99%, or 100% identical to the amino acid sequence of SEQ ID NO: 65; or q. a light chain comprising an amino acid sequence that is at least 90%, 95%, 96%, 97%, 98%, 99%, or 100% identical to the amino acid sequence of SEQ ID NO: 68, wherein the variability (i.e. the at least 90%, 95%, 96%, 97%, 98%, 99%, or 100% identity) occurs outside of the CDR sequence.

The disclosed antibody molecules can comprise a heavy chain comprising an amino acid sequence that is at least 90%, 95%, 96%, 97%, 98%, 99%, or 100% identical to the amino acid sequence of SEQ ID NO: 20 and a light chain comprising an amino acid sequence that is at least 90%, 95%, 96%, 97%, 98%, 99%, or 100% identical to the amino acid sequence of SEQ ID NO: 19, wherein the variability (i.e. the at least 90%, 95%, 96%, 97%, 98%, 99%, or 100% identity) occurs outside of the CDR sequence.

In some embodiments, the antibody molecules are full length antibody molecules (with or without a deletion of the heavy chain C-terminal lysine residue). In other embodiments, the antibody molecules are antigen binding fragments. Suitable antibody binding fragments include, but are not limited to, a Fab fragment, a Fab2 fragment, or a single chain antibody.

The antibody molecules can have one or more of the following properties:
a. binds to human IL-5 with an equilibrium affinity constant ($K_D$) of at least about 40 pM as determined by surface plasmon resonance;
b. reduces binding of IL-5 to the IL-5 receptor;
c. has a serum half-life of at least about 20 days; or
d. binds human and cynomolgus monkey IL-5 but not mouse, rat, or guinea pig IL-5.

Pharmaceutical compositions comprising any of the disclosed antibody molecules are also provided.

Also provided are nucleic acid molecules encoding any of the disclosed antibody molecules and vectors comprising the disclosed nucleic acid molecules.

Cells transformed to express any of the disclosed antibody molecules are further provided.

Methods and Uses

The disclosed antibody molecules, or pharmaceutical compositions comprising the same, can be used to treat eosinophilic asthma, hypereosinophilic syndrome, nasal polyposis with eosinophilic involvement, eosinophilic granulomatosis with polyangiitis, atopic dermatitis and eosinophilic esophagitis. Any of the antibody molecule characteristics disclosed herein apply equally to the antibodies used in the disclosed methods and uses.

Disclosed herein are methods of treating a subject having eosinophilic asthma, hypereosinophilic syndrome, nasal polyposis with eosinophilic involvement, eosinophilic granulomatosis with polyangiitis, atopic dermatitis or eosinophilic esophagitis comprising administering to the subject a therapeutically effective amount of any of the antibody molecules disclosed herein, or pharmaceutical compositions comprising the same, to treat the eosinophilic asthma, hypereosinophilic syndrome, nasal polyposis with eosinophilic involvement, eosinophilic granulomatosis with polyangiitis, atopic dermatitis or eosinophilic esophagitis.

The use of an effective amount of any of the disclosed antibody molecules, or pharmaceutical compositions comprising the same, in the treatment of eosinophilic asthma, hypereosinophilic syndrome, nasal polyposis with eosinophilic involvement, eosinophilic granulomatosis with polyangiitis, atopic dermatitis or eosinophilic esophagitis is also provided.

Also provided is the use of any of the disclosed antibody molecules, or pharmaceutical compositions comprising the same, in the manufacture of a medicament for the treatment of eosinophilic asthma, hypereosinophilic syndrome, nasal polyposis with eosinophilic involvement, eosinophilic granulomatosis with polyangiitis, atopic dermatitis or eosinophilic esophagitis.

EXAMPLES

The following examples are provided to further describe some of the embodiments disclosed herein. The examples are intended to illustrate, not to limit, the disclosed embodiments.

Generation of Anti-Human-IL-5 Antibodies

Anti-human-IL-5 antibodies were obtained from transgenic rats (OMT) with human V-genes cloned into their genomes and which produce antibodies with human V-domains and rat Fc domains. Briefly, the transgenic rats were genetically immunized with DNA encoding IL-5 four times over 21 days (on days 0, 7, 14, 21) and boosted with recombinant human IL-5 at day 28 of the immunization protocol. Serum antibody titres were determined at days 0 and 38 of the immunization protocol by an ELISA assay using recombinant human IL-5. Briefly, sera from each animal were diluted in PBS 1% BSA and were tested using ELISA plates coated with 1 µg/ml human IL-5, or BSA as a control. A goat anti-rat IgG R-phycoerythrin conjugate (SouthernBiotech, #3030-09) was used at 10 g/ml as a secondary antibody. Specific animals were chosen for hybridoma fusion based on these serum titres.

To generate hybridomas which produce monoclonal antibodies to human IL-5, splenocytes and/or lymph node cells from immunized animals were isolated and fused to P3X63Ag8.653 non-secreting mouse myeloma cells (ATCC, CRL-1580). Cells were plated at approximately $1 \times 10^5$ cells/mL in flat bottom microtiter plates, followed by a two week incubation in selective medium which included 10% fetal clone serum and 1×HAT (Sigma). Hybridomas were expanded by serial passage through four media changes in 96-well plates (96-well stages 1 to 4), then into T25 and finally T75 flasks.

The supernatants from hybridoma clones were assayed during the hybridoma expansion process, initially in a whole-cell ELISA using cells transfected with GPI-anchored human IL-5 and then ELISA using a recombinant human IL-5 ELISA assay (the latter as described above). Hybridomas which survived the scale-up process to T75 stage and which gave signals above a given threshold for binding in both of these assays were frozen as cell pellets, for cloning and sequencing of Ig v-domains. Approximately 20 hybridomas producing chimeric IgGs were selected for cloning following these screening steps.

The human v-domains from the candidate chimeric IgGs were isolated by generation of cDNA from hybridoma cell pellets, PCR amplification of v-domains, subcloning, and DNA sequencing. A total of approximately 35 heavy and light chain combinations were obtained from the sequencing of these hybridomas. All antibodies were cloned into a mammalian expression vector and transiently transfected into HEK-293 cells. Antibodies were purified using standard Protein A purification protocols.

Functional Testing and Characterization of Antibodies

Selected antibodies in human IgG1 format were first assayed for specificity in a human IL-5 ELISA. Briefly, antibodies were diluted in PBS 0.1% BSA and were tested using ELISA plates coated with 1 µg/ml human IL-5, or an irrelevant control protein. A horseradish peroxidase-conjugated Anti-IgG antibody was used as a secondary antibody.

Antibodies that showed immunospecific binding to human IL-5 were ranked for potency in a human IL-5-dependent cell proliferation assay using human TF-1.6G4 (a derivative of the human erythroleukemic cell line TF-1) cells. The TF-1.6G4 cell line was subcloned and selected for enhanced surface expression of IL-5Rα and consistent proliferative response to human IL-5. The TF-1.6G4 cell line was maintained in culture following standard conditions used for the TF-1 human erythroleukemic cell line (ATCC: CRL-2003). Briefly, dilutions of each antibody were incubated in the presence of 45 pM human IL-5 and $5 \times 10^4$ TF-1.6G4 cells per well, incubated for 48 h, and cell proliferation was determined using the CellTiter-Glo® Luminescent Cell Viability Assay (Promega, Wis.). All proliferation and inhibition curves were fitted using a three- or four-parameter dose-response model in GraphPad Prism 6 (Version 6.04) software. Table 2 summarizes these results.

TABLE 2

Summary of screening and characterization of an initial test panel in IgG1 format.

| Test Antibody | IC50 (pM) in TF1.6G4 | Equilibrium Affinity ($K_D$) | Inhibits IL-5Rα binding | Specificity confirmed by ELISA |
|---|---|---|---|---|
| 3A5 | 35.07 | 36 pM | Yes | Yes |
| 1A3 | 55.5 | 18 pM | Yes | Yes |
| 2B4 | 56.75 | 42 pM | Yes | Yes |
| 6G10 | 72.34 | 61 pM | Yes | Yes |
| 1E8 | 72.45 | 28 pM | Yes | Yes |
| 3G4 | 80.92 | 41 pM | Yes | Yes |
| 6C9 | 81.89 | 41 pM | Yes | Yes |
| 5H1 | 86.42 | 36 pM | Yes | Yes |
| 1H10 | 93.26 | 18 pM | Yes | Yes |
| 5H11 | 109.3 | 36 pM | No | Yes |
| 5G9 | 184.4 | 52 pM | Yes | Yes |
| 1B2 | 214.4 | 45 pM | Yes | Yes |

In Table 2, the results of tests were ranked in order of TF1.6G4 assay potency. The initial test panel was selected based upon potency, affinity, IL-5Rα inhibition and sequence liabilities (immunogenicity and developability).

Figure 6:
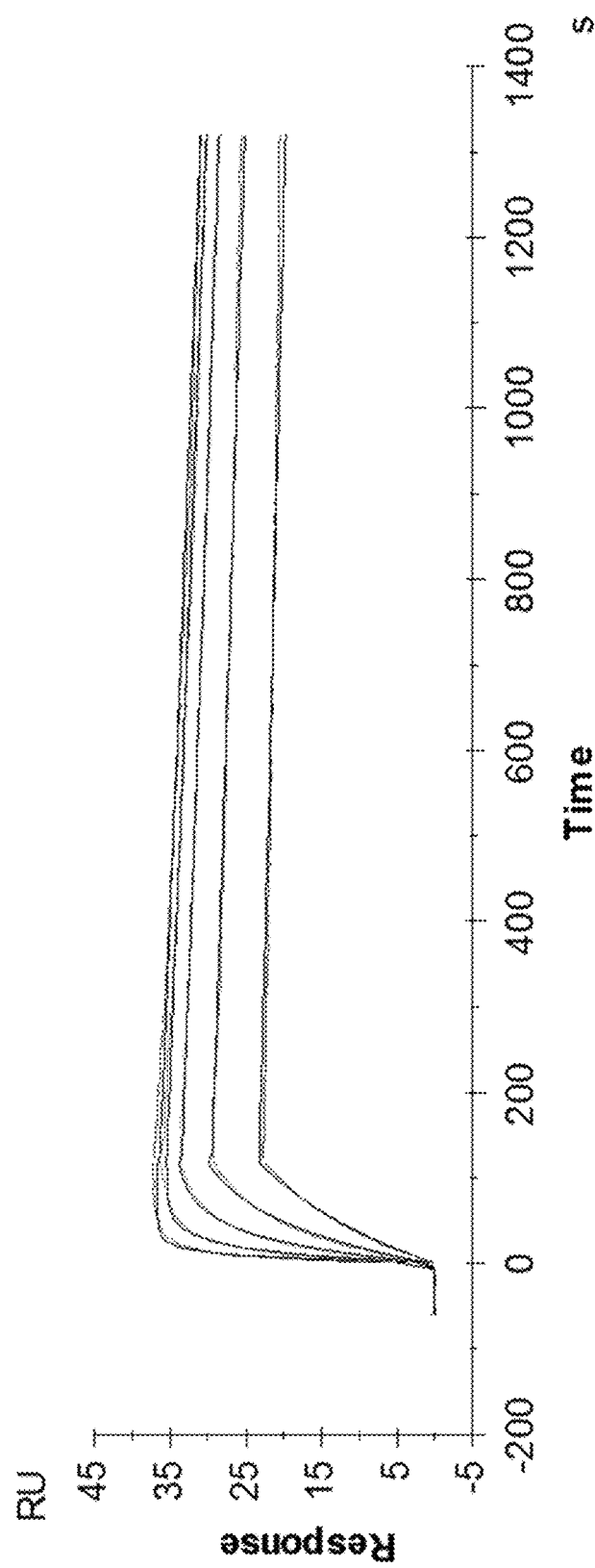
FIG. 6 illustrates a multi-concentration Biacore kinetic analysis of 3A5.046 antibody binding to recombinant human IL-5 at 2.5, 1.25, 0.625, 0.313 and 0.156 µg/mL. Sensorgrams show decreasing concentrations of IL-5 in order from 2.5 µg/mL IL-5 in the top trace to 0.156 µg/mL IL-5 in the bottom trace.

Biacore assays were used to determine the affinity of test antibodies to recombinant human IL-5 and their potency in inhibiting IL-5Rα binding to human IL-5. Table 2 summarizes these results. Binding affinity of test antibodies to human IL-5 ($K_D$; FIG. 6) was determined on a Biacore T200 system (GE Healthcare) by coating a Biacore Series S Sensor Chip Protein A (GE Healthcare) with selected purified IgG antibody to a capture level of 75 RU, then recombinant human IL-5 was injected at 60 µL/min across a 7-step two-fold serial dilution range, starting at 1 µg/mL. All experiments were run using HBS-EP+ buffer (GE Healthcare). The resulting sensorgrams were double-referenced (test flowcell values subtracted from control (Protein A surface with no coated antibody) flowcell values and also a buffer blank). Binding constants were determined by fitting a 1:1 Langmuir binding model to double-referenced sensorgrams.

To determine whether each test antibody inhibited the binding of IL-5 to IL-5Rα, either a Biacore T200 or a Biacore 3000 system (GE Healthcare) was used. A Biacore CM5 Sensor Chip was first derivatized with a Fab capture kit (GE Healthcare) in accordance with the manufacturer's instructions on two adjacent (test and control) flowcells. This surface was used to capture each purified IgG test antibody on a single test flowcell. Recombinant human IL-5 at 5 µg/mL or a buffer blank was then injected across both test and control flowcells, to saturate the test flowcell surface and control for non-specific association of IL-5, respectively. A second injection of purified IgG test antibody at 10 µg/mL or a buffer blank was performed on the test flowcell to block free IL-5 binding sites and control for dissociation of the IgG test antibody from the Fab capture antibody, respectively.

Subsequent injection of IL-5Rα-Fc (R&D Systems) at either 5 or 20 µg/mL or a buffer blank across both flowcells was used to determine whether the IgG test antibody blocked the interaction between IL-5 and IL-5Rα or to control for dissociation of IgG antibody from the Fab capture antibody during this step. Antibodies which inhibited the binding of IL-5 to IL-5Rα showed a markedly reduced signal upon injection of IL-5Rα (Table 2). A triple reference subtraction method was used to analyze data in the manner detailed above. All data was exported from Biacore evaluation software and subtracted in Excel (Microsoft) software. All experiments were run using HBS-EP+ buffer (GE Healthcare).

A smaller panel of test antibodies (3A5, 5H11 and 2B4 in Table 2) was chosen on the basis of these results. The antibodies were reformatted as human IgG4 and tested in the same assays. The IgG4 version of antibody 3A5 (originally an IgG1) was designated as 3A5.001. This fully-human antibody was demonstrated to have equivalent potency to the original test 3A5 in IgG1 format (FIG. 1).

Figure 2:
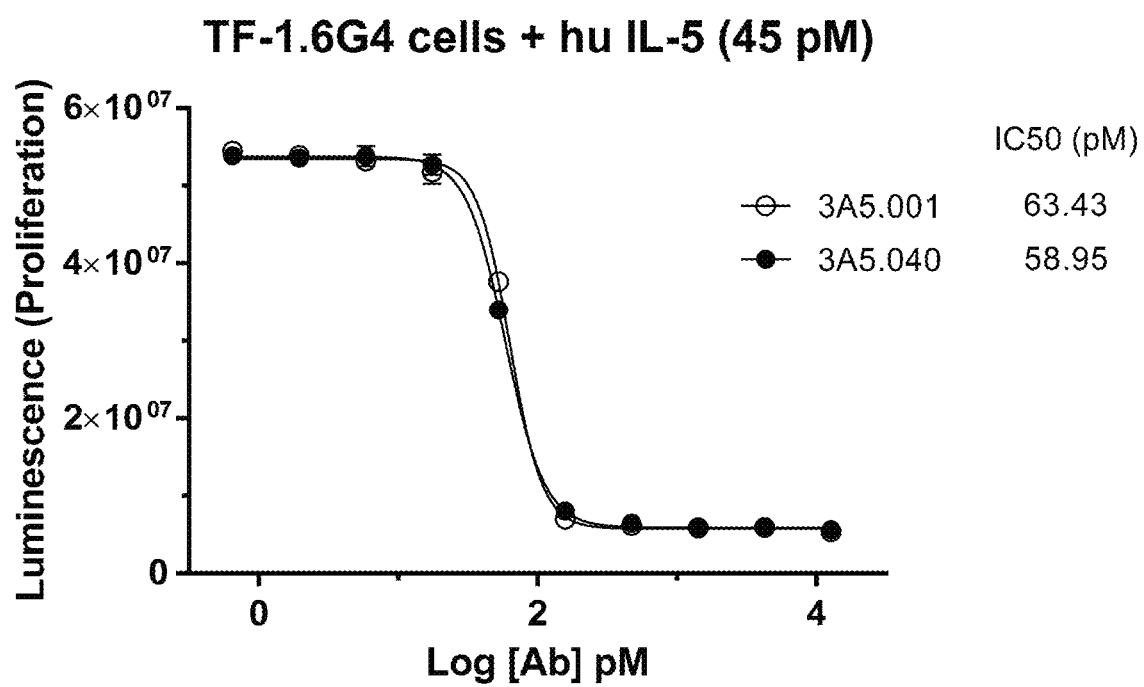
FIG. 2 illustrates a TF-1.6G4 assay showing that antibody variant 3A5.040 retained an equivalent potency to the parent antibody 3A5.001.

A variant of antibody 3A5.001 (designated 3A5.040) was prepared with specific amino acid substitutions (VH: S[68]T, N[82A]S; VL: S[2]Y, I[3]V, Y[92]D, wherein the residues in square brackets represent the Kabat positions) introduced in the V-domain regions to remove predicted T-cell epitopes. Antibody 3A5.040 was demonstrated to have equivalent potency to its parental antibody, 3A5.001 (FIG. 2) in the TF-1.6G4 assay.

Figure 3:
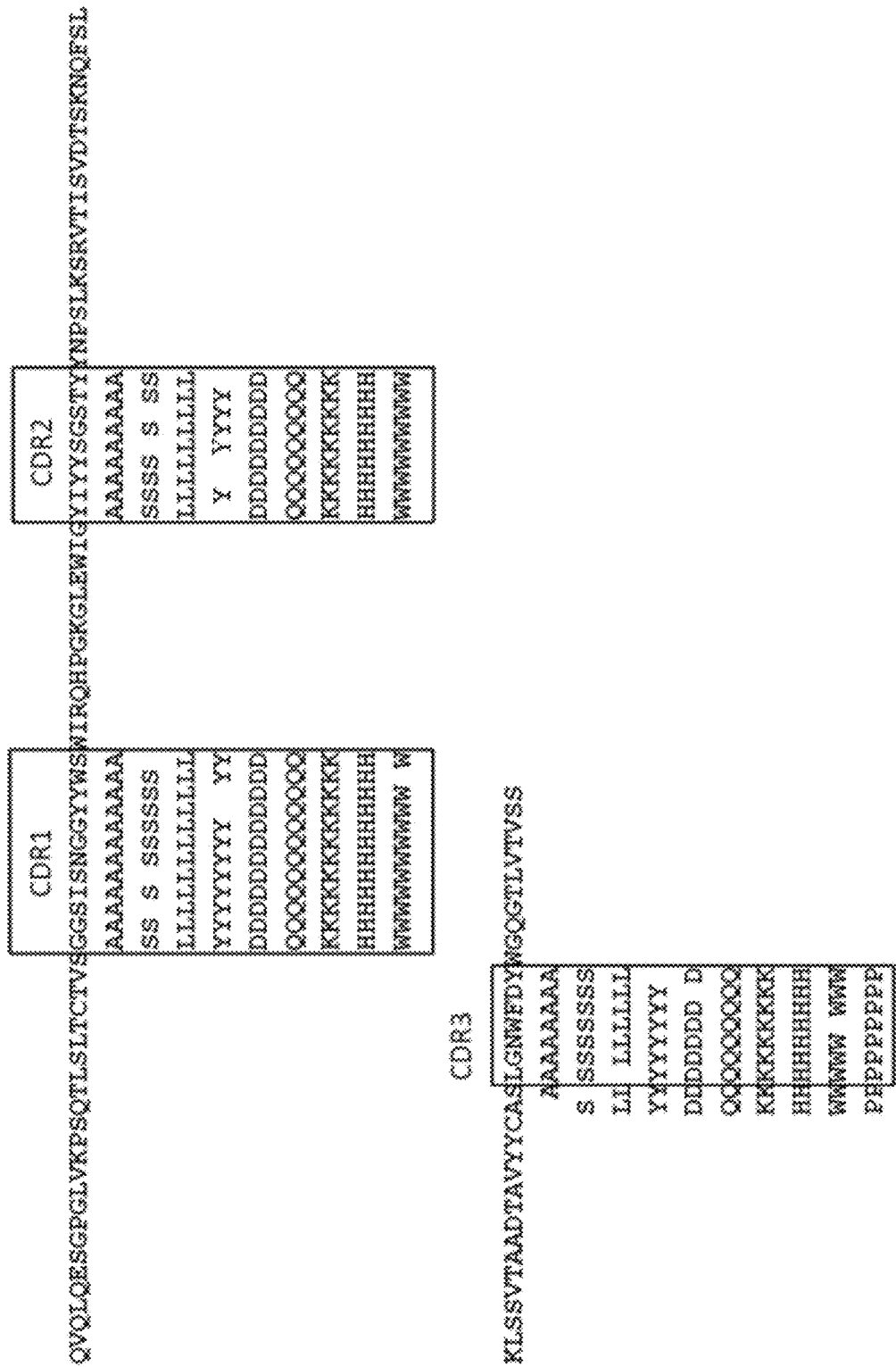
FIG. 3 is a graphical matrix showing the position and identity of the different single amino acid substitutions that were generated on the 3A5.040 VH CDRs, aligned to the original 3A5.040 VH sequence (top sequence). The boxes contain the residues which were designated CDR residues according to the AbM nomenclature. In addition to the CDR residues, variants were made to Kabat residue numbers 93 and 94 (adjacent to HC CDR3) as described in the Example "Functional testing and characterization of antibodies." The various sequences recited in this figure are provided in SEQ ID NO:73.
Figure 4:
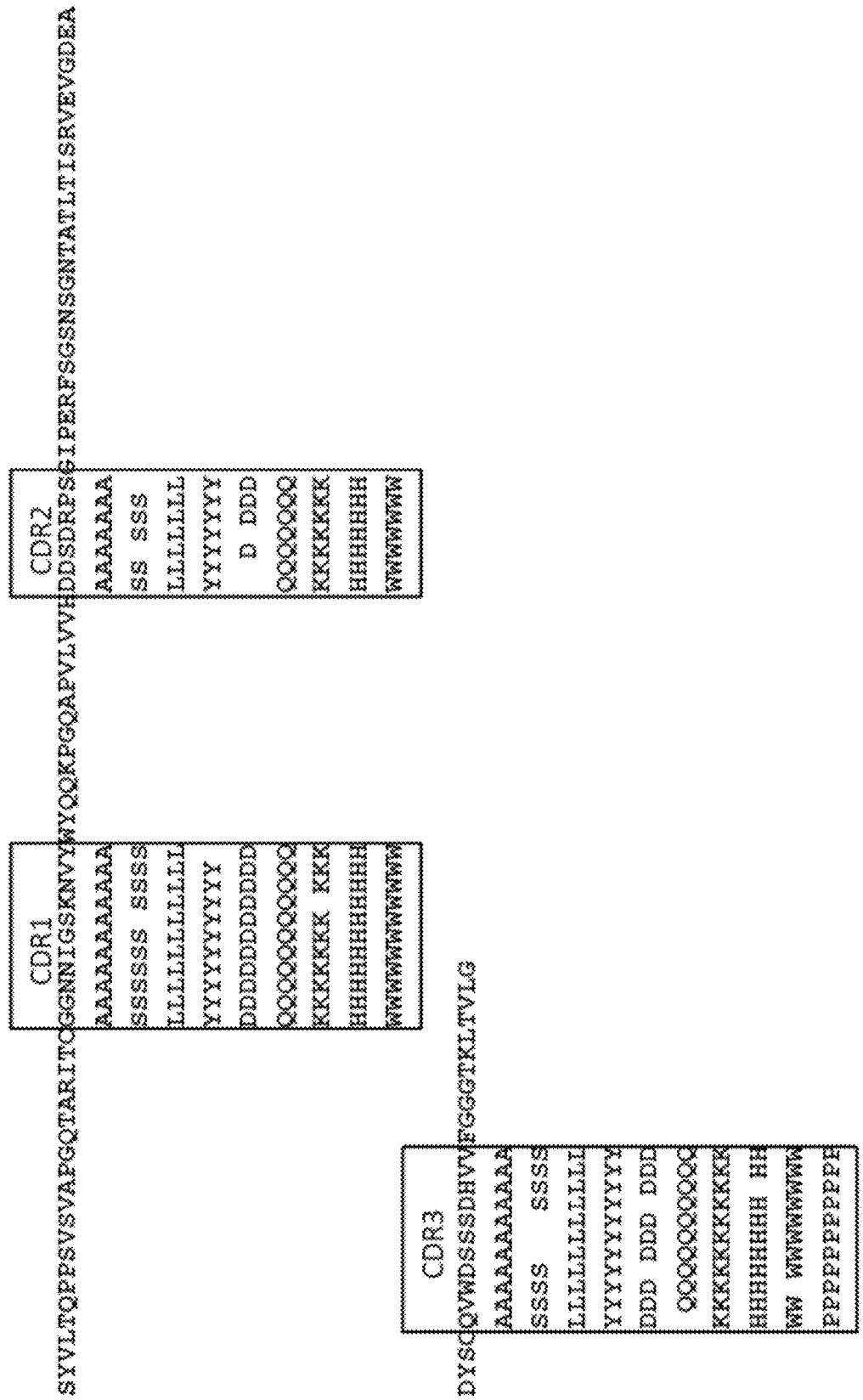
FIG. 4 is graphical matrix showing the position and identity of the different single amino acid substitutions that were generated to the 3A5.040 VL CDRs, aligned to the original 3A5.040 VL sequence (top sequence). The boxes contain the residues which were designated CDR residues according to the AbM nomenclature. The various sequences recited in this figure are provided in SEQ ID NO:74.

CDR Scanning of Antibody 3A5.040
Generation of Antibody 3A5.040 Variants—
Single-mutant variants of antibody 3A5.040 were made by substituting one of a group of nine representative amino acids—A, S, L, Y, D, Q, K, H, W—at each amino acid position in the light chain CDR1 (CDR-L1), the light chain CDR2 (CDR-L2), the heavy chain CDR1 (CDR-H1) and the heavy chain CDR2 (CDR-H2) (as defined by AbM nomenclature). Antibody variants were also made by substituting one of a group of ten representative amino acids—A, S, L, Y, D, Q, K, H, W, P—at each CDR amino acid position in the light chain CDR3 (CDR-L3), heavy chain CDR3 (CDR-H3), and at Kabat positions 93 and 94 in the variable heavy chain. A complete list of all single-mutant antibody variants generated is shown in FIG. 3 (variable heavy chain) and FIG. 4 (variable light chain), respectively.

Construction of Vectors Expressing Antibodies—
Variable region variants were generated by back-translation of amino acid sequences into DNA sequences which were subsequently synthesized de novo by assembly of synthetic oligonucleotides. Variable heavy (VH) variants were subcloned into a mammalian expression vector containing a human constant region to produce full-length antibody heavy chains (human IgG4 heavy chain CH1, hinge, CH2, and CH3 domains). Similarly, variable light (VL) variants were subcloned into a mammalian expression vector containing a human lambda light chain constant region to produce full-length antibody lambda chains.

Expression of Antibody Variants—

Antibodies were produced by co-transfecting separate expression vectors encoding antibody heavy chains and light chains into EXPI293® cells (Life Technologies, Carlsbad, Calif.). Each single-mutant chain was paired with a parental chain for protein expression in the EXPI293® system. For each 20 mL transfection, 3.6×10' cells were required in 20 mL of EXPI293® Expression Medium. On the day prior to transfection, cells were seeded at a density of $0.9 \times 10^6$ viable cells/mL and incubated overnight at 37° C. in a humidified atmosphere of 8% $CO_2$ in air on an orbital shaker rotating at 200 rpm. On the day of transfection, the cell number and viability were determined using an automated cell counter. Only cultures with >98% viable cells were used. For each 20 mL transfection, lipid-DNA complexes were prepared by diluting 10 µg of heavy chain DNA and 10 µg of light chain DNA in OPTI-MEM® (Life Technologies, Carlsbad, Calif.) I Reduced Serum Medium (Cat. no. 31985-062) to a total volume of 1.0 mL. 54 µL of EXPIFECTAMINE® 293 Reagent (Life Technologies, Carlsbad, Calif.) was diluted in OPTI-MEM® I medium to a total volume of 1.0 mL. Both vials were mixed gently and incubated for 5 minutes at room temperature. Following incubation, the diluted DNA was mixed with the diluted EXPIFECTAMINE® 293 Reagent and the DNA-EXPIFECTAMINE® 293 Reagent mixture and incubated a further 20 minutes at room temperature to allow the formation of DNA-EXPIFECTAMINE® 293 Reagent complexes. Following incubation, 2 mL of DNA-EXPIFECTAMINE® 293 Reagent complex was added to each 50 mL bioreactor tube (TPP Techno Plastic Products AG). 2 mL of OPTI-MEM® (Life Technologies, Carlsbad, Calif.) I medium was added to the negative control tube instead of DNA-EXPIFECTAMINE® 293 Reagent complex. The cells were incubated in a 37° C. incubator with a humidified atmosphere of 8% $CO_2$ in air on an orbital shaker rotating at 200 rpm. Approximately 16-18 hours post-transfection, 100 µL of EXPIFECTAMINE® 293 Transfection Enhancer 1 and 1.0 mL of EXPIFECTAMINE® 293 Transfection Enhancer 2 were added to each bioreactor. Supernatants were harvested at approximately 48 hours post-transfection.

Purification of Antibody Variants—

Each antibody variant was expressed in EXPI293® cells in either 20 or 100 mL of cell culture. Cultures were spun down in 50 mL falcon tubes at 3000×g for 20 minutes, and supernatants were filtered using a 0.22 m filter. Supernatants were purified using a Gilson ASPEC GX274 robot. Briefly, SPE cartridges (Agilent, 12131014) packed with 1.2 mL MABSELECT SURE® protein A resin (GE Healthcare) were pre-equilibrated with 3 column volumes of 1×PBS. Supernatant was run over the columns followed by a 4 mL 1×PBS wash. Each column was washed with 9 mL of 1 M citric acid, pH 2.9. Antibodies were eluted with 2 mL 0.1 M citric acid, pH 2.9. Antibodies were desalted into Sørensens PBS (5 mM $KH_2PO_4$, 3 mM $Na_2HPO_4.2H_2O$, 145.4 mM NaCl (pH ~5.8)) using PD-10 columns (GE Healthcare).

Determination of 3A5.040 Variant Antibody Titre in Supernatant by Biacore—Supernatants containing antibody from expression in EXPI293® cells were analyzed using a Protein A series S chip on the Biacore T200 to determine their titre and rank them with respect to the parental antibody 3A5.040. Each supernatant sample was diluted with running buffer (1×HBS-EP+, 350 mM NaCl) and captured by injection at 60 µL/min onto flow cell (FC) 2. The resulting capture level in response units (RUs) were measured on FC 2-1 by subtracting a report point 5 sec after cycle start from one 5 sec after injection. The surface was regenerated by injecting 50 mM NaOH for 12 sec at a flow rate of 60 µL/min onto FC 1 and 2 every 4 cycles. After each regeneration, the surface and sensorgram was stabilized for 120 sec by injection of running buffer. Multiple batches were run due to the large number of antibodies that were screened in this manner.

The capture levels (in Biacore response units "RU") obtained for each supernatant sample were adjusted by multiplying the values obtained for each 30 sec injection by the supernatant dilution factor, enabling comparison of capture levels between supernatants diluted to varying degrees across different experimental runs. The relative antibody expression level (titre) of each mutant was compared to a batch-specific 3A5.040 supernatant, (Table 3) using the following formula:

(adjusted 3A5.040 reference RU for 30 sec injection/ adjusted variant antibody RU for 30 sec injection)×100=proportional titre of parental antibody (% 3A5.040 titre)    Formula 1

Variant antibodies with a higher titre than parent 3A5.040 antibody had a "% 3A5.040 titre" value >100% and those with a lower titre, a value <100%. This enabled the identification of variant antibodies that might have improved expression over the parental antibody, 3A5.040. The titres of some variants were not determined by Biacore analysis of supernatant samples, but were expressed and purified as above and their purified yields determined by spectrophotometric analysis ($A_{280}$), then compared to parental 3A5.040 antibody (Table 5).

Determination of 3A5.040 Variant Antibody IL-5-Binding Kinetics by Biacore—Supernatants containing antibody from expression in EXPI293® cells or purified antibodies were analyzed using a Protein A series S chip on a Biacore T200 system (GE Healthcare) to determine their binding affinity for recombinant human IL-5 and rank them with respect to the parental antibody 3A5.040.

Each antibody was diluted in running buffer (1×HBS-EP+, 350 mM NaCl) and captured at 60 µL/min to approximately 50 RU on FC 2. The surface and sensorgram was then stabilized for 120 sec by injection of running buffer. Recombinant human IL-5 at 5 g/mL or running buffer was injected onto FC 1 and 2 at a flow rate of 60 µL/min for 70 sec. The IL-5 was allowed to dissociate in running buffer for 300 sec. The surface was regenerated by injecting 50 mM NaOH for 12 sec at a flow rate of 60 µL/min onto FC 1 and 2. Buffer was injected to further clean up drift for 60 sec at a flow rate of 60 µL/min onto FC 1 and 2. The surface was stabilized for 300 sec with running buffer over FC 1 and 2. Supernatant containing the parental 3A5.040 antibody and that had been transfected with each batch was run approximately every 25 cycles throughout each run. A purified sample of 3A5.040 and an IgG4 lambda isotype control was run with every batch as a measure of inter-assay variability. Multiple batches were run due to the large number of antibodies that were screened in this manner.

Data was double-referenced (flow cell 2 was subtracted from flow cell 1 and a buffer blank) and sensorgrams fitted to a 1:1 Langmuir binding model with Biacore Evaluation software. A kd (off-rate) value was calculated for each 3A5.040 supernatant sample throughout the run and these were averaged to give a reference kd, with the exception of run 2.1, which only had one 3A5.040 supernatant sample (Table 3 and Tables 6-11). The calculated kd value for each supernatant antibody was compared against the 3A5.040 average reference kd using the following formula:

(3A5.040 reference kd/variant antibody kd)× 100=proportional kd of parental antibody (% 3A5.040 kd)  Formula 2

Variant antibodies with a lower kd (slower off-rate) than parent 3A5.040 antibody had a "% 3A5.040 kd" value >100% and those with a higher kd (faster off-rate) a value <100%. This enabled the identification of variant antibodies that might have improved binding kinetics for IL-5 and therefore improved function over the parental antibody, 3A5.040. For variants where only purified protein was made (Table 6), the Biacore kinetic analysis was performed in triplicate as above using these purified antibodies and the average values from each triplicate analysis used to perform the proportional kd calculation, as above (Table 4 and Tables 8-11).

TABLE 3

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 1.1 | 3A5.040 | 1 | Wild type | 51.6 | 7.20E+05 | 1.15E−04 | 1.60E−10 | 16.3 | | |
| 1.1 | 3A5.040 | 2 | Wild type | 51.6 | 7.27E+05 | 8.96E−05 | 1.23E−10 | 16.6 | | |
| 1.1 | 3A5.040 | 3 | Wild type | 51.8 | 7.18E+05 | 9.21E−05 | 1.28E−10 | 16.7 | | |
| 1.1 | 3A5.040 | 4 | Wild type | 52 | 6.96E+05 | 9.95E−05 | 1.43E−10 | 16.8 | | |
| 1.1 | 3A5.040 | Average | Wild type | 51.75 | 7.15E+05 | 9.91E−05 | 1.39E−10 | 16.6 | 100 | 100 |
| 1.1 | IgG4 Isotype | | | 54.4 | N/A | N/A | N/A | 0.7 | N/A | N/A |
| 1.1 | 3A5.040 (Purified) | | Wild type | 56.4 | 7.17E+05 | 1.06E−04 | 1.48E−10 | 17.8 | 93.0 | |
| 1.1 | 3A5.304 | | VH_G26A | 54.6 | 7.41E+05 | 7.73E−05 | 1.04E−10 | 17.1 | 128 | 49 |
| 1.1 | 3A5.305 | | VH_G26S | 53.1 | 7.36E+05 | 1.09E−04 | 1.48E−10 | 16.7 | 91 | 59 |
| 1.1 | 3A5.306 | | VH_G26L | 49.1 | 7.49E+05 | 8.74E−05 | 1.17E−10 | 15.6 | 113 | 15 |
| 1.1 | 3A5.308 | | VH_G26D | 52.5 | 6.75E+05 | 8.57E−05 | 1.27E−10 | 16.4 | 116 | 61 |
| 1.1 | 3A5.309 | | VH_G26Q | 55.1 | 7.47E+05 | 9.23E−05 | 1.24E−10 | 17.4 | 107 | 86 |
| 1.1 | 3A5.310 | | VH_G26K | 51.8 | 7.36E+05 | 1.01E−04 | 1.37E−10 | 16.4 | 98 | 100 |
| 1.1 | 3A5.311 | | VH_G26H | 50.9 | 7.60E+05 | 1.11E−04 | 1.46E−10 | 16.3 | 89 | 85 |
| 1.1 | 3A5.312 | | VH_G26W | 56.1 | 8.54E+05 | 1.21E−04 | 1.41E−10 | 18 | 82 | 107 |
| 1.1 | 3A5.313 | | VH_G27A | 54.5 | 6.97E+05 | 1.17E−04 | 1.68E−10 | 17.3 | 85 | 99 |
| 1.1 | 3A5.314 | | VH_G27S | 50.9 | 7.16E+05 | 9.81E−05 | 1.37E−10 | 16.2 | 101 | 95 |
| 1.1 | 3A5.315 | | VH_G27L | 54.3 | 7.01E+05 | 1.31E−04 | 1.87E−10 | 17.1 | 76 | 118 |
| 1.1 | 3A5.316 | | VH_G27Y | 56 | 6.66E+05 | 8.56E−04 | 1.29E−09 | 16.9 | 12 | 80 |
| 1.1 | 3A5.317 | | VH_G27D | 57.4 | 6.56E+05 | 1.16E−04 | 1.76E−10 | 17.8 | 85 | 73 |
| 1.1 | 3A5.318 | | VH_G27Q | 55.2 | 7.31E+05 | 1.49E−04 | 2.04E−10 | 17.4 | 67 | 82 |
| 1.1 | 3A5.319 | | VH_G27K | 54.8 | 7.70E+05 | 2.04E−04 | 2.65E−10 | 17.5 | 49 | 95 |
| 1.1 | 3A5.320 | | VH_G27H | 54.4 | 7.12E+05 | 2.43E−04 | 3.42E−10 | 16.9 | 41 | 71 |
| 1.1 | 3A5.322 | | VH_S28A | 58 | 7.49E+05 | 1.05E−04 | 1.41E−10 | 18 | 94 | 62 |
| 1.1 | 3A5.323 | | VH_S28L | 53.8 | 7.18E+05 | 9.30E−05 | 1.30E−10 | 17 | 107 | 70 |
| 1.1 | 3A5.324 | | VH_S28Y | 54.8 | 8.13E+05 | 8.60E−05 | 1.06E−10 | 17 | 115 | 51 |
| 1.1 | 3A5.325 | | VH_S28D | 54.9 | 6.03E+05 | 9.16E−05 | 1.52E−10 | 17 | 108 | 68 |
| 1.1 | 3A5.326 | | VH_S28Q | 56.9 | 6.78E+05 | 9.97E−05 | 1.47E−10 | 17.7 | 99 | 77 |
| 1.1 | 3A5.327 | | VH_S28K | 53.7 | 7.22E+05 | 1.15E−04 | 1.59E−10 | 16.9 | 86 | 84 |
| 1.1 | 3A5.328 | | VH_S28H | 54 | 7.82E+05 | 1.23E−04 | 1.57E−10 | 16.9 | 81 | 71 |
| 1.1 | 3A5.329 | | VH_S28W | 55 | 8.33E+05 | 1.36E−04 | 1.63E−10 | 17 | 73 | 41 |
| 1.1 | 3A5.330 | | VH_I29A | 56.3 | 6.54E+05 | 1.69E−04 | 2.58E−10 | 16.8 | 59 | 30 |
| 1.1 | 3A5.331 | | VH_I29S | 53.3 | 5.87E+05 | 2.04E−04 | 3.48E−10 | 15.7 | 49 | 28 |
| 1.1 | 3A5.332 | | VH_I29L | 55.3 | 8.26E+05 | 1.16E−04 | 1.41E−10 | 17.5 | 85 | 75 |
| 1.1 | 3A5.333 | | VH_I29Y | 55.4 | 5.44E+05 | 9.31E−04 | 1.71E−09 | 15.7 | 11 | 24 |
| 1.1 | 3A5.334 | | VH_I29D | 52.8 | 3.53E+06 | 5.37E−03 | 1.52E−09 | 11.9 | 2 | 21 |
| 1.1 | 3A5.336 | | VH_I29K | 53.7 | 6.17E+05 | 6.75E−04 | 1.10E−09 | 14.8 | 15 | 29 |
| 1.1 | 3A5.338 | | VH_I29W | 56.6 | 1.31E+06 | 2.34E−03 | 1.78E−09 | 14.9 | 4 | 38 |
| 1.1 | 3A5.340 | | VH_S30L | 48.7 | 6.51E+05 | 1.47E−04 | 2.25E−10 | 15.6 | 67 | 153 |
| 1.1 | 3A5.341 | | VH_S30Y | 54.3 | 7.54E+05 | 1.37E−04 | 1.82E−10 | 17.3 | 72 | 103 |
| 1.1 | 3A5.342 | | VH_S30D | 54.9 | 6.17E+05 | 1.23E−04 | 2.00E−10 | 17.4 | 81 | 103 |
| 1.1 | 3A5.347 | | VH_N31A | 53.8 | 7.53E+05 | 6.75E−04 | 8.97E−10 | 17.3 | 15 | 118 |
| 1.1 | 3A5.348 | | VH_N31S | 54.6 | 7.82E+05 | 5.03E−04 | 6.44E−10 | 17.7 | 20 | 107 |
| 1.1 | 3A5.350 | | VH_N31Y | 56.2 | 9.01E+05 | 8.80E−04 | 9.76E−10 | 17.6 | 11 | NE |
| 1.1 | 3A5.351 | | VH_N31D | 59.8 | 6.40E+05 | 2.03E−04 | 3.17E−10 | 19.2 | 49 | 75 |
| 1.1 | 3A5.352 | | VH_N31Q | 54.8 | 6.93E+05 | 4.21E−04 | 6.07E−10 | 17.7 | 24 | 156 |
| 1.1 | 3A5.353 | | VH_N31K | 55.5 | 6.85E+05 | 7.54E−04 | 1.10E−09 | 17.7 | 13 | 170 |
| 1.1 | 3A5.354 | | VH_N31H | 53.7 | 7.63E+05 | 1.32E−04 | 1.73E−10 | 17.5 | 75 | 143 |
| 1.1 | 3A5.356 | | VH_G32A | 52.3 | 5.25E+05 | 3.02E−04 | 5.76E−10 | 16.4 | 33 | 179 |
| 1.1 | 3A5.357 | | VH_G32S | 49.2 | 6.02E+05 | 1.23E−03 | 2.04E−09 | 15.3 | 8 | 153 |
| 1.1 | 3A5.495 | | VH_S94K | 55 | 6.76E+05 | 2.91E−04 | 4.31E−10 | 17.6 | 34 | 127 |
| 1.1 | 3A5.497 | | VH_S94W | 56.8 | 1.67E+06 | 2.92E−03 | 1.75E−09 | 12.5 | 3 | 38 |
| 1.1 | 3A5.498 | | VH_S94P | 55.5 | 4.45E+05 | 1.17E−04 | 2.63E−10 | 16 | 85 | 17 |
| 1.1 | 3A5.500 | | VH_L95S | 2.7 | | | | | NE | NE |
| 1.1 | 3A5.504 | | VH_L95K | 51.7 | 1.53E+06 | 3.12E−03 | 2.03E−09 | 11.3 | 3 | 67 |
| 1.1 | 3A5.505 | | VH_L95H | 52.9 | 5.59E+05 | 6.66E−04 | 1.19E−09 | 16.3 | 15 | 88 |
| 1.1 | 3A5.507 | | VH_L95P | 54.7 | | | | | NB | 40 |
| 1.1 | 3A5.509 | | VH_G96S | 54.4 | 5.94E+05 | 1.92E−04 | 3.23E−10 | 17 | 52 | 88 |
| 1.1 | 3A5.510 | | VH_G96L | 54 | 4.11E+06 | 7.90E−03 | 1.92E−09 | 8.5 | 1 | 63 |
| 1.1 | 3A5.513 | | VH_G96Q | 54.8 | 4.45E+05 | 5.13E−04 | 1.15E−09 | 16.5 | 19 | 64 |
| 1.1 | 3A5.514 | | VH_G96K | 54.9 | 5.14E+06 | 6.84E−03 | 1.33E−09 | 11.4 | 1 | 147 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 1.1 | 3A5.515 | | VH_G96H | 53.2 | 4.37E+05 | 1.20E-03 | 2.74E-09 | 15.3 | 8 | 117 |
| 1.1 | 3A5.516 | | VH_G96W | 53 | 1.31E+06 | 1.40E-02 | 1.07E-08 | 6.7 | 1 | 55 |
| 1.1 | 3A5.517 | | VH_G96P | 47.8 | 1.35E+06 | 5.04E-04 | 3.73E-09 | 11.7 | 20 | 15 |
| 1.1 | 3A5.518 | | VH_N97A | 52 | 5.35E+05 | 1.72E-04 | 3.21E-10 | 16.3 | 58 | 95 |
| 1.1 | 3A5.520 | | VH_N97L | 54.5 | 4.73E+05 | 1.11E-04 | 2.35E-10 | 16 | 89 | 96 |
| 1.1 | 3A5.521 | | VH_N97Y | 54.7 | 5.05E+05 | 3.34E-04 | 6.62E-10 | 16.1 | 30 | 75 |
| 1.1 | 3A5.523 | | VH_N97Q | 53.7 | 5.06E+05 | 9.79E-05 | 1.94E-10 | 16.6 | 101 | 127 |
| 1.1 | 3A5.524 | | VH_N97K | 52.5 | 2.89E+05 | 1.37E-04 | 4.75E-10 | 15.1 | 72 | 167 |
| 1.1 | 3A5.525 | | VH_N97H | 53.1 | 4.11E+05 | 2.14E-04 | 5.20E-10 | 15 | 46 | 113 |
| 1.1 | 3A5.526 | | VH_N97W | 53.7 | 5.28E+05 | 5.26E-04 | 9.95E-10 | 15.5 | 19 | 56 |
| 1.1 | 3A5.527 | | VH_N97P | 55.1 | 4.21E+05 | 4.38E-04 | 1.04E-09 | 15.5 | 23 | 68 |
| 1.1 | 3A5.528 | | VH_W98A | 57.6 | 7.26E+05 | 1.87E-04 | 2.57E-10 | 18.4 | 53 | 114 |
| 1.1 | 3A5.529 | | VH_W98S | 53.9 | 6.23E+05 | 2.36E-04 | 3.78E-10 | 16.8 | 42 | 83 |
| 1.1 | 3A5.530 | | VH_W98L | 54.3 | 3.38E+05 | 1.72E-04 | 5.08E-10 | 14.9 | 58 | 38 |
| 1.1 | 3A5.531 | | VH_W98Y | 56.3 | 7.15E+05 | 1.12E-04 | 1.56E-10 | 18.1 | 88 | 143 |
| 1.1 | 3A5.532 | | VH_W98D | 56.4 | 2.17E+05 | 8.87E-05 | 4.09E-10 | 14.6 | 112 | 42 |
| 1.1 | 3A5.533 | | VH_W98Q | 53.8 | 5.01E+05 | 1.54E-04 | 3.08E-10 | 15.8 | 64 | 51 |
| 1.1 | 3A5.534 | | VH_W98K | 53.4 | 3.46E+05 | 8.25E-04 | 2.38E-09 | 11.5 | 12 | 73 |
| 1.1 | 3A5.535 | | VH_W98H | 53.8 | 6.13E+05 | 1.45E-04 | 2.37E-10 | 17 | 68 | 81 |
| 1.1 | 3A5.536 | | VH_W98P | 56.1 | 9.97E+04 | 8.17E-04 | 8.20E-09 | 14.2 | 12 | 31 |
| 1.1 | 3A5.537 | | VH_F99A | 54.2 | 1.54E+05 | 4.90E-04 | 3.18E-09 | 13.7 | 20 | 37 |
| 1.1 | 3A5.538 | | VH_F99S | 53.3 | 1.18E+05 | 1.02E-03 | 8.67E-09 | 9.9 | 10 | 40 |
| 1.1 | 3A5.539 | | VH_F99L | 54.2 | 7.05E+05 | 1.15E-04 | 1.63E-10 | 16.7 | 86 | 55 |
| 1.1 | 3A5.540 | | VH_F99Y | 55.6 | 5.27E+05 | 9.13E-05 | 1.73E-10 | 14.9 | 109 | 41 |
| 1.1 | 3A5.541 | | VH_F99D | 53.9 | 1.46E+05 | 1.11E-02 | 7.56E-08 | 4.4 | 1 | 32 |
| 1.1 | 3A5.542 | | VH_F99Q | 53.8 | 9.93E+04 | 1.00E-03 | 1.01E-08 | 13 | 10 | 35 |
| 1.1 | 3A5.543 | | VH_F99K | 54.6 | | | | | NB | 38 |
| 1.1 | 3A5.544 | | VH_F99H | 54.8 | 2.05E+05 | 9.50E-05 | 4.64E-10 | 14.5 | 104 | 41 |
| 1.1 | 3A5.545 | | VH_F99W | 54.5 | 5.35E+04 | 4.09E-04 | 7.66E-09 | 6 | 24 | 29 |
| 1.1 | 3A5.546 | | VH_F99P | 53.1 | | | | | NB | 43 |
| 1.1 | 3A5.547 | | VH_D101A | 55.6 | 1.68E+05 | 1.40E-04 | 8.37E-10 | 14.7 | 71 | 69 |
| 1.1 | 3A5.548 | | VH_D101S | 55.2 | 2.38E+05 | 1.11E-04 | 4.67E-10 | 15.3 | 89 | 78 |
| 1.1 | 3A5.549 | | VH_D101L | 53.6 | 5.94E+05 | 4.76E-04 | 8.01E-10 | 16.3 | 21 | 43 |
| 1.1 | 3A5.551 | | VH_D101Q | 54.5 | 5.93E+05 | 2.19E-04 | 3.69E-10 | 17.1 | 45 | 78 |
| 1.2 | 3A5.040 | 1 | Wild type | 50.3 | 7.40E+05 | 1.33E-04 | 1.80E-10 | 16.3 | | |
| 1.2 | 3A5.040 | 2 | Wild type | 50.3 | 7.14E+05 | 8.22E-05 | 1.15E-10 | 16.1 | | |
| 1.2 | 3A5.040 | 3 | Wild type | 50 | 7.28E+05 | 1.01E-04 | 1.39E-10 | 16.1 | | |
| 1.2 | 3A5.040 | 4 | Wild type | 50.2 | 7.32E+05 | 1.10E-04 | 1.50E-10 | 16.2 | | |
| 1.2 | 3A5.040 | 5 | Wild type | 50.1 | 7.27E+05 | 9.36E-05 | 1.29E-10 | 16.1 | | |
| 1.2 | 3A5.040 | Average | Wild type | 50.2 | 7.28E+05 | 1.04E-04 | 1.43E-10 | 16.2 | 100 | 100 |
| 1.2 | IgG4 Isotype | | | 50.8 | N/A | N/A | N/A | 0 | N/A | |
| 1.2 | 3A5.040 (Purified) | | Wild type | 52.6 | 7.35E+05 | 1.11E-04 | 1.51E-10 | 16.6 | 94 | |
| 1.2 | 3A5.553 | | VH_D101H | 51.9 | 4.41E+05 | 1.63E-04 | 3.69E-10 | 15.5 | 64 | 66 |
| 1.2 | 3A5.555 | | VH_D101P | 51.3 | 7.54E+03 | 8.00E-04 | 1.06E-07 | 23.6 | 13 | 39 |
| 1.2 | 3A5.556 | | VH_Y102A | 50.6 | 6.60E+05 | 8.94E-05 | 1.35E-10 | 16.4 | 116 | 106 |
| 1.2 | 3A5.557 | | VH_Y102S | 53.5 | 6.85E+05 | 1.11E-04 | 1.61E-10 | 17.2 | 94 | 135 |
| 1.2 | 3A5.558 | | VH_Y102L | 53.2 | 7.40E+05 | 1.14E-04 | 1.54E-10 | 16.8 | 91 | 51 |
| 1.2 | 3A5.559 | | VH_Y102D | 52.8 | 7.03E+05 | 1.41E-04 | 2.01E-10 | 16.7 | 74 | 51 |
| 1.2 | 3A5.560 | | VH_Y102Q | 52.6 | 7.14E+05 | 1.08E-04 | 1.51E-10 | 16.9 | 96 | 87 |
| 1.2 | 3A5.561 | | VH_Y102K | 55.9 | 7.23E+05 | 8.01E-05 | 1.11E-10 | 17.7 | 130 | 90 |
| 1.2 | 3A5.562 | | VH_Y102H | 50.4 | 7.22E+05 | 1.00E-04 | 1.39E-10 | 16.4 | 104 | 132 |
| 1.2 | 3A5.563 | | VH_Y102W | 50.9 | 7.51E+05 | 1.16E-04 | 1.54E-10 | 16.8 | 90 | 117 |
| 1.2 | 3A5.564 | | VH_Y102P | 53 | 6.44E+05 | 1.29E-04 | 2.01E-10 | 15 | 81 | 32 |
| 2.1 | 3A5.040 | 1 | Wild type | 68.5 | 7.13E+05 | 1.16E-04 | 1.63E-10 | 22.6 | | |
| 2.1 | 3A5.040 | Average | Wild type | 68.5 | 7.13E+05 | 1.16E-04 | 1.63E-10 | 22.6 | 100 | 100 |
| 2.1 | IgG4 Isotype | | | 60.7 | N/A | N/A | N/A | 1.6 | N/A | |
| 2.1 | 3A5.040 (Purified) | | Wild type | 75.6 | 7.37E+05 | 1.05E-04 | 1.42E-10 | 24.3 | 110 | |
| 2.1 | 3A5.048 | | VL_G24A | 69 | 7.16E+05 | 9.18E-05 | 1.28E-10 | 22.7 | 126 | 104 |
| 2.1 | 3A5.049 | | VL_G24S | 72.5 | 6.98E+05 | 1.02E-04 | 1.47E-10 | 23.7 | 113 | 104 |
| 2.1 | 3A5.050 | | VL_G24L | 73.8 | 6.79E+05 | 8.13E-05 | 1.20E-10 | 23.9 | 143 | 103 |
| 2.1 | 3A5.051 | | VL_G24Y | 61.7 | 6.40E+05 | 1.12E-04 | 1.75E-10 | 20.3 | 104 | 91 |
| 2.1 | 3A5.052 | | VL_G24D | 66.7 | 7.16E+05 | 9.71E-05 | 1.36E-10 | 21.9 | 119 | 104 |
| 2.1 | 3A5.053 | | VL_G24Q | 72.6 | 6.99E+05 | 9.84E-05 | 1.41E-10 | 23.6 | 118 | 95 |
| 2.1 | 3A5.054 | | VL_G24K | 74.2 | 7.12E+05 | 9.59E-05 | 1.35E-10 | 24.1 | 121 | 98 |
| 2.1 | 3A5.055 | | VL_G24H | 60.9 | 6.90E+05 | 9.17E-05 | 1.33E-10 | 20.2 | 126 | 99 |
| 2.1 | 3A5.056 | | VL_G24W | 64.4 | 6.41E+05 | 8.06E-05 | 1.26E-10 | 21.1 | 144 | 111 |
| 2.1 | 3A5.057 | | VL_G25A | 69.9 | 7.04E+05 | 8.75E-05 | 1.24E-10 | 22.9 | 133 | 109 |
| 2.1 | 3A5.059 | | VL_G25L | 63.1 | 7.16E+05 | 1.04E-04 | 1.45E-10 | 21 | 112 | 83 |
| 2.1 | 3A5.060 | | VL_G25Y | 67.7 | 7.05E+05 | 8.55E-05 | 1.21E-10 | 22.2 | 136 | 96 |
| 2.1 | 3A5.061 | | VL_G25D | 71.9 | 7.26E+05 | 1.11E-04 | 1.53E-10 | 23.4 | 105 | 94 |
| 2.1 | 3A5.062 | | VL_G25Q | 73.2 | 6.52E+05 | 9.24E-05 | 1.42E-10 | 23.5 | 126 | 94 |
| 2.1 | 3A5.064 | | VL_G25H | 60.4 | 6.90E+05 | 9.21E-05 | 1.33E-10 | 20.1 | 126 | 108 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 2.1 | 3A5.065 | | VL_G25W | 70.8 | 7.37E+05 | 8.97E−05 | 1.22E−10 | 23.1 | 129 | 81 |
| 2.1 | 3A5.066 | | VL_N26A | 76.8 | 7.27E+05 | 8.75E−05 | 1.20E−10 | 24.7 | 133 | 77 |
| 2.1 | 3A5.069 | | VL_N26Y | 71.2 | 6.79E+05 | 8.73E−05 | 1.28E−10 | 22.9 | 133 | 100 |
| 2.1 | 3A5.070 | | VL_N26D | 62.7 | 7.22E+05 | 7.87E−05 | 1.09E−10 | 20.7 | 147 | 95 |
| 2.1 | 3A5.071 | | VL_N26Q | 67.4 | 7.05E+05 | 1.08E−04 | 1.53E−10 | 22 | 107 | 95 |
| 2.1 | 3A5.072 | | VL_N26K | 69.7 | 7.04E+05 | 1.17E−04 | 1.66E−10 | 22.7 | 99 | 99 |
| 2.1 | 3A5.073 | | VL_N26H | 74.8 | 7.15E+05 | 1.11E−04 | 1.55E−10 | 24 | 105 | 95 |
| 2.1 | 3A5.074 | | VL_N26W | 62.6 | 6.41E+05 | 9.82E−05 | 1.53E−10 | 20.3 | 118 | 87 |
| 2.1 | 3A5.075 | | VL_N27A | 62.7 | 6.55E+05 | 9.29E−05 | 1.42E−10 | 20.7 | 125 | 120 |
| 2.1 | 3A5.076 | | VL_N27S | 71.7 | 7.04E+05 | 1.09E−04 | 1.55E−10 | 23.2 | 106 | 93 |
| 2.1 | 3A5.077 | | VL_N27L | 71.7 | 6.73E+05 | 8.98E−05 | 1.33E−10 | 23.4 | 129 | 102 |
| 2.1 | 3A5.078 | | VL_N27Y | 61.5 | 6.16E+05 | 1.02E−04 | 1.65E−10 | 20.3 | 114 | 103 |
| 2.1 | 3A5.080 | | VL_N27Q | 68.3 | 6.52E+05 | 1.07E−04 | 1.64E−10 | 22.1 | 108 | 91 |
| 2.1 | 3A5.081 | | VL_N27K | 71.5 | 6.89E+05 | 8.84E−05 | 1.28E−10 | 23.2 | 131 | 96 |
| 2.1 | 3A5.082 | | VL_N27H | 74.7 | 7.06E+05 | 7.85E−05 | 1.11E−10 | 24.1 | 148 | 90 |
| 2.1 | 3A5.084 | | VL_I28A | 62.1 | 6.71E+05 | 6.20E−05 | 9.24E−11 | 20.3 | 187 | 91 |
| 2.1 | 3A5.085 | | VL_I28S | 91.9 | 6.37E+05 | 1.16E−04 | 1.82E−10 | 31.3 | 100 | 47 |
| 2.1 | 3A5.086 | | VL_I28L | 81.5 | 6.02E+05 | 1.04E−04 | 1.73E−10 | 27.2 | 112 | 62 |
| 2.1 | 3A5.087 | | VL_I28Y | 73.1 | 7.07E+05 | 8.52E−05 | 1.20E−10 | 23.8 | 136 | 93 |
| 2.1 | 3A5.088 | | VL_I28D | 80.3 | 5.56E+05 | 9.83E−05 | 1.77E−10 | 27.9 | 118 | 40 |
| 2.1 | 3A5.089 | | VL_I28Q | 79.8 | 5.80E+05 | 1.03E−04 | 1.77E−10 | 27.8 | 113 | 54 |
| 2.1 | 3A5.093 | | VL_G29A | 68.4 | 5.42E+05 | 1.10E−04 | 2.04E−10 | 22.6 | 105 | 59 |
| 2.1 | 3A5.094 | | VL_G29S | 67.6 | 6.98E+05 | 9.31E−05 | 1.33E−10 | 21.9 | 119 | 93 |
| 2.2 | 3A5.040 | 1 | Wild type | 52.4 | 7.77E+05 | 1.05E−04 | 1.35E−10 | 17.9 | | |
| 2.2 | 3A5.040 | 2 | Wild type | 52.7 | 7.89E+05 | 1.09E−04 | 1.38E−10 | 17.9 | | |
| 2.2 | 3A5.040 | 3 | Wild type | 52.7 | 7.72E+05 | 1.37E−04 | 1.77E−10 | 18.1 | | |
| 2.2 | 3A5.040 | Average | Wild type | 52.6 | 7.79E+05 | 1.17E−04 | 1.50E−10 | 17.9 | 100 | 100 |
| 2.2 | IgG4 Isotype | | | 56.6 | N/A | N/A | N/A | 0.5 | N/A | |
| 2.2 | 3A5.040 (Purified) | | Wild type | 54.9 | 7.93E+05 | 1.06E−04 | 1.33E−10 | 18.7 | 110 | |
| 2.2 | 3A5.095 | | VL_G29L | 55.4 | 7.17E+05 | 9.08E−05 | 1.27E−10 | 18.7 | 122 | 75 |
| 2.2 | 3A5.096 | | VL_G29Y | 56.7 | 6.92E+05 | 1.33E−04 | 1.92E−10 | 19.2 | 83 | 58 |
| 2.2 | 3A5.097 | | VL_G29D | 56.2 | 7.31E+05 | 7.19E−05 | 9.84E−11 | 18.7 | 154 | 85 |
| 2.2 | 3A5.099 | | VL_G29K | 49.9 | 7.18E+05 | 9.08E−05 | 1.26E−10 | 17.2 | 122 | 71 |
| 2.2 | 3A5.100 | | VL_G29H | 52 | 7.38E+05 | 8.65E−05 | 1.17E−10 | 17.7 | 128 | 100 |
| 2.2 | 3A5.101 | | VL_G29W | 55.8 | 7.59E+05 | 9.40E−05 | 1.24E−10 | 18.7 | 118 | 114 |
| 2.2 | 3A5.102 | | VL_S30A | 56.3 | 6.85E+05 | 1.09E−04 | 1.58E−10 | 18.7 | 102 | 84 |
| 2.2 | 3A5.103 | | VL_S30L | 49.5 | 7.87E+05 | 9.94E−05 | 1.26E−10 | 16.9 | 112 | 126 |
| 2.2 | 3A5.104 | | VL_S30Y | 54.7 | 8.17E+05 | 1.08E−04 | 1.33E−10 | 18.5 | 103 | 93 |
| 2.2 | 3A5.105 | | VL_S30D | 56.4 | 8.20E+05 | 8.91E−05 | 1.09E−10 | 18.8 | 125 | 119 |
| 2.2 | 3A5.106 | | VL_S30Q | 58.3 | 7.22E+05 | 9.10E−05 | 1.26E−10 | 19.7 | 122 | 78 |
| 2.2 | 3A5.107 | | VL_S30K | 50.6 | 7.85E+05 | 7.34E−05 | 9.34E−11 | 17.3 | 151 | 102 |
| 2.2 | 3A5.113 | | VL_K31Y | 53.8 | 8.35E+05 | 8.73E−05 | 1.05E−10 | 18.4 | 127 | 99 |
| 2.2 | 3A5.114 | | VL_K31D | 54.5 | 4.89E+05 | 4.73E−04 | 9.65E−10 | 17.9 | 23 | 105 |
| 2.2 | 3A5.115 | | VL_K31Q | 57.9 | 4.65E+05 | 4.60E−04 | 9.91E−10 | 19 | 24 | 85 |
| 2.2 | 3A5.116 | | VL_K31H | 49.5 | 5.52E+05 | 2.46E−04 | 4.46E−10 | 16.7 | 45 | 104 |
| 2.2 | 3A5.117 | | VL_K31W | 52.7 | 5.34E+05 | 1.33E−04 | 2.49E−10 | 17.7 | 83 | 125 |
| 2.2 | 3A5.118 | | VL_N32A | 55.8 | 5.07E+05 | 6.39E−04 | 1.26E−09 | 18.3 | 17 | 67 |
| 2.2 | 3A5.121 | | VL_N32Y | 56.1 | 9.57E+05 | 9.68E−05 | 1.01E−10 | 19.1 | 115 | 91 |
| 2.2 | 3A5.122 | | VL_N32D | 49.8 | 5.68E+05 | 1.25E−04 | 2.20E−10 | 15.8 | 89 | 115 |
| 2.2 | 3A5.123 | | VL_N32Q | 53.9 | 8.85E+05 | 1.25E−04 | 1.41E−10 | 18.6 | 89 | 102 |
| 2.2 | 3A5.125 | | VL_N32H | 56.4 | 9.01E+05 | 7.73E−05 | 8.58E−11 | 19.2 | 144 | 90 |
| 2.2 | 3A5.126 | | VL_N32W | 56.6 | 6.35E+05 | 9.26E−05 | 1.46E−10 | 18.8 | 120 | 79 |
| 2.2 | 3A5.127 | | VL_V33A | 49.1 | 7.15E+05 | 8.05E−05 | 1.13E−10 | 16.6 | 138 | 74 |
| 2.2 | 3A5.128 | | VL_V33S | 51.5 | 2.85E+05 | 9.65E−05 | 3.38E−10 | 13.7 | 115 | 126 |
| 2.2 | 3A5.130 | | VL_V33Y | 56.1 | 7.41E+05 | 9.16E−05 | 1.24E−10 | 19 | 121 | 68 |
| 2.2 | 3A5.131 | | VL_V33D | 52.4 | 7.40E+05 | 9.67E−05 | 1.31E−10 | 19.3 | 115 | 40 |
| 2.2 | 3A5.132 | | VL_V33Q | 48.7 | 6.61E+05 | 1.38E−04 | 2.09E−10 | 16.7 | 80 | 50 |
| 2.2 | 3A5.135 | | VL_V33W | 48.4 | 5.26E+05 | 1.04E−04 | 1.99E−10 | 18.8 | 107 | 24 |
| 2.2 | 3A5.137 | | VL_Y34S | 48.3 | 6.96E+05 | 9.88E−05 | 1.42E−10 | 19 | 112 | 32 |
| 2.2 | 3A5.138 | | VL_Y34L | 49.4 | 5.94E+05 | 2.16E−04 | 3.64E−10 | 16.6 | 51 | 56 |
| 2.2 | 3A5.139 | | VL_Y34D | 52.8 | 4.63E+05 | 4.90E−04 | 1.06E−09 | 13.1 | 23 | 68 |
| 2.2 | 3A5.140 | | VL_Y34Q | 54.4 | 7.01E+05 | 5.40E−04 | 7.71E−10 | 18.2 | 21 | 55 |
| 2.2 | 3A5.141 | | VL_Y34K | 56 | 8.16E+05 | 3.72E−04 | 4.56E−10 | 18.8 | 30 | 64 |
| 2.2 | 3A5.142 | | VL_Y34H | 48.8 | 6.71E+05 | 5.00E−04 | 7.46E−10 | 16.3 | 22 | 82 |
| 2.2 | 3A5.143 | | VL_Y34W | 53.5 | 6.98E+05 | 2.19E−03 | 3.13E−09 | 9.7 | 5 | 58 |
| 2.2 | 3A5.165 | | VL_S52K | 52.6 | 5.32E+05 | 9.30E−05 | 1.75E−09 | 16.6 | 12 | 167 |
| 2.2 | 3A5.168 | | VL_D53A | 57.2 | 1.20E+06 | 2.04E−03 | 1.71E−09 | 17.1 | 5 | 51 |
| 2.2 | 3A5.172 | | VL_D53Q | 50.3 | 7.13E+05 | 1.08E−04 | 1.51E−10 | 17.1 | 103 | 97 |
| 2.2 | 3A5.174 | | VL_D53H | 53 | 7.45E+05 | 1.23E−04 | 1.65E−10 | 17.7 | 90 | 120 |
| 2.2 | 3A5.186 | | VL_P55S | 55.8 | 7.97E+05 | 1.08E−04 | 1.35E−10 | 18.6 | 103 | 108 |
| 2.2 | 3A5.199 | | VL_S56K | 57.3 | 7.71E+05 | 1.18E−04 | 1.54E−10 | 18.8 | 94 | 104 |
| 2.2 | 3A5.201 | | VL_S56W | 49.6 | 7.41E+05 | 1.24E−04 | 1.67E−10 | 17.1 | 90 | 92 |
| 2.2 | 3A5.210 | | VL_Q89P | 53.5 | 3.80E+05 | 4.78E−04 | 1.26E−09 | 18 | 25 | 72 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 2.2 | 3A5.211 | | VL_V90A | 55.7 | 7.65E+05 | 1.06E−04 | 1.39E−10 | 18.8 | 105 | 78 |
| 3.1 | 3A5.040 | 1 | Wild type | 53.3 | 7.72E+05 | 1.32E−04 | 1.71E−10 | 18.2 | | |
| 3.1 | 3A5.040 | 2 | Wild type | 53.4 | 7.76E+05 | 1.15E−04 | 1.48E−10 | 18.1 | | |
| 3.1 | 3A5.040 | 3 | Wild type | 53.3 | 7.73E+05 | 1.03E−04 | 1.34E−10 | 18.1 | | |
| 3.1 | 3A5.040 | 4 | Wild type | 54 | 7.69E+05 | 1.14E−04 | 1.49E−10 | 18.5 | | |
| 3.1 | 3A5.040 | 5 | Wild type | 53.8 | 7.84E+05 | 1.20E−04 | 1.53E−10 | 18.4 | | |
| 3.1 | 3A5.040 | Average | Wild type | 53.6 | 7.75E+05 | 1.17E−04 | 1.51E−10 | 18.2 | 100 | 100 |
| 3.1 | IgG4 Isotype | | | 56 | N/A | N/A | N/A | 0.7 | N/A | |
| 3.1 | 3A5.040 (Purified) | | Wild type | 52.5 | 8.07E+05 | 1.40E−04 | 1.74E−10 | 17.9 | 83 | |
| 3.1 | 3A5.213 | | VL_V90L | 53.7 | 7.49E+05 | 1.55E−04 | 2.06E−10 | 18.2 | 75 | 58 |
| 3.1 | 3A5.214 | | VL_V90Y | 54 | 6.50E+05 | 2.92E−04 | 4.49E−10 | 18 | 40 | 85 |
| 3.1 | 3A5.215 | | VL_V90D | 52.9 | 5.54E+05 | 4.19E−04 | 7.56E−10 | 19.9 | 28 | 27 |
| 3.1 | 3A5.216 | | VL_V90Q | 48.6 | 5.93E+05 | 1.88E−04 | 3.18E−10 | 16.3 | 62 | 74 |
| 3.1 | 3A5.217 | | VL_V90K | 44.3 | 6.34E+05 | 8.30E−05 | 1.31E−10 | 17 | 141 | 48 |
| 3.1 | 3A5.218 | | VL_V90H | 47.5 | 5.90E+05 | 2.99E−04 | 5.07E−10 | 17.6 | 39 | 60 |
| 3.1 | 3A5.219 | | VL_V90W | 53.4 | 5.69E+05 | 6.64E−04 | 1.17E−09 | 17.9 | 18 | 77 |
| 3.1 | 3A5.220 | | VL_V90P | 47.7 | 2.72E+05 | 7.61E−03 | 2.79E−08 | 1.7 | 2 | 76 |
| 3.1 | 3A5.221 | | VL_W91A | 51.8 | 3.05E+05 | 7.08E−03 | 2.32E−08 | 2.4 | 2 | 79 |
| 3.1 | 3A5.223 | | VL_W91L | 53.6 | 2.59E+06 | 2.55E−02 | 9.83E−09 | 7.7 | 0 | 98 |
| 3.1 | 3A5.224 | | VL_W91Y | 45.1 | 8.82E+05 | 9.03E−04 | 1.02E−09 | 15.8 | 13 | 64 |
| 3.1 | 3A5.226 | | VL_W91Q | 51.1 | 5.38E+06 | 3.79E−02 | 7.05E−09 | 6.8 | 0 | 75 |
| 3.1 | 3A5.227 | | VL_W91K | 51.8 | | | | | NB | 71 |
| 3.1 | 3A5.228 | | VL_W91H | 50.9 | 1.53E+06 | 7.24E−03 | 4.74E−09 | 9 | 2 | 62 |
| 3.1 | 3A5.229 | | VL_W91P | 39.4 | 4.02E+05 | 7.40E−03 | 1.84E−08 | 1.4 | 2 | 36 |
| 3.1 | 3A5.230 | | VL_D92A | 51.2 | 5.63E+05 | 9.94E−05 | 1.77E−10 | 16.5 | 118 | 113 |
| 3.1 | 3A5.231 | | VL_D92S | 53.2 | 7.67E+05 | 9.46E−05 | 1.23E−10 | 17.5 | 124 | 113 |
| 3.1 | 3A5.232 | | VL_D92L | 54.3 | 9.17E+05 | 7.59E−05 | 8.27E−11 | 18 | 154 | 130 |
| 3.1 | 3A5.233 | | VL_D92Y | 47.7 | 1.11E+06 | 1.10E−04 | 9.92E−11 | 16.4 | 106 | 72 |
| 3.1 | 3A5.234 | | VL_D92Q | 50.9 | 5.25E+05 | 1.39E−04 | 2.64E−10 | 15.7 | 84 | 194 |
| 3.1 | 3A5.235 | | VL_D92K | 54.7 | 7.63E+05 | 8.84E−05 | 1.16E−10 | 18 | 132 | 92 |
| 3.1 | 3A5.236 | | VL_D92H | 54.3 | 7.93E+05 | 1.09E−04 | 1.37E−10 | 17.6 | 107 | 122 |
| 3.1 | 3A5.237 | | VL_D92W | 0.5 | | | | | NE | NE |
| 3.1 | 3A5.238 | | VL_D92P | 46.8 | 5.21E+05 | 1.43E−04 | 2.75E−10 | 16.1 | 82 | 63 |
| 3.1 | 3A5.239 | | VL_S93A | 52.2 | 3.12E+06 | 3.65E−03 | 1.17E−09 | 15.9 | 3 | 112 |
| 3.1 | 3A5.240 | | VL_S93L | 54.8 | 2.39E+07 | 2.45E−01 | 1.03E−08 | 6.5 | 0 | 124 |
| 3.1 | 3A5.241 | | VL_S93Y | 50.1 | 6.20E+05 | 7.48E−03 | 1.21E−08 | 2 | 2 | 118 |
| 3.1 | 3A5.242 | | VL_S93D | 51.6 | 5.18E+05 | 1.68E−02 | 3.25E−08 | 2.9 | 1 | 73 |
| 3.1 | 3A5.243 | | VL_S93Q | 54.4 | 1.90E+06 | 1.51E−02 | 7.95E−09 | 8.2 | 1 | 111 |
| 3.1 | 3A5.244 | | VL_S93K | 55.5 | | | | | NB | 162 |
| 3.1 | 3A5.245 | | VL_S93H | 49.7 | 2.92E+06 | 2.23E−02 | 7.64E−09 | 7.3 | 1 | 133 |
| 3.1 | 3A5.246 | | VL_S93W | 52.8 | 3.27E+05 | 4.33E−03 | 1.33E−08 | 0.8 | 3 | 115 |
| 3.1 | 3A5.247 | | VL_S93P | 53.8 | 6.94E+05 | 5.33E−02 | 7.68E−08 | 1.7 | 0 | 112 |
| 3.1 | 3A5.248 | | VL_S94A | 56.1 | 8.15E+05 | 1.22E−04 | 1.50E−10 | 19.1 | 96 | 101 |
| 3.1 | 3A5.249 | | VL_S94L | 49.7 | 7.81E+05 | 5.00E−04 | 6.41E−10 | 17.1 | 23 | 90 |
| 3.1 | 3A5.253 | | VL_S94K | 53 | 6.74E+05 | 1.48E−04 | 2.20E−10 | 17.9 | 79 | 109 |
| 3.1 | 3A5.254 | | VL_S94H | 53.7 | 6.24E+05 | 1.51E−04 | 2.42E−10 | 18.1 | 77 | 104 |
| 3.1 | 3A5.256 | | VL_S94P | 49.7 | 6.97E+05 | 1.27E−04 | 1.82E−10 | 16.7 | 92 | 139 |
| 3.1 | 3A5.257 | | VL_S95A | 52.1 | 7.34E+05 | 1.19E−04 | 1.62E−10 | 17.7 | 98 | 99 |
| 3.1 | 3A5.258 | | VL_S95L | 54 | 7.73E+05 | 1.13E−04 | 1.47E−10 | 18.3 | 104 | 99 |
| 3.1 | 3A5.259 | | VL_S95Y | 55.7 | 8.35E+05 | 1.07E−04 | 1.28E−10 | 18.7 | 109 | 83 |
| 3.1 | 3A5.260 | | VL_S95D | 49.2 | 6.07E+05 | 1.25E−04 | 2.07E−10 | 16.5 | 94 | 109 |
| 3.1 | 3A5.261 | | VL_S95Q | 48.6 | 7.87E+05 | 9.19E−05 | 1.17E−10 | 17.8 | 127 | 62 |
| 3.1 | 3A5.262 | | VL_S95K | 53.1 | 7.99E+05 | 1.01E−04 | 1.26E−10 | 18.2 | 116 | 118 |
| 3.1 | 3A5.263 | | VL_S95H | 55.4 | 7.83E+05 | 1.00E−04 | 1.28E−10 | 18.7 | 117 | 101 |
| 3.1 | 3A5.264 | | VL_S95W | 49 | 7.95E+05 | 1.27E−04 | 1.60E−10 | 16.5 | 92 | 87 |
| 3.1 | 3A5.265 | | VL_S95P | 52.7 | 6.45E+05 | 5.55E−03 | 8.61E−09 | 7.1 | 2 | 147 |
| 3.1 | 3A5.266 | | VL_D95aA | 53.7 | 5.78E+06 | 8.07E−03 | 1.40E−09 | 10.4 | 1 | 109 |
| 3.1 | 3A5.267 | | VL_D95aS | 55.3 | 4.53E+05 | 1.21E−03 | 2.68E−09 | 16.7 | 10 | 101 |
| 3.1 | 3A5.268 | | VL_D95aL | 48.5 | 9.19E+06 | 1.35E−02 | 1.47E−09 | 8.7 | 1 | 71 |
| 3.1 | 3A5.269 | | VL_D95aY | 51.8 | 1.77E+06 | 6.74E−03 | 3.80E−09 | 8 | 2 | 95 |
| 3.1 | 3A5.270 | | VL_D95aQ | 53.6 | 5.26E+06 | 7.11E−03 | 1.35E−09 | 11.4 | 2 | 110 |
| 3.1 | 3A5.271 | | VL_D95aK | 53.8 | 3.92E+05 | 3.83E−02 | 9.77E−08 | 2 | 0 | 70 |
| 3.1 | 3A5.272 | | VL_D95aH | 49.7 | 2.56E+06 | 4.90E−03 | 1.92E−09 | 10.1 | 2 | 188 |
| 3.1 | 3A5.273 | | VL_D95aW | 53.1 | 1.27E+06 | 1.47E−02 | 1.15E−08 | 7.1 | 1 | 94 |
| 3.1 | 3A5.274 | | VL_D95aP | 54.6 | 1.17E+06 | 3.05E−03 | 2.61E−09 | 9.8 | 4 | 150 |
| 3.1 | 3A5.276 | | VL_H95bS | 52.1 | 8.47E+05 | 7.33E−05 | 8.66E−11 | 19.6 | 160 | 61 |
| 3.1 | 3A5.281 | | VL_H95bK | 45.5 | 7.08E+05 | 9.58E−05 | 1.35E−10 | 16.3 | 122 | 64 |
| 3.1 | 3A5.307 | | VH_G26Y | 48.1 | 8.73E+05 | 1.02E−04 | 1.17E−10 | 18.3 | 115 | 60 |
| 3.1 | 3A5.321 | | VH_G27W | 55 | 7.64E+05 | 5.59E−04 | 7.31E−10 | 18.4 | 21 | 97 |
| 3.1 | 3A5.335 | | VH_I29Q | 37.9 | 5.64E+05 | 3.90E−04 | 6.92E−10 | 14.9 | 30 | 37 |
| 3.1 | 3A5.343 | | VH_S30Q | 51.9 | 7.55E+05 | 1.06E−04 | 1.40E−10 | 17.7 | 110 | 121 |
| 3.1 | 3A5.344 | | VH_S30K | 53.9 | 7.41E+05 | 1.39E−04 | 1.88E−10 | 18 | 84 | 156 |
| 3.1 | 3A5.345 | | VH_S30H | 54.8 | 7.34E+05 | 1.46E−04 | 1.99E−10 | 18.7 | 80 | 77 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 3.1 | 3A5.349 | | VH_N31L | 47.1 | 7.69E+05 | 7.13E−04 | 9.27E−10 | 16.3 | 16 | 69 |
| 3.1 | 3A5.355 | | VH_N31W | 45.3 | 8.52E+05 | 4.80E−04 | 5.63E−10 | 17.3 | 24 | 59 |
| 3.1 | 3A5.359 | | VH_G32Y | 53.7 | 3.28E+06 | 4.30E−03 | 1.31E−09 | 15.5 | 3 | 90 |
| 3.1 | 3A5.360 | | VH_G32D | 54.2 | 1.05E+06 | 6.78E−03 | 6.44E−09 | 8.1 | 2 | 105 |
| 3.1 | 3A5.361 | | VH_G32Q | 49.5 | 3.98E+06 | 6.22E−03 | 1.56E−09 | 11.8 | 2 | 133 |
| 3.1 | 3A5.362 | | VH_G32K | 52.6 | 6.07E+05 | 2.20E−03 | 3.62E−09 | 7.6 | 5 | 171 |
| 3.1 | 3A5.363 | | VH_G32H | 55.4 | 1.81E+06 | 3.01E−03 | 1.66E−09 | 15.3 | 4 | 114 |
| 3.1 | 3A5.364 | | VH_G32W | 52.3 | 1.46E+07 | 1.27E−02 | 8.65E−10 | 13.5 | 1 | 66 |
| 3.1 | 3A5.365 | | VH_G33A | 48.7 | 6.97E+05 | 9.24E−05 | 1.33E−10 | 16.6 | 127 | 116 |
| 3.1 | 3A5.366 | | VH_G33S | 53 | 8.56E+05 | 2.68E−03 | 3.14E−09 | 8.3 | 4 | 117 |
| 3.1 | 3A5.367 | | VH_G33L | 54.2 | 8.03E+05 | 3.05E−04 | 3.79E−10 | 17.9 | 38 | 82 |
| 3.1 | 3A5.368 | | VH_G33Y | 55.4 | 3.97E+06 | 4.08E−03 | 1.03E−09 | 13.4 | 3 | 107 |
| 3.2 | 3A5.040 | 1 | Wild type | 54.7 | 6.75E+05 | 9.46E−05 | 1.40E−10 | 19 | | |
| 3.2 | 3A5.040 | 2 | Wild type | 55.2 | 6.82E+05 | 7.26E−05 | 1.07E−10 | 19 | | |
| 3.2 | 3A5.040 | 3 | Wild type | 55.7 | 7.17E+05 | 9.30E−05 | 1.30E−10 | 19.3 | | |
| 3.2 | 3A5.040 | 4 | Wild type | 55.3 | 7.08E+05 | 8.82E−05 | 1.25E−10 | 19.1 | | |
| 3.2 | 3A5.040 | 5 | Wild type | 55.2 | 6.95E+05 | 1.05E−04 | 1.51E−10 | 19.2 | | |
| 3.2 | 3A5.040 | Average | Wild type | 55.2 | 6.95E+05 | 9.07E−05 | 1.31E−10 | 19.1 | 100 | 100 |
| 3.2 | IgG4 Isotype | | | 55.8 | N/A | N/A | N/A | 0 | N/A | |
| 3.2 | 3A5.040 (Purified) | | Wild type | 54.5 | 7.12E+05 | 8.25E−05 | 1.16E−10 | 1.85E+01 | 110 | |
| 3.2 | 3A5.369 | | VH_G33D | 52.4 | 9.85E+05 | 2.46E−03 | 2.50E−09 | 9.4 | 4 | 277 |
| 3.2 | 3A5.370 | | VH_G33Q | 54.5 | 5.33E+05 | 1.07E−03 | 2.00E−09 | 17.2 | 8 | 279 |
| 3.2 | 3A5.371 | | VH_G33K | 58.5 | 2.08E+06 | 2.02E−03 | 9.72E−10 | 14.1 | 4 | 350 |
| 3.2 | 3A5.372 | | VH_G33H | 51.5 | 1.45E+06 | 2.67E−03 | 1.83E−09 | 14.4 | 3 | 273 |
| 3.2 | 3A5.373 | | VH_G33W | 52.4 | 6.71E+05 | 1.32E−03 | 1.96E−09 | 15.9 | 7 | 172 |
| 3.2 | 3A5.374 | | VH_Y34A | 56.4 | 5.91E+05 | 1.27E−04 | 2.16E−10 | 19.2 | 71 | 162 |
| 3.2 | 3A5.375 | | VH_Y34S | 56.4 | 6.23E+05 | 1.24E−04 | 2.00E−10 | 19.1 | 73 | 159 |
| 3.2 | 3A5.376 | | VH_Y34L | 50 | 5.79E+05 | 1.60E−04 | 2.77E−10 | 17.2 | 57 | 160 |
| 3.2 | 3A5.377 | | VH_Y34D | 54.7 | 5.40E+05 | 6.04E−04 | 1.12E−09 | 18.1 | 15 | 103 |
| 3.2 | 3A5.378 | | VH_Y34Q | 54.4 | 5.98E+05 | 1.51E−04 | 2.53E−10 | 18.5 | 60 | 165 |
| 3.2 | 3A5.379 | | VH_Y34K | 56.6 | 6.17E+05 | 4.91E−04 | 7.96E−10 | 19.1 | 18 | 407 |
| 3.2 | 3A5.380 | | VH_Y34H | 49.8 | 6.40E+05 | 7.06E−04 | 1.10E−09 | 16.7 | 13 | 223 |
| 3.2 | 3A5.382 | | VH_Y35A | 52.8 | 2.48E+05 | 2.46E−03 | 9.91E−09 | 0.9 | 4 | 289 |
| 3.2 | 3A5.383 | | VH_Y35S | 55.8 | 3.34E+05 | 8.50E−03 | 2.54E−08 | 1.9 | 1 | 129 |
| 3.2 | 3A5.384 | | VH_Y35L | 57 | 5.98E+05 | 1.42E−03 | 2.37E−09 | 17.5 | 6 | 190 |
| 3.2 | 3A5.385 | | VH_Y35D | 48.5 | 2.75E+06 | 6.13E−03 | 2.23E−09 | 8.1 | 1 | 87 |
| 3.2 | 3A5.386 | | VH_Y35Q | 51.8 | 1.18E+07 | 2.72E−01 | 2.31E−08 | 5.4 | 0 | 127 |
| 3.2 | 3A5.387 | | VH_Y35K | 56.2 | | | | | NB | 382 |
| 3.2 | 3A5.388 | | VH_Y35H | 58 | 3.40E+05 | 9.25E−03 | 2.72E−08 | 3.3 | 1 | 195 |
| 3.2 | 3A5.389 | | VH_Y35W | 50 | 3.65E+06 | 5.41E−03 | 1.48E−09 | 8.8 | 2 | 225 |
| 3.2 | 3A5.390 | | VH_W35aA | 47 | 6.84E+05 | 1.74E−03 | 2.55E−09 | 15.4 | 5 | 37 |
| 3.2 | 3A5.392 | | VH_W35aL | 55 | 4.59E+05 | 1.14E−03 | 2.49E−09 | 17.1 | 8 | 100 |
| 3.2 | 3A5.393 | | VH_W35aY | 49.1 | 6.34E+05 | 1.87E−04 | 2.94E−10 | 16.7 | 49 | 104 |
| 3.2 | 3A5.394 | | VH_W35aD | 0.7 | | | | | NE | NE |
| 3.2 | 3A5.395 | | VH_W35aQ | 50.4 | 5.46E+05 | 8.47E−04 | 1.55E−09 | 18.8 | 11 | 34 |
| 3.2 | 3A5.397 | | VH_W35aH | 39.6 | 5.07E+05 | 2.44E−04 | 4.82E−10 | 15.8 | 37 | 53 |
| 3.2 | 3A5.399 | | VH_S35bL | 46 | 1.08E+05 | 2.86E−04 | 2.64E−09 | 14.1 | 32 | 39 |
| 3.2 | 3A5.400 | | VH_S35bY | 51.7 | 4.43E+05 | 7.06E−03 | 1.59E−08 | 1.8 | 1 | 88 |
| 3.2 | 3A5.402 | | VH_S35bQ | 38.8 | 1.84E+05 | 5.15E−04 | 2.80E−09 | 13.6 | 18 | 45 |
| 3.2 | 3A5.404 | | VH_S35bH | 48.8 | 6.18E+05 | 1.88E−03 | 3.05E−09 | 13.3 | 5 | 75 |
| 3.2 | 3A5.405 | | VH_S35bW | 49.6 | 2.93E+05 | 7.19E−03 | 2.45E−08 | 0.7 | 1 | 50 |
| 3.2 | 3A5.406 | | VH_Y50A | 50.6 | 4.79E+05 | 5.88E−04 | 1.23E−09 | 16.1 | 15 | 268 |
| 3.2 | 3A5.407 | | VH_Y50S | 56.1 | 4.95E+05 | 3.64E−04 | 7.34E−10 | 17.5 | 25 | 327 |
| 3.2 | 3A5.408 | | VH_Y50L | 57 | 4.31E+05 | 3.22E−04 | 7.46E−10 | 17.3 | 28 | 122 |
| 3.2 | 3A5.409 | | VH_Y50D | 56.9 | 7.63E+05 | 1.45E−03 | 1.90E−09 | 16 | 6 | 169 |
| 3.2 | 3A5.410 | | VH_Y50Q | 50.9 | 5.95E+05 | 3.69E−04 | 6.20E−10 | 17.1 | 25 | 241 |
| 3.2 | 3A5.411 | | VH_Y50K | 53.5 | 5.51E+05 | 4.47E−04 | 8.11E−10 | 17.5 | 20 | 135 |
| 3.2 | 3A5.412 | | VH_Y50H | 55.5 | 6.72E+05 | 7.88E−04 | 1.17E−09 | 18.2 | 12 | 300 |
| 3.2 | 3A5.413 | | VH_Y50W | 57.2 | 6.67E+05 | 1.61E−03 | 2.41E−09 | 16.9 | 6 | 131 |
| 3.2 | 3A5.414 | | VH_I51A | 51.9 | 7.29E+05 | 1.13E−04 | 1.56E−10 | 17.7 | 80 | 244 |
| 3.2 | 3A5.415 | | VH_I51S | 54.2 | 7.38E+05 | 1.15E−04 | 1.56E−10 | 18.6 | 79 | 130 |
| 3.2 | 3A5.416 | | VH_I51L | 54.6 | 6.62E+05 | 1.39E−04 | 2.10E−10 | 19 | 65 | 87 |
| 3.2 | 3A5.417 | | VH_I51Y | 57.2 | 5.42E+05 | 7.77E−03 | 1.43E−08 | 7.9 | 1 | 106 |
| 3.2 | 3A5.418 | | VH_I51D | 40.4 | 5.15E+05 | 6.36E−04 | 1.23E−09 | 15.8 | 14 | 48 |
| 3.2 | 3A5.419 | | VH_I51Q | 51.6 | 6.26E+05 | 5.02E−04 | 8.01E−10 | 17.7 | 18 | 95 |
| 3.2 | 3A5.420 | | VH_I51K | 53.3 | 7.42E+05 | 1.16E−03 | 1.57E−09 | 17.3 | 8 | 124 |
| 3.2 | 3A5.421 | | VH_I51H | 54.1 | 7.46E+06 | 8.34E−03 | 1.12E−09 | 13.4 | 1 | 93 |
| 3.2 | 3A5.422 | | VH_I51W | 49.7 | 3.18E+05 | 3.31E−03 | 1.04E−08 | 0.9 | 3 | 139 |
| 3.2 | 3A5.423 | | VH_Y52A | 54.9 | 1.49E+07 | 1.08E−02 | 7.23E−10 | 11.8 | 1 | 304 |
| 3.2 | 3A5.424 | | VH_Y52S | 57.3 | 6.79E+05 | 1.29E−03 | 1.89E−09 | 11.7 | 7 | 325 |
| 3.2 | 3A5.425 | | VH_Y52L | 59.4 | 1.90E+06 | 8.83E−03 | 4.66E−09 | 10.1 | 1 | 209 |
| 3.2 | 3A5.426 | | VH_Y52D | 51.7 | | | | | NB | 333 |
| 3.2 | 3A5.427 | | VH_Y52Q | 55.5 | 1.86E+06 | 8.86E−03 | 4.76E−09 | 9.2 | 1 | 264 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 3.2 | 3A5.428 | | VH_Y52K | 58.4 | | | | | NB | 348 |
| 3.2 | 3A5.429 | | VH_Y52H | 61.5 | 5.62E+05 | 2.91E−04 | 5.17E−10 | 20.6 | 31 | 286 |
| 3.2 | 3A5.430 | | VH_Y52W | 48.6 | 6.79E+05 | 1.26E−03 | 1.86E−09 | 15.9 | 7 | 102 |
| 3.2 | 3A5.431 | | VH_Y53A | 53 | 6.79E+05 | 5.21E−04 | 7.67E−10 | 17.9 | 17 | 249 |
| 3.2 | 3A5.432 | | VH_Y53S | 55 | 6.94E+05 | 1.57E−04 | 2.26E−10 | 18.8 | 58 | 226 |
| 3.2 | 3A5.433 | | VH_Y53L | 57.3 | 6.02E+05 | 4.43E−04 | 7.36E−10 | 19.1 | 20 | 102 |
| 3.2 | 3A5.434 | | VH_Y53D | 50.8 | 4.80E+05 | 5.94E−04 | 1.24E−09 | 16.6 | 15 | 182 |
| 3.2 | 3A5.435 | | VH_Y53Q | 53.4 | 6.27E+05 | 4.41E−04 | 7.03E−10 | 17.9 | 21 | 206 |
| 3.2 | 3A5.436 | | VH_Y53K | 56.7 | 6.17E+05 | 9.61E−04 | 1.56E−09 | 18.1 | 9 | 232 |
| 3.2 | 3A5.437 | | VH_Y53H | 57 | 6.71E+05 | 1.91E−04 | 2.85E−10 | 19.1 | 47 | 206 |
| 3.2 | 3A5.438 | | VH_Y53W | 49.2 | 6.91E+05 | 2.35E−04 | 3.40E−10 | 16.8 | 39 | 152 |
| 3.2 | 3A5.439 | | VH_S54A | 53.1 | 6.98E+05 | 1.54E−04 | 2.20E−10 | 18.1 | 59 | 112 |
| 3.2 | 3A5.440 | | VH_S54L | 53.4 | 9.17E+06 | 8.95E−03 | 9.76E−10 | 13.6 | 1 | 158 |
| 3.2 | 3A5.441 | | VH_S54Y | 55 | 1.57E+06 | 2.17E−03 | 1.38E−09 | 16.5 | 4 | 92 |
| 3.2 | 3A5.442 | | VH_S54D | 51.4 | 8.06E+05 | 2.02E−03 | 2.50E−09 | 14.4 | 4 | 200 |
| 3.2 | 3A5.443 | | VH_S54Q | 54 | 6.04E+05 | 1.07E−03 | 1.77E−09 | 17.6 | 8 | 150 |
| 3.2 | 3A5.444 | | VH_S54K | 55.6 | 2.65E+06 | 3.55E−03 | 1.34E−09 | 15.5 | 3 | 201 |
| 3.2 | 3A5.445 | | VH_S54H | 57.5 | 7.10E+05 | 4.59E−04 | 6.46E−10 | 19.3 | 20 | 97 |
| 3.2 | 3A5.446 | | VH_S54W | 46.7 | 7.24E+05 | 8.68E−04 | 1.20E−09 | 14.8 | 10 | 112 |
| 3.2 | 3A5.447 | | VH_G55A | 45.7 | 6.76E+05 | 1.05E−04 | 1.55E−10 | 17.1 | 86 | 68 |
| 3.2 | 3A5.448 | | VH_G55S | 48.4 | 7.30E+05 | 1.24E−04 | 1.70E−10 | 18 | 73 | 72 |
| 3.2 | 3A5.449 | | VH_G55L | 47.7 | 6.14E+05 | 6.30E−04 | 1.03E−09 | 17.7 | 14 | 66 |
| 3.2 | 3A5.450 | | VH_G55Y | 38.6 | 6.88E+05 | 7.06E−04 | 1.03E−09 | 14.2 | 13 | 49 |
| 4.1 | 3A5.040 | 1 | Wild type | 82.7 | 1.00E+06 | 1.16E−04 | 1.16E−10 | 24.9 | | |
| 4.1 | 3A5.040 | 2 | Wild type | 82.7 | 1.02E+06 | 1.07E−04 | 1.04E−10 | 25.1 | | |
| 4.1 | 3A5.040 | 3 | Wild type | 85.2 | 1.03E+06 | 1.12E−04 | 1.09E−10 | 25.1 | | |
| 4.1 | 3A5.040 | 4 | Wild type | 85.1 | 1.01E+06 | 1.06E−04 | 1.05E−10 | 25.3 | | |
| 4.1 | 3A5.040 | 5 | Wild type | 83.5 | 9.91E+05 | 9.29E−05 | 9.37E−11 | 25.3 | | |
| 4.1 | 3A5.040 | Average | Wild type | 83.84 | 1.01E+06 | 1.07E−04 | 1.06E−10 | 25.14 | 100 | 100 |
| 4.1 | IgG4 Isotype | | | 61.4 | N/A | N/A | N/A | 0 | N/A | |
| 4.1 | 3A5.040 (Purified) | | Wild type | 84.2 | 1.06E+06 | 1.09E−04 | 1.03E−10 | 23.8 | 98 | |
| 4.1 | 3A5.133 | | VL_V33K | 52.7 | 7.83E+05 | 1.34E−04 | 1.71E−10 | 15.9 | 80 | 15 |
| 4.1 | 3A5.222 | | VL_W91S | 62.8 | 1.38E+06 | 2.85E−03 | 2.06E−09 | 12.5 | 4 | 14 |
| 4.1 | 3A5.391 | | VH_W35aS | 68.4 | 6.35E+05 | 1.19E−03 | 1.87E−09 | 15.6 | 9 | 22 |
| 4.1 | 3A5.396 | | VH_W35aK | 65.9 | 7.21E+05 | 2.08E−03 | 2.88E−09 | 9.4 | 5 | 26 |
| 4.1 | 3A5.401 | | VH_S35bD | 53.1 | 5.96E+05 | 1.19E−04 | 2.01E−10 | 14.5 | 90 | 16 |
| 4.1 | 3A5.403 | | VH_S35bK | 53.1 | 1.83E+05 | 1.23E−02 | 6.68E−08 | 2.8 | 1 | 12 |
| 4.1 | 3A5.275 | | VL_H95bA | 69.7 | 5.47E+05 | 1.62E−04 | 2.95E−10 | 18 | 66 | 24 |
| 4.1 | 3A5.282 | | VL_H95bW | 77.5 | 7.18E+05 | 1.07E−04 | 1.49E−10 | 21.1 | 100 | 152 |
| 4.1 | 3A5.283 | | VL_H95bP | 63.4 | 5.90E+05 | 4.22E−02 | 7.15E−08 | 3.6 | 0 | 154 |
| 4.1 | 3A5.285 | | VL_V96S | 74.4 | 9.02E+05 | 2.01E−04 | 2.23E−10 | 19.9 | 53 | 21 |
| 4.1 | 3A5.287 | | VL_V96Y | 92.4 | 7.33E+06 | 1.50E−03 | 2.05E−10 | 17.6 | 7 | 62 |
| 4.1 | 3A5.288 | | VL_V96D | 68.8 | 7.32E+05 | 1.30E−03 | 1.78E−09 | 16.8 | 8 | 9.5 |
| 4.1 | 3A5.289 | | VL_V96Q | 77.1 | 1.62E+06 | 6.54E−04 | 4.03E−10 | 20.4 | 16 | 25 |
| 4.1 | 3A5.290 | | VL_V96K | 64.6 | 8.08E+05 | 2.32E−03 | 2.87E−09 | 13.1 | 5 | 15 |
| 4.1 | 3A5.291 | | VL_V96H | 5.2 | | | | | NB | 45 |
| 4.1 | 3A5.292 | | VL_V96W | 66.4 | 3.83E+07 | 2.01E−02 | 5.26E−10 | 10.6 | 1 | 19 |
| 4.1 | 3A5.293 | | VL_V96P | 81.5 | 8.54E+05 | 5.22E−04 | 6.11E−10 | 23.4 | 20 | 106 |
| 4.1 | 3A5.110 | | VL_K31A | 74 | 7.01E+05 | 1.86E−04 | 2.65E−10 | 21.1 | 58 | 122 |
| 4.1 | 3A5.111 | | VL_K31S | 79.2 | 7.10E+05 | 1.36E−04 | 1.92E−10 | 23.6 | 79 | 109 |
| 4.1 | 3A5.112 | | VL_K31L | 79.9 | 6.30E+05 | 3.91E−04 | 6.21E−10 | 22.3 | 27 | 125 |
| 4.1 | 3A5.134 | | VL_V33H | 5.8 | | | | | NB | 52 |
| 4.1 | 3A5.136 | | VL_Y34A | 59.9 | 1.05E+06 | 3.45E−04 | 3.28E−10 | 17.2 | 31 | 170 |
| 4.1 | 3A5.206 | | VL_Q89D | 71.6 | 5.68E+05 | 8.76E−05 | 1.54E−10 | 18.6 | 122 | 12 |
| 4.1 | 3A5.225 | | VL_W91D | 114.2 | 6.31E+05 | 1.05E−02 | 1.66E−08 | 3.7 | 1 | 74 |
| 4.1 | 3A5.250 | | VL_S94Y | 74.6 | 8.14E+05 | 3.48E−04 | 4.27E−10 | 20.3 | 31 | 147 |
| 4.1 | 3A5.252 | | VL_S94Q | 63.4 | 8.25E+05 | 1.65E−04 | 2.00E−10 | 18 | 65 | 136 |
| 4.2 | 3A5.040 | 1 | Wild type | 50.4 | 6.96E+05 | 1.03E−04 | 1.48E−10 | 16.2 | | |
| 4.2 | 3A5.040 | 2 | Wild type | 50.5 | 7.10E+05 | 1.06E−04 | 1.49E−10 | 16 | | |
| 4.2 | 3A5.040 | Average | Wild type | 50.4 | 7.03E+05 | 1.05E−04 | 1.49E−10 | 16.1 | 100 | 100 |
| 4.2 | IgG4 Isotype | | | 52.5 | N/A | N/A | N/A | | N/A | |
| 4.2 | 3A5.040 (Purified) | | Wild type | 48.7 | 7.21E+05 | 6.63E−05 | 9.20E−11 | 16.5 | 150 | |
| 4.2 | 3A5.451 | | VH_G55D | 33.1 | 4.54E+05 | 2.50E−04 | 5.50E−10 | 9.9 | 42 | 39 |
| 4.2 | 3A5.452 | | VH_G55Q | 37.2 | 6.09E+05 | 1.94E−04 | 3.18E−10 | 11.7 | 54 | 42 |
| 4.2 | 3A5.453 | | VH_G55K | 43.8 | 5.49E+05 | 2.07E−04 | 3.76E−10 | 12.4 | 50 | 51 |
| 4.2 | 3A5.454 | | VH_G55H | 38.2 | 5.92E+05 | 1.81E−04 | 3.05E−10 | 11.7 | 58 | 41 |
| 4.2 | 3A5.455 | | VH_G55W | 31.2 | 6.17E+05 | 6.65E−04 | 1.08E−09 | 10 | 16 | 33 |
| 4.2 | 3A5.456 | | VH_S56A | 49.7 | 6.44E+05 | 1.18E−04 | 1.84E−10 | 15.5 | 89 | 104 |
| 4.2 | 3A5.457 | | VH_S56L | 51.1 | 5.49E+05 | 8.63E−05 | 1.57E−10 | 15.6 | 121 | 101 |
| 4.2 | 3A5.458 | | VH_S56Y | 47.6 | 5.44E+05 | 1.92E−04 | 3.53E−10 | 14.2 | 54 | 85 |
| 4.2 | 3A5.459 | | VH_S56D | 49 | 5.05E+05 | 4.57E−04 | 9.06E−10 | 15 | 23 | 84 |
| 4.2 | 3A5.460 | | VH_S56Q | 50.2 | 5.90E+05 | 9.69E−05 | 1.64E−10 | 15.8 | 108 | 106 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 4.2 | 3A5.461 | | VH_S56K | 52.9 | 6.11E+05 | 7.84E−05 | 1.28E−10 | 16.6 | 133 | 119 |
| 4.2 | 3A5.463 | | VH_S56W | 47.7 | 4.72E+05 | 2.85E−04 | 6.03E−10 | 13.9 | 37 | 98 |
| 4.2 | 3A5.464 | | VH_T57A | 50 | 7.50E+05 | 1.26E−04 | 1.67E−10 | 16.1 | 83 | 104 |
| 4.2 | 3A5.465 | | VH_T57S | 48.5 | 7.29E+05 | 1.26E−04 | 1.73E−10 | 15.6 | 83 | 69 |
| 4.2 | 3A5.467 | | VH_T57Y | 44 | 7.66E+05 | 9.50E−05 | 1.24E−10 | 13.8 | 110 | 49 |
| 4.2 | 3A5.468 | | VH_T57D | 42.5 | 7.02E+05 | 9.89E−05 | 1.41E−10 | 14 | 106 | 46 |
| 4.2 | 3A5.469 | | VH_T57Q | 45.1 | 7.24E+05 | 1.07E−04 | 1.48E−10 | 14.2 | 98 | 58 |
| 4.2 | 3A5.470 | | VH_T57K | 46.5 | 7.28E+05 | 1.21E−04 | 1.66E−10 | 14.6 | 86 | 61 |
| 4.2 | 3A5.471 | | VH_T57H | 43.8 | 7.34E+05 | 1.09E−04 | 1.49E−10 | 13.9 | 96 | 50 |
| 4.2 | 3A5.472 | | VH_T57W | 39.2 | 7.57E+05 | 1.34E−04 | 1.77E−10 | 13.3 | 78 | 40 |
| 4.2 | 3A5.473 | | VH_Y58A | 48.1 | 1.56E+06 | 2.86E−03 | 1.83E−09 | 13 | 4 | 95 |
| 4.2 | 3A5.474 | | VH_Y58S | 50.7 | 2.76E+06 | 3.84E−03 | 1.39E−09 | 13.7 | 3 | 101 |
| 4.2 | 3A5.475 | | VH_Y58L | 48.6 | 5.58E+06 | 5.88E−03 | 1.05E−09 | 8.3 | 2 | 70 |
| 4.2 | 3A5.476 | | VH_Y58D | 42.4 | 1.89E+07 | 1.68E−02 | 8.88E−10 | 7.3 | 1 | 47 |
| 4.2 | 3A5.477 | | VH_Y58Q | 46.6 | 6.62E+05 | 1.33E−03 | 2.02E−09 | 13.9 | 8 | 75 |
| 4.2 | 3A5.478 | | VH_Y58K | 49.2 | 5.75E+05 | 1.31E−03 | 2.28E−09 | 14.6 | 8 | 102 |
| 4.2 | 3A5.479 | | VH_Y58H | 50.6 | 6.68E+05 | 5.75E−04 | 8.62E−10 | 15.8 | 18 | 91 |
| 4.2 | 3A5.480 | | VH_Y58W | 48.1 | 6.58E+05 | 5.53E−04 | 8.41E−10 | 14.7 | 19 | 79 |
| 4.2 | 3A5.481 | | VH_A93S | 45.3 | 7.18E+05 | 9.31E−05 | 1.30E−10 | 13.9 | 112 | 58 |
| 4.2 | 3A5.482 | | VH_A93L | 13 | 2.55E+05 | 2.02E−04 | 7.90E−10 | 5.2 | 52 | 17 |
| 4.2 | 3A5.484 | | VH_A93D | 0.5 | | | | | NE | NE |
| 4.2 | 3A5.485 | | VH_A93Q | 40.4 | 6.48E+05 | 1.00E−04 | 1.54E−10 | 12.7 | 105 | 44 |
| 4.2 | 3A5.486 | | VH_A93K | 17 | | | | | NE | NE |
| 4.2 | 3A5.487 | | VH_A93H | 28.8 | | | | | NE | NE |
| 4.2 | 3A5.489 | | VH_A93P | 6.5 | | | | | NE | NE |
| 4.2 | 3A5.491 | | VH_S94L | 37.4 | 5.33E+05 | 8.11E−04 | 1.52E−09 | 12.5 | 13 | 40 |
| 4.2 | 3A5.492 | | VH_S94Y | 30.3 | 3.27E+05 | 1.10E−03 | 3.37E−09 | 9.7 | 10 | 30 |
| 4.2 | 3A5.493 | | VH_S94D | 4.6 | | | | | NE | NE |
| 4.2 | 3A5.494 | | VH_S94Q | 42 | 6.74E+05 | 6.37E−04 | 9.45E−10 | 13.6 | 16 | 49 |
| 4.2 | 3A5.496 | | VH_S94H | 47.1 | 2.19E+06 | 4.62E−03 | 2.11E−09 | 6.5 | 2 | 72 |
| 4.2 | 3A5.501 | | VH_L95Y | 49 | 4.17E+06 | 5.88E−03 | 1.41E−09 | 12.4 | 2 | 96 |
| 4.2 | 3A5.502 | | VH_L95D | 21.2 | | | | | NB | 22 |
| 4.2 | 3A5.506 | | VH_L95W | 46.4 | 6.20E+06 | 7.36E−03 | 1.19E−09 | 8.4 | 1 | 68 |
| 4.2 | 3A5.511 | | VH_G96Y | 45.5 | | | | | NB | 59 |
| 4.2 | 3A5.519 | | VH_N97S | 48 | 5.61E+05 | 2.27E−04 | 4.04E−10 | 14.9 | 46 | 80 |
| 4.2 | 3A5.552 | | VH_D101K | 47.1 | 6.10E+05 | 3.63E−04 | 5.95E−10 | 14.6 | 29 | 67 |
| 4.2 | 3A5.358 | | VH_G32L | 48.4 | 2.01E+06 | 3.83E−03 | 1.91E−09 | 12.3 | 3 | 75 |
| 4.2 | 3A5.381 | | VH_Y34W | 42.4 | 7.09E+05 | 2.18E−04 | 3.07E−10 | 14 | 48 | 47 |
| 4.2 | 3A5.398 | | VH_S35bA | 47 | 6.82E+05 | 1.02E−04 | 1.50E−10 | 14.7 | 102 | 88 |
| 4.2 | 3A5.488 | | VH_A93W | 14.2 | | | | | NB | 17 |
| 4.2 | 3A5.490 | | VH_S94A | 49.6 | 6.78E+05 | 8.70E−05 | 1.28E−10 | 15.1 | 120 | 104 |
| 4.2 | 3A5.499 | | VH_L95A | 43.4 | 3.09E+06 | 7.48E−03 | 2.42E−09 | 10.4 | 1 | 51 |
| 4.2 | 3A5.508 | | VH_G96A | 47.1 | 5.77E+05 | 1.25E−04 | 2.17E−10 | 14.8 | 84 | 75 |
| 4.2 | 3A5.522 | | VH_N97D | 49 | 1.00E+06 | 1.91E−04 | 1.91E−10 | 15.5 | 54 | 91 |
| 4.2 | 3A5.554 | | VH_D101W | 32.7 | 1.38E+05 | 6.18E−04 | 4.47E−09 | 8.3 | 17 | 33 |
| 4.2 | 3A5.144 | | VL_D50A | 47.1 | 5.29E+05 | 1.67E−04 | 3.15E−10 | 14.5 | 63 | 77 |
| 4.2 | 3A5.145 | | VL_D50S | 48.2 | 5.74E+05 | 1.05E−04 | 1.83E−10 | 15.1 | 100 | 90 |
| 4.2 | 3A5.146 | | VL_D50L | 48 | 5.92E+05 | 2.59E−04 | 4.38E−10 | 15 | 40 | 86 |
| 4.2 | 3A5.147 | | VL_D50Y | 48 | 5.36E+05 | 1.95E−04 | 3.63E−10 | 15 | 54 | 78 |
| 4.2 | 3A5.148 | | VL_D50Q | 47 | 5.99E+05 | 1.93E−04 | 3.22E−10 | 15 | 54 | 70 |
| 4.2 | 3A5.149 | | VL_D50K | 45.8 | 6.00E+05 | 1.61E−04 | 2.68E−10 | 13.2 | 65 | 74 |
| 4.2 | 3A5.150 | | VL_D50H | 48.2 | 4.07E+05 | 1.68E−04 | 4.14E−10 | 14.3 | 62 | 95 |
| 4.2 | 3A5.151 | | VL_D50W | 48 | 5.36E+05 | 2.35E−04 | 4.38E−10 | 15 | 44 | 74 |
| 4.2 | 3A5.152 | | VL_D51A | 47 | 6.34E+05 | 1.34E−04 | 2.11E−10 | 14.6 | 78 | 88 |
| 4.2 | 3A5.153 | | VL_D51S | 46.1 | 8.53E+05 | 1.60E−04 | 1.87E−10 | 14.1 | 65 | 72 |
| 4.2 | 3A5.154 | | VL_D51L | 47.8 | 6.22E+05 | 1.63E−04 | 2.63E−10 | 14.3 | 64 | 83 |
| 4.2 | 3A5.155 | | VL_D51Y | 48.1 | 6.14E+05 | 1.78E−04 | 2.90E−10 | 13.7 | 59 | 75 |
| 4.2 | 3A5.156 | | VL_D51Q | 47.8 | 6.48E+05 | 1.15E−04 | 1.77E−10 | 15 | 91 | 85 |
| 4.2 | 3A5.157 | | VL_D51K | 45.2 | 5.85E+05 | 1.20E−04 | 2.05E−10 | 13.2 | 87 | 68 |
| 4.2 | 3A5.158 | | VL_D51H | 48.3 | 6.15E+05 | 1.82E−04 | 2.95E−10 | 14.7 | 57 | 86 |
| 4.2 | 3A5.159 | | VL_D51W | 45.7 | 4.93E+05 | 1.96E−04 | 3.98E−10 | 14.1 | 53 | 57 |
| 4.2 | 3A5.160 | | VL_S52A | 47.7 | 6.61E+05 | 1.11E−04 | 1.68E−10 | 15.2 | 94 | 80 |
| 4.2 | 3A5.161 | | VL_S52L | 47.8 | 6.87E+05 | 5.74E−05 | 8.36E−11 | 15 | 182 | 106 |
| 4.2 | 3A5.162 | | VL_S52Y | 49 | 7.26E+05 | 9.91E−05 | 1.36E−10 | 15.8 | 105 | 114 |
| 5.1 | 3A5.040 | 1 | Wild type | 49.9 | 6.56E+05 | 1.22E−04 | 1.86E−10 | 14.5 | | |
| 5.1 | 3A5.040 | 2 | Wild type | 48.5 | 6.43E+05 | 1.12E−04 | 1.75E−10 | 14.4 | | |
| 5.1 | 3A5.040 | 3 | Wild type | 48.1 | 6.67E+05 | 1.25E−04 | 1.87E−10 | 13.7 | | |
| 5.1 | 3A5.040 | 4 | Wild type | 50.4 | 6.63E+05 | 1.17E−04 | 1.77E−10 | 14.4 | | |
| 5.1 | 3A5.040 | Average | Wild type | 49.2 | 6.57E+05 | 1.19E−04 | 1.81E−10 | 14.3 | 100 | 100 |
| 5.1 | IgG4 Isotype | | | 51.2 | N/A | N/A | N/A | 0.1 | N/A | |
| 5.1 | 3A5.040 (Purified) | | Wild type | 48.9 | 7.07E+05 | 1.08E−04 | 1.53E−10 | 15.6 | 110 | |
| 5.1 | 3A5.337 | | VH_I29H | 48.1 | 4.79E+05 | 1.12E−03 | 2.34E−09 | 13.7 | 11 | 24 |
| 5.1 | 3A5.339 | | VH_S30A | 50.7 | 6.79E+05 | 1.12E−04 | 1.65E−10 | 16.3 | 106 | 6 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 5.1 | 3A5.346 | | VH_S30W | 53.4 | 6.42E+05 | 1.32E−04 | 2.06E−10 | 16.7 | 90 | 69 |
| 5.1 | 3A5.058 | | VL_G25S | 47.6 | 6.93E+05 | 1.08E−04 | 1.56E−10 | 15.7 | 110 | 43 |
| 5.1 | 3A5.090 | | VL_I28K | 49.1 | 5.73E+05 | 1.04E−04 | 1.81E−10 | 16.2 | 114 | 51 |
| 5.1 | 3A5.092 | | VL_I28W | 47 | 6.13E+05 | 1.30E−04 | 2.12E−10 | 15.5 | 92 | 35 |
| 5.1 | 3A5.212 | | VL_V90S | 46.1 | 5.71E+05 | 3.11E−04 | 5.45E−10 | 14.6 | 38 | 4.8 |
| 5.1 | 3A5.251 | | VL_S94D | 52.9 | 2.77E+05 | 4.98E−04 | 1.79E−09 | 15.5 | 24 | 7 |
| 5.1 | 3A5.255 | | VL_S94W | 48.5 | 5.54E+05 | 2.86E−04 | 5.16E−10 | 14.7 | 42 | 19 |
| 5.1 | 3A5.299 | | VL_V97Q | 48.5 | 5.86E+05 | 9.90E−05 | 1.69E−10 | 15.5 | 120 | 71 |
| 5.1 | 3A5.462 | | VH_S56H | 50 | 6.35E+05 | 1.16E−04 | 1.83E−10 | 15.9 | 103 | 41 |
| 5.1 | 3A5.466 | | VH_T57L | 44.9 | 6.39E+05 | 1.02E−04 | 1.59E−10 | 14.2 | 117 | 14 |
| 5.1 | 3A5.483 | | VH_A93Y | 38.2 | | | | | NB | 8 |
| 5.1 | 3A5.503 | | VH_L95Q | 48.5 | 4.04E+05 | 6.18E−04 | 1.53E−09 | 14.4 | 19 | 18 |
| 5.1 | 3A5.163 | | VL_S52D | 49.3 | 6.65E+05 | 1.01E−04 | 1.52E−10 | 16.4 | 118 | 177 |
| 5.1 | 3A5.164 | | VL_S52Q | 49.6 | 6.57E+05 | 1.17E−04 | 1.78E−10 | 15.8 | 102 | 9.8 |
| 5.1 | 3A5.166 | | VL_S52H | 51.6 | 6.71E+05 | 1.11E−04 | 1.66E−10 | 16.9 | 107 | 167 |
| 5.1 | 3A5.167 | | VL_S52W | 52.3 | 7.19E+05 | 1.11E−04 | 1.55E−10 | 17.2 | 107 | 166 |
| 5.1 | 3A5.169 | | VL_D53S | 50.6 | 6.38E+05 | 6.35E−05 | 9.97E−11 | 16.5 | 187 | 151 |
| 5.1 | 3A5.170 | | VL_D53L | 48.8 | 6.87E+05 | 9.50E−05 | 1.38E−10 | 15.8 | 125 | 143 |
| 5.1 | 3A5.171 | | VL_D53Y | 51 | 6.79E+05 | 1.09E−04 | 1.60E−10 | 16.1 | 109 | 208 |
| 5.1 | 3A5.173 | | VL_D53K | 52.6 | 6.35E+05 | 1.09E−04 | 1.71E−10 | 16.7 | 109 | 175 |
| 5.1 | 3A5.175 | | VL_D53W | 50 | 5.88E+05 | 9.74E−05 | 1.66E−10 | 15.7 | 122 | 178 |
| 5.1 | 3A5.176 | | VL_R54A | 50.4 | 6.51E+05 | 9.75E−05 | 1.50E−10 | 16.8 | 122 | 138 |
| 5.1 | 3A5.177 | | VL_R54S | 50.1 | 6.45E+05 | 1.11E−04 | 1.72E−10 | 16.8 | 107 | 131 |
| 5.1 | 3A5.178 | | VL_R54L | 51.5 | 6.60E+05 | 1.01E−04 | 1.53E−10 | 17 | 118 | 135 |
| 5.1 | 3A5.179 | | VL_R54Y | 49.2 | 6.66E+05 | 1.24E−04 | 1.86E−10 | 16.4 | 96 | 138 |
| 5.1 | 3A5.180 | | VL_R54D | 49.5 | 6.79E+05 | 9.89E−05 | 1.46E−10 | 16.6 | 120 | 128 |
| 5.1 | 3A5.181 | | VL_R54Q | 51.3 | 6.58E+05 | 9.55E−05 | 1.45E−10 | 17 | 125 | 148 |
| 5.1 | 3A5.182 | | VL_R54K | 51.5 | 6.50E+05 | 1.17E−04 | 1.79E−10 | 17 | 102 | 165 |
| 5.1 | 3A5.183 | | VL_R54H | 49.1 | 6.47E+05 | 8.44E−05 | 1.30E−10 | 16.3 | 141 | 137 |
| 5.1 | 3A5.184 | | VL_R54W | 50 | 6.14E+05 | 1.22E−04 | 1.99E−10 | 15.8 | 98 | 7.5 |
| 5.1 | 3A5.185 | | VL_P55A | 51.9 | 6.87E+05 | 1.34E−04 | 1.95E−10 | 16.5 | 89 | 8.9 |
| 5.1 | 3A5.187 | | VL_P55L | 49.6 | 7.00E+05 | 9.58E−05 | 1.37E−10 | 16.3 | 124 | 153 |
| 5.1 | 3A5.188 | | VL_P55Y | 49.2 | 6.61E+05 | 1.19E−04 | 1.80E−10 | 16.4 | 100 | 127 |
| 5.1 | 3A5.189 | | VL_P55D | 51.1 | 6.48E+05 | 9.21E−05 | 1.42E−10 | 16.7 | 129 | 155 |
| 5.1 | 3A5.190 | | VL_P55Q | 48.8 | 6.55E+05 | 1.08E−04 | 1.64E−10 | 16.4 | 110 | 151 |
| 5.1 | 3A5.191 | | VL_P55K | 49.3 | 6.38E+05 | 1.05E−04 | 1.64E−10 | 16.3 | 113 | 137 |
| 5.1 | 3A5.192 | | VL_P55H | 51.5 | 6.51E+05 | 1.16E−04 | 1.78E−10 | 16.7 | 103 | 176 |
| 5.1 | 3A5.193 | | VL_P55W | 51.5 | 6.41E+05 | 8.80E−05 | 1.37E−10 | 16.8 | 135 | 160 |
| 5.1 | 3A5.194 | | VL_S56A | 49.8 | 6.41E+05 | 1.06E−04 | 1.65E−10 | 16.1 | 112 | 143 |
| 5.1 | 3A5.195 | | VL_S56L | 49.6 | 6.85E+05 | 1.06E−04 | 1.54E−10 | 16.3 | 112 | 131 |
| 5.1 | 3A5.196 | | VL_S56Y | 50.2 | 6.89E+05 | 1.14E−04 | 1.66E−10 | 16.5 | 104 | 123 |
| 5.1 | 3A5.197 | | VL_S56D | 50.1 | 6.87E+05 | 1.19E−04 | 1.73E−10 | 16.5 | 100 | 153 |
| 5.1 | 3A5.198 | | VL_S56Q | 49.6 | 6.86E+05 | 8.85E−05 | 1.29E−10 | 16.4 | 134 | 131 |
| 5.1 | 3A5.200 | | VL_S56H | 49.3 | 6.83E+05 | 1.15E−04 | 1.68E−10 | 16.3 | 103 | 138 |
| 5.1 | 3A5.207 | | VL_Q89K | 49.9 | 6.84E+05 | 1.27E−04 | 1.86E−10 | 16.4 | 94 | 136 |
| 5.1 | 3A5.209 | | VL_Q89W | 48.6 | 5.57E+05 | 1.27E−04 | 2.28E−10 | 15.7 | 94 | 72 |
| 5.1 | 3A5.278 | | VL_H95bY | 49.9 | 7.65E+05 | 7.90E−05 | 1.03E−10 | 16.3 | 151 | 139 |
| 5.1 | 3A5.279 | | VL_H95bD | 49.6 | 7.01E+05 | 7.84E−05 | 1.12E−10 | 16.5 | 152 | 210 |
| 5.1 | 3A5.280 | | VL_H95bQ | 50.3 | 7.47E+05 | 1.51E−04 | 2.02E−10 | 16.6 | 79 | 133 |
| 5.1 | 3A5.284 | | VL_V96A | 48.2 | 7.24E+05 | 1.88E−04 | 2.60E−10 | 15.9 | 63 | 65 |
| 5.1 | 3A5.286 | | VL_V96L | 48.4 | 6.50E+05 | 1.94E−04 | 2.98E−10 | 15.9 | 61 | 79 |
| 5.1 | 3A5.294 | | VL_V97A | 48.6 | 6.27E+05 | 7.68E−05 | 1.23E−10 | 16 | 155 | 133 |
| 5.1 | 3A5.295 | | VL_V97S | 48.6 | 6.12E+05 | 1.07E−04 | 1.74E−10 | 15.9 | 111 | 110 |
| 5.1 | 3A5.296 | | VL_V97L | 48 | 6.71E+05 | 9.60E−05 | 1.43E−10 | 15.9 | 124 | 95 |
| 5.1 | 3A5.297 | | VL_V97Y | 48.4 | 6.72E+05 | 1.07E−04 | 1.60E−10 | 16.2 | 111 | 90 |
| 5.1 | 3A5.298 | | VL_V97D | 47.7 | 5.94E+05 | 1.30E−04 | 2.18E−10 | 15.8 | 92 | 96 |
| 5.1 | 3A5.300 | | VL_V97K | 50.1 | 5.88E+05 | 1.18E−04 | 2.01E−10 | 15.8 | 101 | 4.7 |
| 5.1 | 3A5.301 | | VL_V97H | 49.4 | 6.34E+05 | 8.79E−05 | 1.39E−10 | 16.1 | 135 | 168 |
| 5.1 | 3A5.063 | | VL_G25K | 49 | 6.90E+05 | 7.21E−05 | 1.05E−10 | 16.2 | 165 | 90 |
| 5.1 | 3A5.067 | | VL_N26S | 49 | 6.52E+05 | 1.10E−04 | 1.69E−10 | 16 | 108 | 162 |
| 5.1 | 3A5.083 | | VL_N27W | 49.6 | 6.03E+05 | 1.29E−04 | 2.14E−10 | 16.4 | 92 | 148 |
| 5.1 | 3A5.091 | | VL_I28H | 47.7 | 5.71E+05 | 1.30E−04 | 2.27E−10 | 15.7 | 92 | 75 |
| 5.1 | 3A5.098 | | VL_G29Q | 49.7 | 6.53E+05 | 1.05E−04 | 1.61E−10 | 16.2 | 113 | 139 |
| 5.1 | 3A5.108 | | VL_S30H | 49.4 | 6.95E+05 | 1.02E−04 | 1.46E−10 | 16.2 | 117 | 145 |
| 5.1 | 3A5.109 | | VL_S30W | 48 | 6.77E+05 | 1.35E−04 | 2.00E−10 | 15.5 | 88 | 112 |
| 5.1 | 3A5.119 | | VL_N32S | 48.6 | 8.35E+05 | 1.08E−04 | 1.29E−10 | 16.3 | 110 | 98 |
| 5.1 | 3A5.120 | | VL_N32L | 49.2 | 8.72E+05 | 1.03E−04 | 1.18E−10 | 16.4 | 116 | 119 |
| 5.1 | 3A5.129 | | VL_V33L | 48.8 | 5.80E+05 | 1.42E−04 | 2.45E−10 | 15.8 | 84 | 99 |
| 5.1 | 3A5.277 | | VL_H95bL | 50.4 | 6.79E+05 | 1.40E−04 | 2.06E−10 | 16.6 | 85 | 180 |

TABLE 3-continued

Determination of supernatant 3A5.040 variant antibody titre and IL-5 binding kinetics by Biacore

| Run # | Antibody ID | Replicate Number | Amino acid Substitution | Capture level | ka (1/Ms) | kd (1/s) | $K_D$ (M) | Rmax (RU) | % 3A5.040 kd | % 3A5.040 titre |
|---|---|---|---|---|---|---|---|---|---|---|
| 5.1 | 3A5.302 | | VL_V97W | 47.7 | 7.18E+05 | 7.59E−05 | 1.06E−10 | 15.9 | 157 | 73 |
| 5.1 | 3A5.303 | | VL_V97P | 48.7 | 6.99E+05 | 1.21E−04 | 1.73E−10 | 16.2 | 98 | 21 |

This table contains a summary of the calculated kinetic and titre data for each antibody supernatant tested.
Variant antibodies with a lower kd (slower off-rate) than parent 3A5.040 antibody have a "% 3A5.040 kd" value >100% and those with a higher kd (faster off-rate) a value <100%.
Variant antibodies with a higher titre than parent 3A5.040 antibody have a "% 3A5.040 titre" value >100% and those with a lower titre, a value <100%.
N/A, non-applicable.
NB, No binding.
NE, No expression.

TABLE 4

Determination of purified 3A5.040 variant antibody IL-5 binding kinetics by Biacore

| Run # | Antibody ID | Replicates | Amino acid Substitution | Capture level | ka (1/Ms) | kd (1/s) | KD (M) | Rmax (RU) | % 3A5.040 kd |
|---|---|---|---|---|---|---|---|---|---|
| 6 | 3A5.040 (batch 6) | 1 | Wild type | 48.6 | 1.44E+06 | 2.32E−04 | 1.61E−10 | 16 | |
| 6 | 3A5.040 (batch 6) | 2 | Wild type | 49.4 | 1.44E+06 | 2.14E−04 | 1.48E−10 | 15.7 | |
| 6 | 3A5.040 (batch 6) | 3 | Wild type | 49.2 | 1.36E+06 | 2.61E−04 | 1.93E−10 | 16 | |
| 6 | 3A5.040 (batch 6) | 4 | Wild type | 49.2 | 1.36E+06 | 2.46E−04 | 1.80E−10 | 16 | |
| 6 | 3A5.040 (batch 6) | 5 | Wild type | 49.3 | 1.47E+06 | 2.52E−04 | 1.71E−10 | 16.1 | |
| 6 | 3A5.040 (batch 6) | 6 | Wild type | 49.2 | 1.45E+06 | 2.13E−04 | 1.47E−10 | 16 | |
| 6 | 3A5.040 (batch 6) | 7 | Wild type | 49.2 | 1.41E+06 | 2.29E−04 | 1.63E−10 | 16.1 | |
| 6 | 3A5.040 (batch 6) | 8 | Wild type | 50.9 | 1.40E+06 | 2.45E−04 | 1.75E−10 | 16.8 | |
| 6 | 3A5.040 (batch 6) | Average | Wild type | 49.3 | 1.42E+06 | 2.37E−04 | 1.67E−10 | 16.1 | 100 |
| 6 | IgG4 iso | 1 | | 48.8 | N/A | N/A | N/A | 0 | |
| 6 | IgG4 iso | 2 | | 48.9 | N/A | N/A | N/A | 0 | |
| 6 | IgG4 iso | 3 | | 48.8 | N/A | N/A | N/A | 0 | |
| 6 | IgG4 Isotype | Average | | 49.8 | N/A | N/A | N/A | 0 | N/A |
| 6 | 3A5.040 (Purified) | 1 | Wild type | 49.6 | 1.43E+06 | 2.39E−04 | 1.68E−10 | 16.1 | |
| 6 | 3A5.040 (Purified) | 2 | Wild type | 49.8 | 1.48E+06 | 2.85E−04 | 1.93E−10 | 16.2 | |
| 6 | 3A5.040 (Purified) | 3 | Wild type | 49.7 | 1.45E+06 | 2.32E−04 | 1.60E−10 | 16.1 | |
| 6 | 3A5.040 (Purified) | Average | Wild type | 49.7 | 1.45E+06 | 2.52E−04 | 1.74E−10 | 16.1 | 94 |
| 6 | 3A5.237 | 1 | VL_D92W | 47.9 | 1.57E+06 | 2.67E−04 | 1.70E−10 | 15.5 | |
| 6 | 3A5.237 | 2 | VL_D92W | 48.7 | 1.55E+06 | 2.58E−04 | 1.66E−10 | 15.6 | |
| 6 | 3A5.237 | 3 | VL_D92W | 48.5 | 1.52E+06 | 2.12E−04 | 1.40E−10 | 15.7 | |
| 6 | 3A5.237 | Average | VL_D92W | 48.3 | 1.55E+06 | 2.46E−04 | 1.59E−10 | 15.6 | 96 |
| 6 | 3A5.161 | 1 | VL_S52L | 49.4 | 1.47E+06 | 2.62E−04 | 1.78E−10 | 16.2 | |
| 6 | 3A5.161 | 2 | VL_S52L | 49.9 | 1.43E+06 | 2.41E−04 | 1.69E−10 | 16.2 | |
| 6 | 3A5.161 | 3 | VL_S52L | 49.9 | 1.40E+06 | 2.19E−04 | 1.57E−10 | 16.4 | |
| 6 | 3A5.161 | Average | VL_S52L | 49.7 | 1.43E+06 | 2.41E−04 | 1.68E−10 | 16.2 | 99 |
| 6 | 3A5.169 | 1 | VL_D53S | 48.9 | 1.23E+06 | 2.43E−04 | 1.98E−10 | 15.6 | |
| 6 | 3A5.169 | 2 | VL_D53S | 49.5 | 1.26E+06 | 2.44E−04 | 1.93E−10 | 15.9 | |
| 6 | 3A5.169 | 3 | VL_D53S | 49.7 | 1.23E+06 | 2.46E−04 | 1.99E−10 | 16.1 | |
| 6 | 3A5.169 | Average | VL_D53S | 49.3 | 1.24E+06 | 2.44E−04 | 1.97E−10 | 15.8 | 97 |
| 6 | 3A5.183 | 1 | VL_R54H | 47.9 | 1.44E+06 | 2.32E−04 | 1.61E−10 | 15.6 | |
| 6 | 3A5.183 | 2 | VL_R54H | 48.2 | 1.44E+06 | 2.50E−04 | 1.74E−10 | 15.8 | |
| 6 | 3A5.183 | 3 | VL_R54H | 48.4 | 1.39E+06 | 2.04E−04 | 1.47E−10 | 15.8 | |
| 6 | 3A5.183 | Average | VL_R54H | 48.1 | 1.42E+06 | 2.29E−04 | 1.61E−10 | 15.7 | 104 |
| 6 | 3A5.193 | 1 | VL_P55W | 48.5 | 1.32E+06 | 2.32E−04 | 1.76E−10 | 15.7 | |
| 6 | 3A5.193 | 2 | VL_P55W | 48.3 | 1.34E+06 | 2.51E−04 | 1.88E−10 | 15.3 | |
| 6 | 3A5.193 | 3 | VL_P55W | 48.7 | 1.29E+06 | 2.57E−04 | 1.99E−10 | 15.6 | |
| 6 | 3A5.193 | Average | VL_P55W | 48.5 | 1.32E+06 | 2.47E−04 | 1.88E−10 | 15.5 | 96 |
| 6 | 3A5.198 | 1 | VL_S56Q | 49.1 | 1.42E+06 | 2.43E−04 | 1.71E−10 | 16 | |
| 6 | 3A5.198 | 2 | VL_S56Q | 49 | 1.49E+06 | 2.90E−04 | 1.95E−10 | 15.7 | |
| 6 | 3A5.198 | 3 | VL_S56Q | 49.3 | 1.42E+06 | 2.38E−04 | 1.68E−10 | 15.9 | |
| 6 | 3A5.198 | Average | VL_S56Q | 49.1 | 1.44E+06 | 2.57E−04 | 1.78E−10 | 15.8 | 92 |
| 6 | 3A5.278 | 1 | VL_H95bY | 48.3 | 1.55E+06 | 2.53E−04 | 1.63E−10 | 15.9 | |
| 6 | 3A5.278 | 2 | VL_H95bY | 48.2 | 1.62E+06 | 2.43E−04 | 1.49E−10 | 15.7 | |
| 6 | 3A5.278 | 3 | VL_H95bY | 48.5 | 1.57E+06 | 2.14E−04 | 1.36E−10 | 15.8 | |
| 6 | 3A5.278 | Average | VL_H95bY | 48.3 | 1.58E+06 | 2.37E−04 | 1.49E−10 | 15.8 | 100 |
| 6 | 3A5.279 | 1 | VL_H95bD | 50 | 1.58E+06 | 2.50E−04 | 1.58E−10 | 16.3 | |
| 6 | 3A5.279 | 2 | VL_H95bD | 49.7 | 1.61E+06 | 2.42E−04 | 1.50E−10 | 16.1 | |
| 6 | 3A5.279 | 3 | VL_H95bD | 50 | 1.61E+06 | 2.43E−04 | 1.51E−10 | 16.4 | |
| 6 | 3A5.279 | Average | VL_H95bD | 49.9 | 1.60E+06 | 2.45E−04 | 1.53E−10 | 16.2 | 97 |
| 6 | 3A5.294 | 1 | VL_V97A | 49.1 | 1.31E+06 | 2.54E−04 | 1.94E−10 | 15.9 | |
| 6 | 3A5.294 | 2 | VL_V97A | 48.6 | 1.31E+06 | 2.13E−04 | 1.62E−10 | 15.7 | |
| 6 | 3A5.294 | 3 | VL_V97A | 48.6 | 1.37E+06 | 2.15E−04 | 1.57E−10 | 15.6 | |
| 6 | 3A5.294 | Average | VL_V97A | 48.7 | 1.33E+06 | 2.27E−04 | 1.71E−10 | 15.7 | 104 |
| 6 | 3A5.301 | 1 | VL_V97H | 48.4 | 1.51E+06 | 2.76E−04 | 1.83E−10 | 15.8 | |

TABLE 4-continued

Determination of purified 3A5.040 variant antibody IL-5 binding kinetics by Biacore

| Run # | Antibody ID | Replicates | Amino acid Substitution | Capture level | ka (1/Ms) | kd (1/s) | KD (M) | Rmax (RU) | % 3A5.040 kd |
|---|---|---|---|---|---|---|---|---|---|
| 6 | 3A5.301 | 2 | VL_V97H | 48.1 | 1.58E+06 | 1.06E−04 | 6.71E−11 | 15.6 | |
| 6 | 3A5.301 | 3 | VL_V97H | 47.8 | 1.60E+06 | 2.45E−04 | 1.53E−10 | 15.4 | |
| 6 | 3A5.301 | Average | VL_V97H | 48.1 | 1.56E+06 | 2.09E−04 | 1.34E−10 | 15.6 | 114 |
| 6 | 3A5.063 | 1 | VL_G25K | 48 | 1.37E+06 | 2.61E−04 | 1.90E−10 | 15.7 | |
| 6 | 3A5.063 | 2 | VL_G25K | 48.1 | 1.36E+06 | 2.70E−04 | 1.99E−10 | 15.5 | |
| 6 | 3A5.063 | 3 | VL_G25K | 47.8 | 1.42E+06 | 2.50E−04 | 1.76E−10 | 15.3 | |
| 6 | 3A5.063 | Average | VL_G25K | 47.9 | 1.38E+06 | 2.60E−04 | 1.88E−10 | 15.5 | 91 |
| 6 | 3A5.302 | 1 | VL_V97W | 48.9 | 1.65E+06 | 2.35E−04 | 1.42E−10 | 16 | |
| 6 | 3A5.302 | 2 | VL_V97W | 48.9 | 1.69E+06 | 2.35E−04 | 1.39E−10 | 15.8 | |
| 6 | 3A5.302 | 3 | VL_V97W | 48.5 | 1.66E+06 | 2.40E−04 | 1.45E−10 | 15.7 | |
| 6 | 3A5.302 | Average | VL_V97W | 48.7 | 1.67E+06 | 2.37E−04 | 1.42E−10 | 15.8 | 100 |
| 6 | 3A5.202 | 1 | VL_Q89A | 48.9 | 1.09E+06 | 2.49E−04 | 2.29E−10 | 15.8 | |
| 6 | 3A5.202 | 2 | VL_Q89A | 48.7 | 1.07E+06 | 1.89E−04 | 1.77E−10 | 15.6 | |
| 6 | 3A5.202 | 3 | VL_Q89A | 48.8 | 1.09E+06 | 2.44E−04 | 2.25E−10 | 15.7 | |
| 6 | 3A5.202 | Average | VL_Q89A | 48.8 | 1.08E+06 | 2.27E−04 | 2.10E−10 | 15.7 | 104 |
| 6 | 3A5.203 | 1 | VL_Q89S | 49 | 1.28E+06 | 2.82E−04 | 2.20E−10 | 15.9 | |
| 6 | 3A5.203 | 2 | VL_Q89S | 48.6 | 1.28E+06 | 2.26E−04 | 1.76E−10 | 15.6 | |
| 6 | 3A5.203 | 3 | VL_Q89S | 48.9 | 1.27E+06 | 2.36E−04 | 1.86E−10 | 15.7 | |
| 6 | 3A5.203 | Average | VL_Q89S | 48.8 | 1.28E+06 | 2.48E−04 | 1.94E−10 | 15.7 | 96 |
| 6 | 3A5.204 | 1 | VL_Q89L | 49.9 | 5.01E+05 | 2.20E−04 | 4.38E−10 | 14.4 | |
| 6 | 3A5.204 | 2 | VL_Q89L | 49.9 | 5.02E+05 | 1.88E−04 | 3.74E−10 | 14.2 | |
| 6 | 3A5.204 | 3 | VL_Q89L | 49.9 | 4.95E+05 | 2.11E−04 | 4.26E−10 | 14.3 | |
| 6 | 3A5.204 | Average | VL_Q89L | 49.9 | 4.99E+05 | 2.06E−04 | 4.13E−10 | 14.3 | 115 |
| 6 | 3A5.205 | 1 | VL_Q89Y | 48.4 | 9.87E+05 | 2.42E−04 | 2.45E−10 | 15.5 | |
| 6 | 3A5.205 | 2 | VL_Q89Y | 48.6 | 1.04E+06 | 2.37E−04 | 2.28E−10 | 15.6 | |
| 6 | 3A5.205 | 3 | VL_Q89Y | 48.5 | 1.05E+06 | 2.60E−04 | 2.47E−10 | 15.6 | |
| 6 | 3A5.205 | Average | VL_Q89Y | 48.5 | 1.03E+06 | 2.46E−04 | 2.40E−10 | 15.5 | 96 |
| 6 | 3A5.208 | 1 | VL_Q89H | 51 | 9.41E+05 | 2.53E−04 | 2.68E−10 | 16 | |
| 6 | 3A5.208 | 2 | VL_Q89H | 51.1 | 9.45E+05 | 2.52E−04 | 2.66E−10 | 16.1 | |
| 6 | 3A5.208 | 3 | VL_Q89H | 51 | 9.54E+05 | 2.88E−04 | 3.02E−10 | 16 | |
| 6 | 3A5.208 | Average | VL_Q89H | 51 | 9.47E+05 | 2.64E−04 | 2.79E−10 | 16 | 90 |
| 6 | 3A5.550 | 1 | VH_D101Y | 48.3 | 1.16E+06 | 4.40E−04 | 3.81E−10 | 15.5 | |
| 6 | 3A5.550 | 2 | VH_D101Y | 48.5 | 1.17E+06 | 4.54E−04 | 3.87E−10 | 15.7 | |
| 6 | 3A5.550 | 3 | VH_D101Y | 48.3 | 1.19E+06 | 4.86E−04 | 4.10E−10 | 15.5 | |
| 6 | 3A5.550 | Average | VH_D101Y | 48.3 | 1.17E+06 | 4.60E−04 | 3.93E−10 | 15.5 | 51 |
| 6 | 3A5.512 | 1 | VH_G96D | 50.4 | 1.70E+07 | 8.63E−03 | 5.07E−10 | 13.7 | |
| 6 | 3A5.512 | 2 | VH_G96D | 50.7 | 1.88E+07 | 9.87E−03 | 5.26E−10 | 13.8 | |
| 6 | 3A5.512 | 3 | VH_G96D | 50.5 | 1.28E+06 | 1.52E−03 | 1.19E−09 | 12.5 | |
| 6 | 3A5.512 | Average | VH_G96D | 50.5 | 1.24E+07 | 6.67E−03 | 7.41E−10 | 13.3 | 3.5 |
| 6 | 3A5.124 | 1 | VL_N32K | 50.9 | 9.94E+05 | 2.46E−04 | 2.47E−10 | 16.3 | |
| 6 | 3A5.124 | 2 | VL_N32K | 51.2 | 1.05E+06 | 2.62E−04 | 2.49E−10 | 16.5 | |
| 6 | 3A5.124 | 3 | VL_N32K | 50.7 | 1.02E+06 | 2.28E−04 | 2.24E−10 | 16.3 | |
| 6 | 3A5.124 | Average | VL_N32K | 50.9 | 1.02E+06 | 2.45E−04 | 2.40E−10 | 16.3 | 97 |
| 7 | 3A5.040 (batch 7) | 1 | Wild type | 51.2 | 1.37E+06 | 2.30E−04 | 1.68E−10 | 16.4 | |
| 7 | 3A5.040 (batch 7) | 2 | Wild type | 51.6 | 1.43E+06 | 2.15E−04 | 1.50E−10 | 16.6 | |
| 7 | 3A5.040 (batch 7) | 3 | Wild type | 51.6 | 1.42E+06 | 2.84E−04 | 2.00E−10 | 16.6 | |
| 7 | 3A5.040 (batch 7) | Average | Wild type | 51.4 | 1.41E+06 | 2.43E−04 | 1.73E−10 | 16.5 | 100 |
| 7 | IgG4 Isotype | 1 | | 48.8 | N/A | N/A | N/A | 0 | |
| 7 | IgG4 Isotype | 2 | | 48.9 | N/A | N/A | N/A | 0 | |
| 7 | IgG4 Isotype | 3 | | 48.8 | N/A | N/A | N/A | 0 | |
| 7 | IgG4 Isotype | Average | | 49.8 | N/A | N/A | N/A | 0 | N/A |
| 7 | 3A5.040 (Purified) | 1 | Wild type | 49.6 | 1.43E+06 | 2.39E−04 | 1.68E−10 | 16.1 | |
| 7 | 3A5.040 (Purified) | 2 | Wild type | 49.8 | 1.48E+06 | 2.85E−04 | 1.93E−10 | 16.2 | |
| 7 | 3A5.040 (Purified) | 3 | Wild type | 49.7 | 1.45E+06 | 2.32E−04 | 1.60E−10 | 16.1 | |
| 7 | 3A5.040 (Purified) | Average | Wild type | 49.7 | 1.45E+06 | 2.52E−04 | 1.74E−10 | 16.1 | 94 |
| 7 | 3A5.068 | 1 | VL_N26L | 52.3 | 1.29E+06 | 2.68E−04 | 2.07E−10 | 16.8 | |
| 7 | 3A5.068 | 2 | VL_N26L | 53 | 1.39E+06 | 2.08E−04 | 1.50E−10 | 17.1 | |
| 7 | 3A5.068 | 3 | VL_N26L | 53.1 | 1.43E+06 | 2.69E−04 | 1.88E−10 | 17.2 | |
| 7 | 3A5.068 | Average | VL_N26L | 52.8 | 1.37E+06 | 2.48E−04 | 1.82E−10 | 17 | 98 |
| 7 | 3A5.079 | 1 | VL_N27D | 49.3 | 1.22E+06 | 2.29E−04 | 1.88E−10 | 16.1 | |
| 7 | 3A5.079 | 2 | VL_N27D | 50 | 1.29E+06 | 2.39E−04 | 1.85E−10 | 16.4 | |
| 7 | 3A5.079 | 3 | VL_N27D | 49.9 | 1.25E+06 | 2.63E−04 | 2.09E−10 | 16.2 | |
| 7 | 3A5.079 | Average | VL_N27D | 49.7 | 1.25E+06 | 2.44E−04 | 1.94E−10 | 16.2 | 100 |

This table contains a summary of the calculated kinetic data for each purified antibody tested.
Variant antibodies with a lower kd (slower off-rate) than parent 3A5.040 antibody have a "% 3A5.040 kd" value >100% and those with a higher kd (faster off-rate) a value <100%.
Runs 6 and 7 were transfected separately but run in the same biacore batch, and therefore use the same isotype and 3A5.040 (purified) controls.
N/A: non-applicable.

TABLE 5

Purified protein expression yield for selected 3A5.040 antibody variants

| Run # | Antibody ID | Amino acid Substitution | % parent 3A5.040 purified yield |
|---|---|---|---|
| 6 | 3A5.040 | Parental sequence | 100 |
| 6 | 3A5.237 | VL_D92W | 89 |
| 6 | 3A5.161 | VL_S52L | 160 |
| 6 | 3A5.169 | VL_D53S | 173 |
| 6 | 3A5.183 | VL_R54H | 172 |
| 6 | 3A5.193 | VL_P55W | 187 |
| 6 | 3A5.198 | VL_S56Q | 205 |
| 6 | 3A5.278 | VL_H95bY | 210 |
| 6 | 3A5.279 | VL_H95bD | 143 |
| 6 | 3A5.294 | VL_V97A | 140 |
| 6 | 3A5.301 | VL_V97H | 151 |
| 6 | 3A5.063 | VL_G25K | 110 |
| 6 | 3A5.302 | VL_V97W | 156 |
| 6 | 3A5.202 | VL_Q89A | 64 |
| 6 | 3A5.203 | VL_Q89S | 129 |
| 6 | 3A5.204 | VL_Q89L | 61 |
| 6 | 3A5.205 | VL_Q89Y | 41 |
| 6 | 3A5.208 | VL_Q89H | 54 |
| 6 | 3A5.550 | VH_D101Y | 88 |
| 6 | 3A5.512 | VH_G96D | 72 |
| 6 | 3A5.124 | VL_N32K | 128 |
| 7 | 3A5.040 | Parental Sequence | 100 |
| 7 | 3A5.068 | VL_N26L | 96 |
| 7 | 3A5.079 | VL_N27D | 99 |

TABLE 6

VH CDR1 Scanning Matrix

| sc | 26 G | | 27 G | | 28 S | | 29 I | | 30 S | | 31 N | | 32 G | | 33 G | | 34 Y | | 35 Y | | 35A W | | 35B S | |
|---|---|---|---|---|---|---|---|---|---|---|---|---|---|---|---|---|---|---|---|---|---|---|---|---|
| A | 0.5 | 1.3 | 1 | | 0.8 | 0.6 | 0.9 | 0.3 | 0.6 | 0.1 | 1.1 | 1.2 | 0.1 | 1.8 | 0.3 | 1.2 | 1.3 | 1.6 | 0.7 | 2.9 | 0 | 0.4 | 0.1 | 0.9 | 1 |
| S | 0.6 | 0.9 | 1 | 1 | — | — | 0.3 | 0.5 | — | — | 1.1 | 0.2 | 1.5 | 0.1 | 1.2 | 0 | 1.6 | 0.7 | 1.3 | 0 | 0.2 | 0.1 | — | — |
| L | 0.2 | 1.1 | 1.2 | 0.8 | 0.7 | 1.1 | 0.8 | 0.9 | 1.5 | 0.7 | 0.7 | 0.2 | 0.8 | 0 | 0.8 | 0.4 | 1.6 | 0.6 | 1.9 | 0.1 | 1 | 0.1 | 0.4 | 0.3 |
| Y | 0.6 | 1.1 | 0.8 | 0.1 | 0.5 | 1.2 | 0.2 | 0.1 | 1 | 0.7 | 0.6 | 0.1 | 0.9 | 0 | 1.1 | 0 | — | — | — | 1 | 0.5 | 0.9 | 0 | |
| D | 0.6 | 1.2 | 0.7 | 0.9 | 0.7 | 1.1 | 0.2 | 0 | 1 | 0.8 | 0.8 | 0.5 | 1.1 | 0 | 2.8 | 0 | 1 | 0.2 | 0.9 | 0 | NE | NE | 0.2 | 0.9 |
| Q | 0.9 | 1.1 | 0.8 | 0.7 | 0.8 | 1 | 0.4 | 0.3 | 1.2 | 1.1 | 1.6 | 0.2 | 1.3 | 0.1 | 2.8 | 0.1 | 1.7 | 0.6 | 1.3 | 0 | 0.3 | 0.1 | 0.5 | 0.2 |
| K | 1 | 1 | 1 | 0.5 | 0.8 | 0.9 | 0.3 | 0.1 | 1.6 | 0.8 | 1.7 | 0.1 | 1.7 | 0 | 3.5 | 0 | 4.1 | 0.2 | 3.8 | NB | 0.3 | 0.1 | 0.1 | 0 |
| H | 0.9 | 0.9 | 0.7 | 0.4 | 0.7 | 0.8 | 0.2 | 0.1 | 0.8 | 0.8 | 1.4 | 0.8 | 1.1 | 0 | 2.7 | 0 | 2.2 | 0.1 | 2 | 0 | 0.5 | 0.4 | 0.8 | 0 |
| W | 1.1 | 0.8 | 1 | | 0.2 | 0.4 | 0.7 | 0.4 | 0 | 0.7 | 0.9 | 0.6 | 0.2 | 0.7 | 0 | 1.7 | 0.1 | 0.5 | 0.5 | 2.3 | 0 | — | — | 0.5 | 0 |
| P | — | | — | | — | | — | | — | | — | | — | | — | | — | | — | | — | | — | |

Summary of difference in 3A5.040 variant antibody titre and kd for variants of VH CDR1 (AbM definition). Kabat amino acid numbering and parent 3A5.040 amino acids are given in the top row. Mutated residue identities are listed in the left column. The leftmost value in each cell is the proportional titre of each variant vs parent 3A5.040 (>1 = higher titre, <1 = lower titre), while the right value is the proportional kd (>1 = lower kd, <1 = higher kd) of each variant vs parent 3A5.040. Variants not made are blank. NB, no binding. NE, no expression. (VH CDR1 sequence disclosed as residues 26-37 of SEQ ID NO: 73).

TABLE 7

VH CDR2 Scanning Matrix

| sc | 50 Y | | 51 I | | 52 Y | | 53 Y | | 54 S | | 55 G | | 56 S | | 57 T | | 58 Y | |
|---|---|---|---|---|---|---|---|---|---|---|---|---|---|---|---|---|---|---|
| A | 2.7 | 0.2 | 2.4 | 0.8 | 3 | 0 | 2.5 | 0.2 | 1.1 | 0.6 | 0.7 | 0.9 | 1 | 0.9 | 1 | 0.8 | 1 | 0 |
| S | 3.3 | 0.2 | 1.3 | 0.8 | 3.3 | 0.1 | 2.3 | 0.6 | — | — | 0.7 | 0.7 | — | — | 0.7 | 0.8 | 1 | 0 |
| L | 1.2 | 0.3 | 0.9 | 0.7 | 2.1 | 0 | 1 | 0.2 | 1.6 | 0 | 0.7 | 0.1 | 1 | 1.2 | 0.1 | 1.2 | 0.7 | 0 |
| Y | — | — | 1.1 | 0 | — | — | — | — | 0.9 | 0 | 0.5 | 0.1 | 0.9 | 0.5 | 0.5 | 1.1 | — | — |
| D | 1.7 | 0.1 | 0.5 | 0.1 | 3.3 | NB | 1.8 | 0.2 | 2 | 0 | 0.4 | 0.4 | 0.8 | 0.2 | 0.5 | 1.1 | 0.5 | 0 |
| Q | 2.4 | 0.2 | 1 | 0.2 | 2.6 | 0 | 2.1 | 0.2 | 1.5 | 0.1 | 0.4 | 0.5 | 1.1 | 1.1 | 0.6 | 1 | 0.8 | 0.1 |
| K | 1.4 | 0.2 | 1.2 | 0.1 | 3.5 | NB | 2.3 | 0.1 | 2 | 0 | 0.5 | 0.5 | 1.2 | 1.3 | 0.6 | 0.9 | 1 | 0.1 |
| H | 3 | 0.1 | 0.9 | 0 | 2.9 | 0.3 | 2.1 | 0.5 | 1 | 0.2 | 0.4 | 0.6 | 0.4 | 1 | 0.5 | 1 | 0.9 | 0.2 |
| W | 1.3 | 0.1 | 1.4 | 0 | 1 | 0.1 | 1.5 | 0.4 | 1.1 | 0.1 | 0.3 | 0.2 | 1 | 0.4 | 0.4 | 0.8 | 0.8 | 0.2 |
| P | — | | — | | — | | — | | — | | — | | — | | — | | — | |

Summary of difference in 3A5.040 variant antibody titre and kd for variants of VH CDR2 (AbM definition). Kabat amino acid numbering and parent 3A5.040 amino acids are given in the top row. Mutated residue identities are listed in the left column. The leftmost value in each cell is the proportional titre of each variant vs parent 3A5.040 (>1 = higher titre, <1 = lower titre), while the right value is the proportional kd (>1 = lower kd, <1 = higher kd) of each variant vs parent 3A5.040. Variants not made are blank. NB, no binding. NE, no expression. (VH CDR2 sequence disclosed as residues 52-60 of SEQ ID NO: 73).

TABLE 8

VH CDR3 Scanning Matrix

| | VH CDR3 | | | | | | | | | | | | | | | | |
|---|---|---|---|---|---|---|---|---|---|---|---|---|---|---|---|---|---|
| sc | 93 A | | 94 S | | 95 L | | 96 G | | 97 N | | 98 W | | 99 F | | 101 D | | 102 Y | |
| A | — | — | 1 | 1.2 | 0.5 | 0 | 0.8 | 0.8 | 1 | 0.6 | 1.1 | 0.5 | 0.4 | 0.2 | 0.7 | 0.7 | 1.1 | 1.2 |
| S | 0.6 | 1.1 | — | — | NE | NE | 0.9 | 0.5 | 0.8 | 0.5 | 0.8 | 0.4 | 0.4 | 0.1 | 0.8 | 0.9 | 1.4 | 0.9 |
| L | 0.2 | 0.5 | 0.4 | 0.1 | — | — | 0.6 | 0 | 1 | 0.9 | 0.4 | 0.6 | 0.6 | 0.9 | 0.4 | 0.2 | 0.5 | 0.9 |
| Y | 0.1 | NB | 0.3 | 0.1 | 1 | 0 | 0.6 | NB | 0.8 | 0.3 | 1.4 | 0.9 | 0.4 | 1.1 | 0.9 | 0.5 | — | — |
| D | NE | NE | NE | NE | 0.2 | NB | 0.7 | 0 | 0.9 | 0.5 | 0.4 | 1.1 | 0.3 | 0 | — | — | 0.5 | 0.7 |
| Q | 0.4 | 1 | 0.5 | 0.2 | 0.2 | 0.2 | 0.6 | 0.2 | 1.3 | 1 | 0.5 | 0.6 | 0.4 | 0.1 | 0.8 | 0.5 | 0.9 | 1 |
| K | 0.2 | NB | 1.3 | 0.3 | 0.7 | 0 | 1.5 | 0 | 1.7 | 0.7 | 0.7 | 0.1 | 0.4 | NB | 0.7 | 0.3 | 0.9 | 1.3 |
| H | 0.3 | NB | 0.7 | 0 | 0.9 | 0.1 | 1.2 | 0.1 | 1.1 | 0.5 | 0.8 | 0.7 | 0.4 | 1 | 0.7 | 0.6 | 1.3 | 1 |
| W | 0.2 | NB | 0.4 | 0.0 | 0.7 | 0 | 0.6 | 0 | 0.6 | 0.2 | — | — | 0.3 | 0.2 | 0.3 | 0.2 | 1.2 | 0.9 |
| P | 0.1 | NB | 0.2 | 0.8 | 0.4 | NB | 0.2 | 0.2 | 0.7 | 0.2 | 0.3 | 0.1 | 0.4 | NB | 0.4 | 0.1 | 0.3 | 0.8 |

Summary of difference in 3A5.040 variant antibody titre and kd for variants of VH CDR3 (AbM definition) and Kabat amino acid positions 93 and 94. Kabat amino acid numbering and parent 3A5.040 amino acids are given in the top row. Mutated residue identities are listed in the left column. The leftmost value in each cell is the proportional titre of each variant vs parent 3A5.040 (>1 = higher titre, <1 = lower titre), while the right value is the proportional kd (>1 = lower kd, <1 = higher kd) of each variant vs parent 3A5.040. Variants not made are blank. NB, no binding. NE, no expression. (VH CDR3 sequence disclosed as residues 98-106 of SEQ ID NO: 73).

TABLE 9

| VL CDR1 Scanning Matrix | | | | | | | | | | | | | | | | | | | | | | |
|---|---|---|---|---|---|---|---|---|---|---|---|---|---|---|---|---|---|---|---|---|---|---|
| | VL CDR1 | | | | | | | | | | | | | | | | | | | | | |
| sc | 24 G | | 25 G | | 26 N | | 27 N | | 28 I | | 29 G | | 30 S | | 31 K | | 32 N | | 33 V | | 34 Y | |
| A | 1 | 1.3 | 1.1 | 1.3 | 0.8 | 1.3 | 1.2 | 1.2 | 0.9 | 1.9 | 0.6 | 1.1 | 0.8 | 1.1 | 1.2 | 0.6 | 0.7 | 0.2 | 0.7 | 1.5 | 1.7 | 0.3 |
| S | 1 | 1.1 | 0.4 | 1.1 | 1.6 | 1.1 | 0.9 | 1.1 | 0.5 | 1 | 0.9 | 1.2 | — | — | 1.1 | 0.8 | 1 | 1.1 | 1.3 | 1.2 | 0.3 | 1.2 |
| L | 1 | 1.4 | 0.8 | 1.1 | 1 | 1 | 1 | 1.3 | 0.6 | 1.1 | 0.8 | 1.3 | 1.3 | 1.2 | 1.3 | 0.3 | 1.2 | 1.2 | 1 | 0.8 | 0.6 | 0.5 |
| Y | 0.9 | 1 | 1 | 1.4 | 1 | 1.3 | 1 | 1.1 | 0.9 | 1.4 | 0.6 | 0.9 | 0.9 | 1.1 | 1 | 1.3 | 0.9 | 1.2 | 0.7 | 1.3 | — | — |
| D | 1 | 1.2 | 0.9 | 1 | 1 | 1.5 | 1 | 1 | 0.4 | 1.2 | 0.9 | 1.6 | 1.2 | 1.3 | 1.1 | 0.2 | 1.2 | 0.9 | 0.4 | 1.2 | 0.7 | 0.2 |
| Q | 1 | 1.2 | 0.9 | 1.3 | 1 | 1.1 | 0.9 | 1.1 | 0.5 | 1.1 | 1.4 | 1.1 | 0.8 | 1.3 | 0.9 | 0.3 | 1 | 0.9 | 0.5 | 0.8 | 0.6 | 0.2 |
| K | 1 | 1.2 | 0.9 | 1.7 | 1 | 1 | 1 | 1.3 | 0.5 | 1.1 | 0.7 | 1.3 | 1 | 1.6 | — | — | 1.3 | 1 | 0.1 | 1 | 0.6 | 0.3 |
| H | 1 | 1.3 | 1.1 | 1.3 | 1 | 1 | 0.9 | 1.5 | 0.8 | 0.9 | 1 | 1.4 | 1.5 | 1.2 | 1 | 0.5 | 0.9 | 1.5 | 0.5 | NB | 0.8 | 0.2 |
| W | 1.1 | 1.4 | 0.8 | 1.3 | 0.9 | 1.2 | 1.5 | 0.9 | 0.4 | 0.9 | 1.1 | 1.2 | 1.1 | 0.9 | 1.3 | 0.9 | 0.8 | 1.3 | 0.2 | 1.1 | 0.6 | 0.1 |
| P | — | — | — | — | — | — | — | — | — | — | — | — | — | — | — | — | — | — | — | — | — | — |

Summary of difference in 3A5.040 variant antibody titre and kd for variants of VL CDR1 (AbM definition). Kabat amino acid numbering and parent 3A5.040 amino acids are given in the top row. Mutated residue identities are listed in the left column. The leftmost value in each cell is the proportional titre of each variant vs parent 3A5.040 (>1 = higher titre, <1 = lower titre), while the right value is the proportional kd (>1 = lower kd, <1 = higher kd) of each variant vs parent 3A5.040. Variants not made are blank. NB, no binding. NE, no expression. (VL CDR1 sequence disclosed as residues 23-33 of SEQ ID NO: 74).

TABLE 10

| VL CDR2 Scanning Matrix | | | | | | | | | | | | | | |
|---|---|---|---|---|---|---|---|---|---|---|---|---|---|---|
| | VL CDR2 | | | | | | | | | | | | | |
| sc | 50 D | | 51 D | | 52 S | | 53 D | | 54 R | | 55 P | | 56 S | |
| A | 0.8 | 0.6 | 0.9 | 0.8 | 0.8 | 0.9 | 0.5 | 0.1 | 1.4 | 1.2 | 0.1 | 0.9 | 1.4 | 1.1 |
| S | 0.9 | 1 | 0.7 | 0.7 | — | — | 1.5 | 1.9 | 1.3 | 1.1 | 1.1 | 1 | — | — |
| L | 0.9 | 0.4 | 0.8 | 0.6 | 1.1 | 1.8 | 1.4 | 1.3 | 1.4 | 1.2 | 1.5 | 1.2 | 1.3 | 1.1 |
| Y | 0.8 | 0.5 | 0.8 | 0.6 | 1.1 | 1.1 | 2.1 | 1.1 | 1.4 | 1.0 | 1.3 | 1 | 1.2 | 1 |
| D | — | — | — | — | 1.8 | 1.2 | — | — | 1.3 | 1.2 | 1.6 | 1.3 | 1.5 | 1 |
| Q | 0.7 | 0.5 | 0.9 | 0.9 | 0.1 | 1 | 1 | 1 | 1.5 | 1.2 | 1.5 | 1.1 | 1.3 | 1.3 |
| K | 0.7 | 0.6 | 0.7 | 0.9 | 1.7 | 0.1 | 1.8 | 1.1 | 1.7 | 1.0 | 1.4 | 1.1 | 1 | 0.9 |
| H | 1 | 0.6 | 0.9 | 0.6 | 1.7 | 1.1 | 1.2 | 0.9 | 1.4 | 1.4 | 1.8 | 1 | 1.4 | 1 |
| W | 0.7 | 0.4 | 0.6 | 0.5 | 1.7 | 1.1 | 1.8 | 1.2 | 0.1 | 1.0 | 1.6 | 1.4 | 0.9 | 0.9 |
| P | — | — | — | — | — | — | — | — | — | — | — | — | — | — |

Summary of difference in 3A5.040 variant antibody titre and kd for variants of VL CDR2 (AbM definition). Kabat amino acid numbering and parent 3A5.040 amino acids are given in the top row. Mutated residue identities are listed in the left column. The leftmost value in each cell is the proportional titre of each variant vs parent 3A5.040 (>1 = higher titre, <1 = lower titre), while the right value is the proportional kd (>1 = lower kd, <1 = higher kd) of each variant vs parent 3A5.040. Variants not made are blank. NB, no binding. NE, no expression. (VL CDR2 sequence disclosed as residues 49-55 of SEQ ID NO: 74).

TABLE 11

VL CDR3 Scanning Matrix

VL CDR3

| sc | 89 Q | 90 V | 91 W | 92 D | 93 S | 94 S | 95 S | 95A D | 95B H | 96 V | 97 V |
|---|---|---|---|---|---|---|---|---|---|---|---|
| A | 0.6  1 | 0.8  1 | 0.8  0 | 1.1  1.2 | 1.1  0 | 1  1 | 1  1 | 1.1  0 | 0.2  0.7 | 0.7  0.6 | 1.3  1.5 |
| S | 1.3  1 | 0  0.4 | 1  0 | 1.1  1.2 | —  — | —  — | —  — | 1  0.1 | 0.6  1.6 | 0.2  0.5 | 1.1  1.1 |
| L | 0.6  1.2 | 0.6  0.8 | 1  0 | 1.3  1.5 | 1.2  0 | 0.9  0.2 | 1  1 | 0.7  0 | 1.8  0.9 | 0.8  0.6 | 1  1.2 |
| Y | 0.4  1 | 0.9  0.4 | 0.6  0.1 | 0.7  1.1 | 1.2  0 | 1.5  0.3 | 0.8  1.1 | 1  0 | 1.4  1.5 | 0.6  0.1 | 0.9  1.1 |
| D | 0.1  1.2 | 0.3  0.3 | 0.7  0 | —  — | 0.7  0 | 0.1  0.2 | 1.1  0.9 | —  — | 2.1  1.5 | 0.1  0.1 | 1  0.9 |
| Q | —  — | 0.8  0.6 | 0.8  0 | 1.9  0.8 | 1.1  0 | 1.4  0.6 | 0.6  1.3 | 1.1  0 | 1.3  0.8 | 0.3  0.2 | 0.7  1.2 |
| K | 1.4  0.9 | 0.5  1.4 | 0.7  NB | 0.9  1.3 | 1.6  NB | 1.1  0.8 | 1.2  1.2 | 0.7  0 | 0.6  1.2 | 0.2  0 | 0  1 |
| H | 0.5  0.9 | 0.6  0.4 | 0.6  0 | 1.2  1.1 | 1.3  0 | 1  0.8 | 1  1.2 | 1.9  0 | —  — | 0.5  NB | 1.7  1.4 |
| W | 0.7  0.9 | 0.8  0.2 | —  — | NE  NE | 1.2  0 | 0.2  0.4 | 0.9  0.9 | 0.9  0 | 1.5  1 | 0.2  0 | 0.7  1.6 |
| P | 0.7  0.2 | 0.8  0 | 0.4  0 | 0.6  0.8 | 1.1  0 | 1.4  0.9 | 1.5  0 | 1.5  0 | 1.5  0 | 1.1  0.2 | 0.2  1 |

Summary of difference in 3A5.040 variant antibody titre and kd for variants of VL CDR3 (AbM definition). Kabat amino acid numbering and parent 3A5.040 amino acids are given in the top row. Mutated residue identities are listed in the left column. The leftmost value in each cell is the proportional titre of each variant vs parent 3A5.040 (>1 = higher titre, <1 = lower titre), while the right value is the proportional kd (>1 = lower kd, <1 = higher kd) of each variant vs parent 3A5.040. Variants not made are blank. NB, no binding. NE, no expression. (VL CDR3 sequence disclosed as residues 88-98 of SEQ ID NO: 74).

Expression Vector Construction

Nucleotide sequence can influence gene expression and subsequent protein expression level. Several different nucleotide sequences were examined for optimal expression of 3A5.046. These sequences are summarized in the following table:

TABLE 12

Nucleotide sequence

| Gene Name | SEQ ID Nos: |
|---|---|
| 3A5.046 VH | SEQ ID NO: 69 |
| 3A5.046 VL | SEQ ID NO: 71 |
| 3A5.046 HC constant region | SEQ ID NO: 70 |
| 3A5.046 LC constant region | SEQ ID NO: 72 |

Measurement of the Affinity of Antibody 3A5.046 for Human Recombinant IL-5 by SPR The affinity of antibody 3A5.046 for recombinant human IL-5 was determined using a Biacore T200 system (GE Healthcare). Briefly, a commercial mouse anti-human IgG antibody (Thermo Scientific) was coupled to two adjacent (control and test) flowcells on a Biacore CM5 chip (GE Healthcare) according to the manufacturer's recommendations. The 3A5.046 antibody was captured at a low density (approximately 125 RU) on the test flowcell surface and dilutions of recombinant human IL-5 or a buffer blank were injected over both test and control flowcells, at 30 µL/min (FIG. 6, Table 13).

The resulting sensorgrams were double-referenced (test flowcell values subtracted from control (anti-human IgG-coupled surface with no coated antibody) flowcell values and also a buffer blank). Subtracted sensorgrams from injections of human IL-5 at 2.5, 1.25, 0.625, 0.313, and 0.156 µg/mL were fitted to a 1:1 Langmuir binding model using Biacore Evaluation software to determine binding constants from duplicate assays (Table 13).

TABLE 13

Kinetic constants from a multi-concentration Biacore kinetic analysis of 3A5.046 antibody binding to recombinant human IL-5 at 2.5, 1.25, 0.625, 0.313 and 0.156 µg/mL

| Antibody | Experiment | ka (1/Ms) | kd (1/s) | KD (pM) | Chi$^2$ (RU$^2$) |
|---|---|---|---|---|---|
| 3A5.046 | Repeat 1 | 8.16E+05 | 1.58E−05 | 19.4 | 0.0269 |
|  | Repeat 2 | 8.49E+05 | 1.84E−05 | 21.7 | 0.0296 |

These results demonstrate that antibody 3A5.046 has a high affinity for recombinant human IL-5.

Figure 7A:
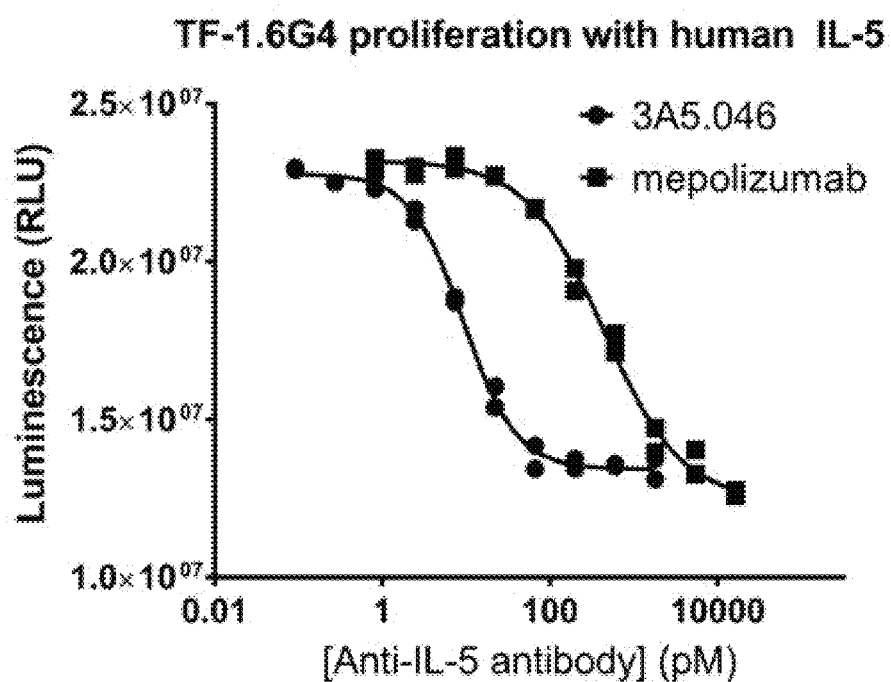
FIG. 7A and FIG. 7B illustrate the proliferation of TF-1.6G4 cells in response to IL-5, and the potency of inhibition of IL-5 driven proliferation by 3A5.046. 3A5.046 was a more potent inhibitor of human IL-5 (FIG. 7A) and cynomolgus monkey IL-5 (FIG. 7B) than mepolizumab.
Figure 7B:
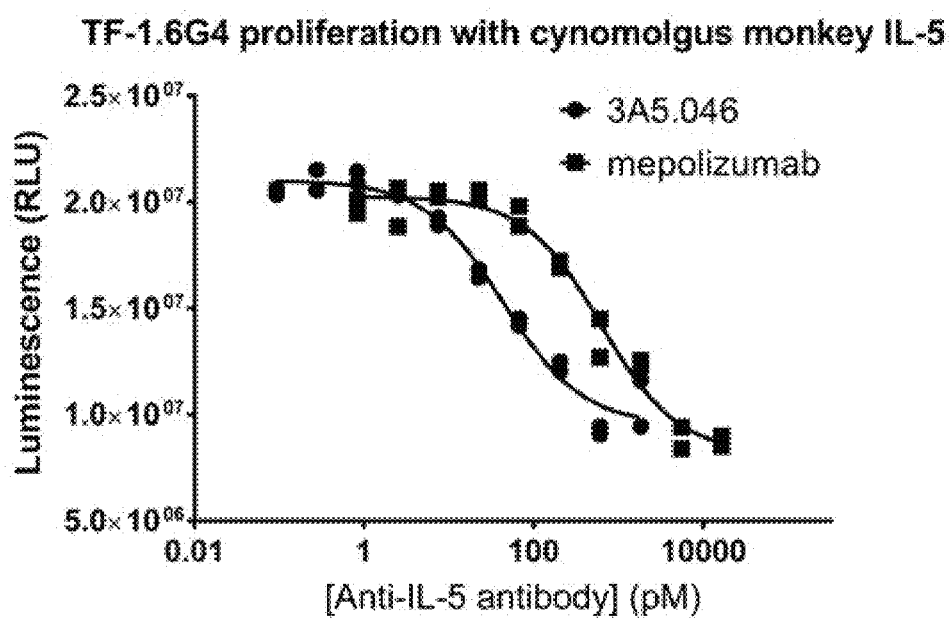
Figure 8A:
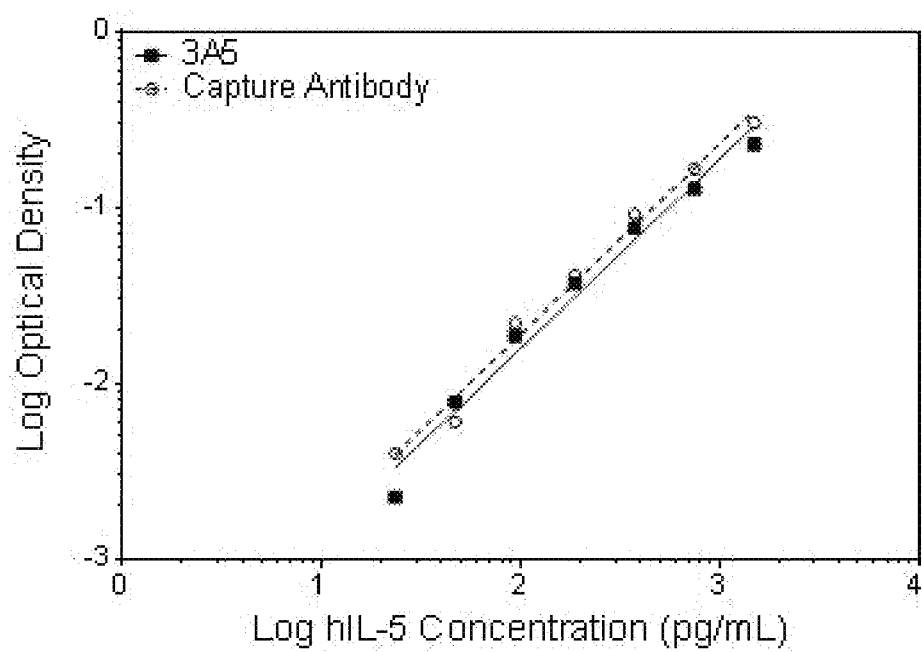
FIG. 8A and FIG. 8B illustrate an exemplary ELISA developed using the 3A5 antibody and a control capture antibody (R&D Systems). The ELISA was able to detect recombinant IL-5 (FIG. 8A) and IL-5 produced from CD3/CD28/IL-33 activated primary human T-cells from 3 donors (FIG. 8B).
Figure 8B:
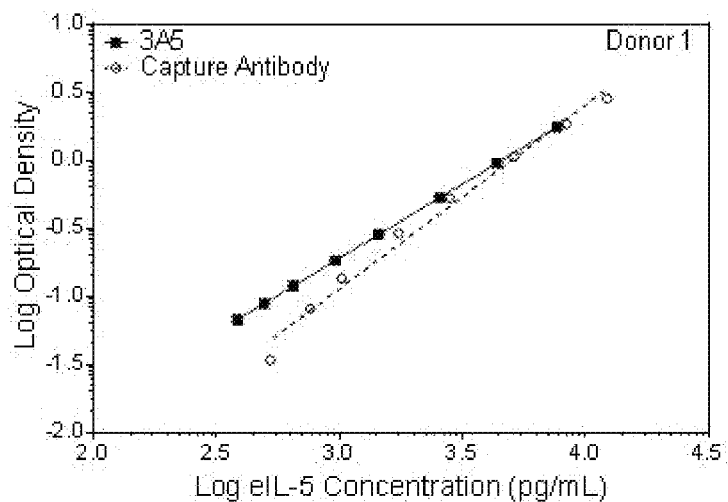
Figure 8B:
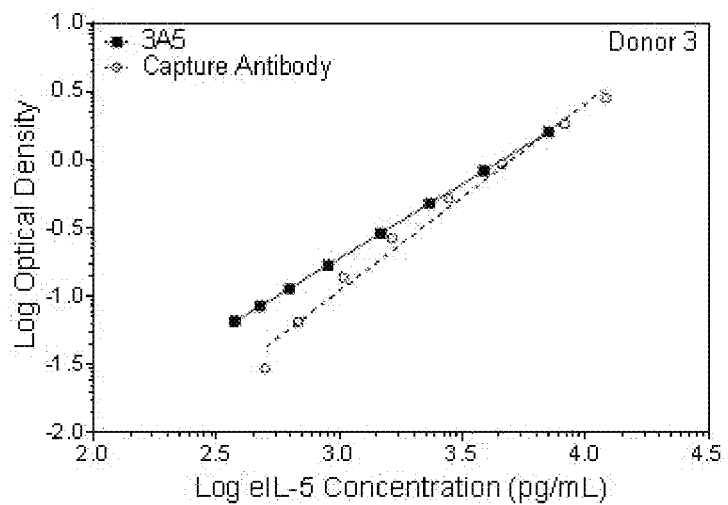
Figure 8B:
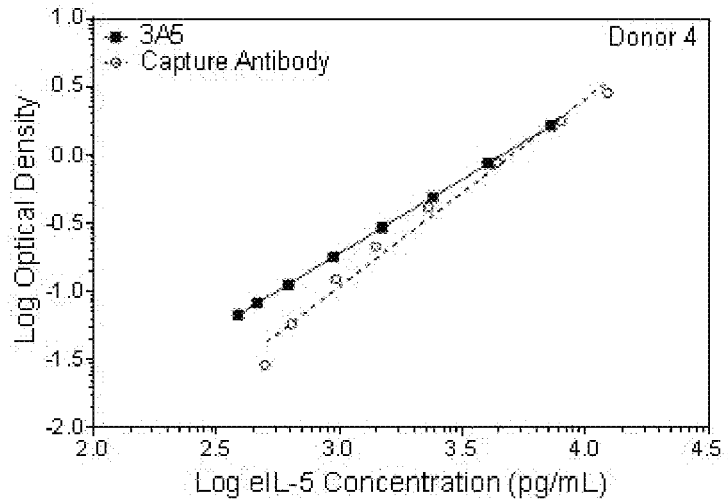

Potency of 3A5.046 Compared to Mepolizumab in the TF-1.6G4 Cell Line Proliferation Assay 3A5.046 and mepolizumab were run in the TF-1.6G4 cell line proliferation assay. 3A5.046 and mepolizumab inhibited human IL-5 proliferation with a mean IC$_{50}$ of 13.8 pM and 534 pM respectively (See Table 14 and FIG. 7A). Both antibodies demonstrated inhibition of cynomolgus monkey IL-5 on the TF1.6G4 cell line (FIG. 7B), with a mean IC$_{50}$ for 3A5.046 of 43.8 pM and for mepolizumab of 584 pM.

TABLE 14

| Antibody | Agonist | Number of Observations | Mean (pM) | Std. Dev. |
|---|---|---|---|---|
| Mepolizumab | Cynomolgus IL-5 | 4 | 584.0982 | 129.9019 |
|  | Human IL-5 | 4 | 534.2803 | 150.2546 |
| 3A5.046 | Cynomolgus IL-5 | 8 | 43.80916 | 12.62095 |
|  | Human IL-5 | 8 | 13.83667 | 4.219783 |

Detection of Native IL5 from Primary Cells Via ELISA Using Anti-IL-5 Antibodies of the Invention Antibody 3A5 was used as a capture reagent in a sandwich ELISA. Paired with a commercially available detection antibody (TRFk5R; R&D systems, #MAB405) quantification of recombinant IL-5 levels in spiked buffer samples could be determined (FIG. 8). This method was then applied to the detection of native IL-5 secreted by primary cells. CD4+ T-cells from four donors were stimulated to secrete IL-5. The IL-5 levels were then determined using the sandwich ELISA with antibody 3A5 as the capture reagent. Three out of four donor T-cells responded to T-cell stimulation and had detectable IL-5 levels in the cell culture supernatant (FIG. 8). Similar studies were performed on human IL-5 secreted from primary human donor CD4+ T-cells using antibody 3A5.046 as a capture agent, and the results obtained were consistent with the results obtained with antibody 3A5 (data not shown).

Anti-IL-5 Antibody Inhibition of Eosinophil Differentiation

Figure 9:
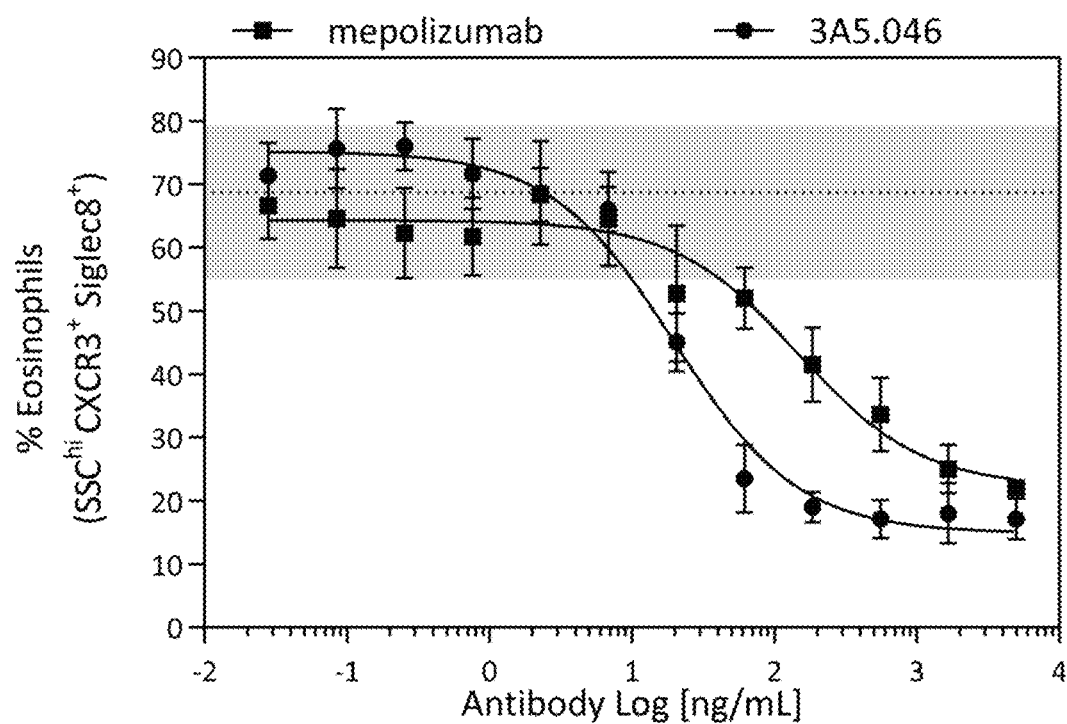
FIG. 9 illustrates the results of an experiment in which CD34+ cord blood cells differentiated into phenotypically mature eosinophils using IL-5 and other cytokines as described in the Examples. Antibody 3A5.046 was more potent than mepolizumab at inhibiting IL-5 induced eosinophil differentiation.
Figure 10A:
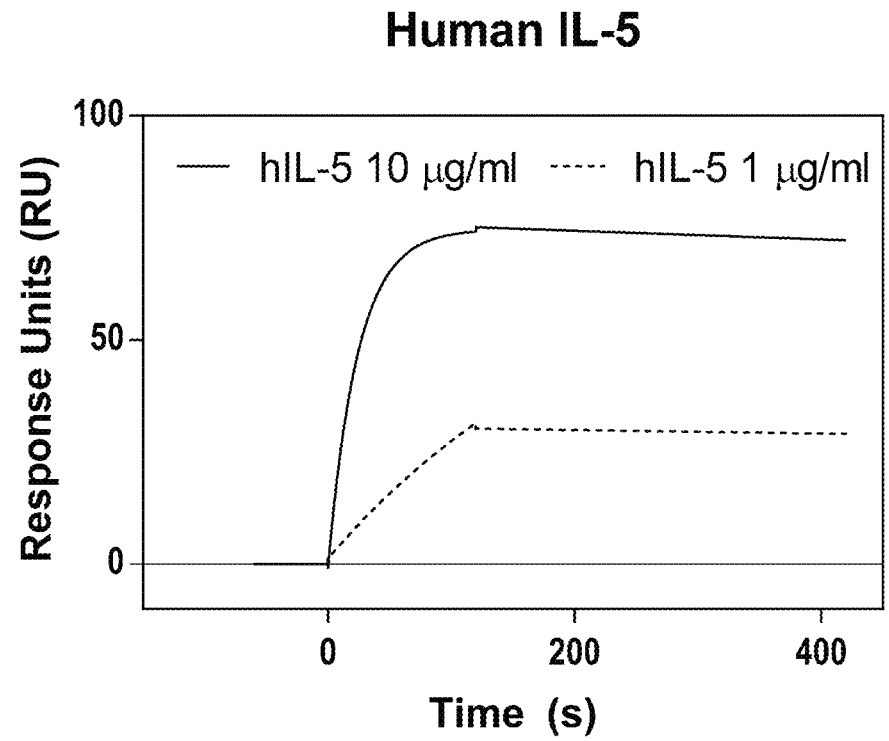
FIG. 10A, FIG. 10B, FIG. 10C, FIG. 10D, and FIG. 10E illustrate the results of the Biacore crossreactivity analysis of antibody 3A5.046 binding to human IL-5 (FIG. 10A), cynomolgus monkey IL-5 (FIG. 10B), mouse IL-5 (FIG. 10C), rat IL-5 (FIG. 10D), and guinea pig IL-5 (FIG. 10E). Double-referenced sensorgrams are shown for binding to cytokines at 1 µg/ml or 10 µg/ml.
Figure 10B:
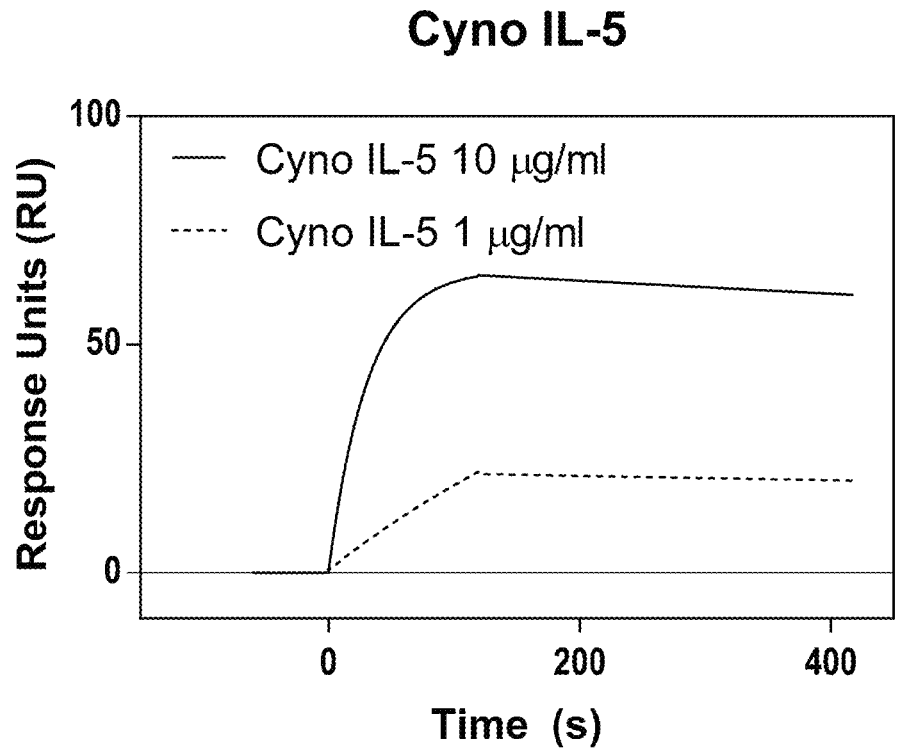
Figure 10C:
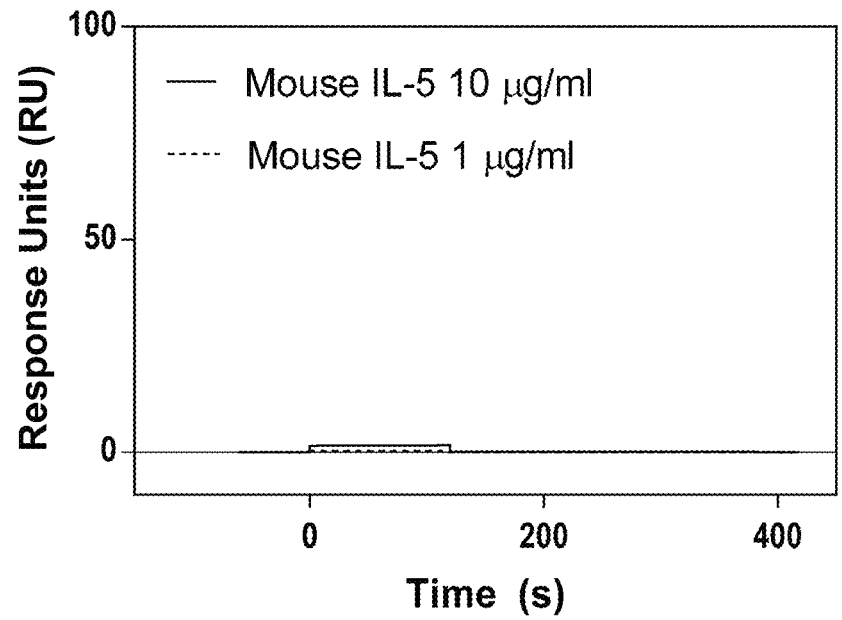
Figure 10D:
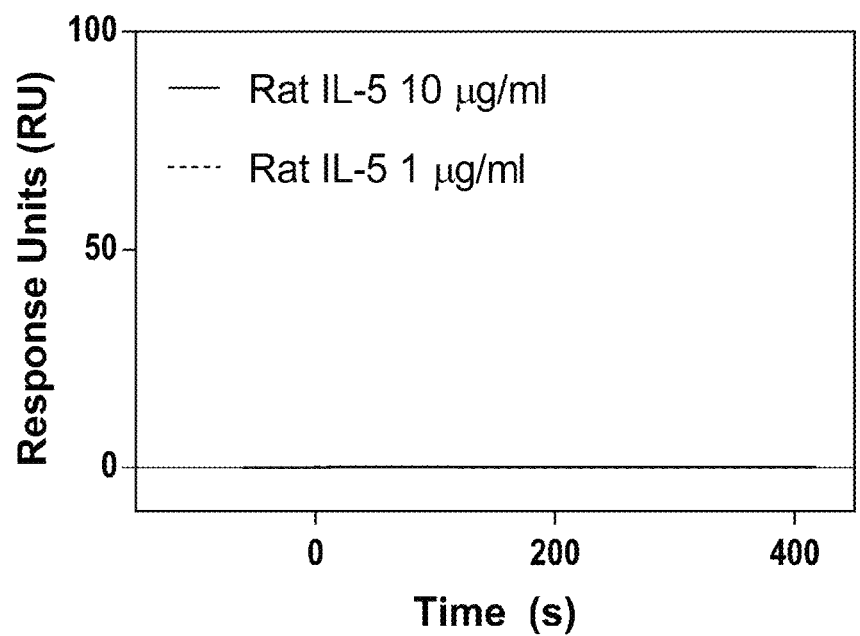
Figure 10E:
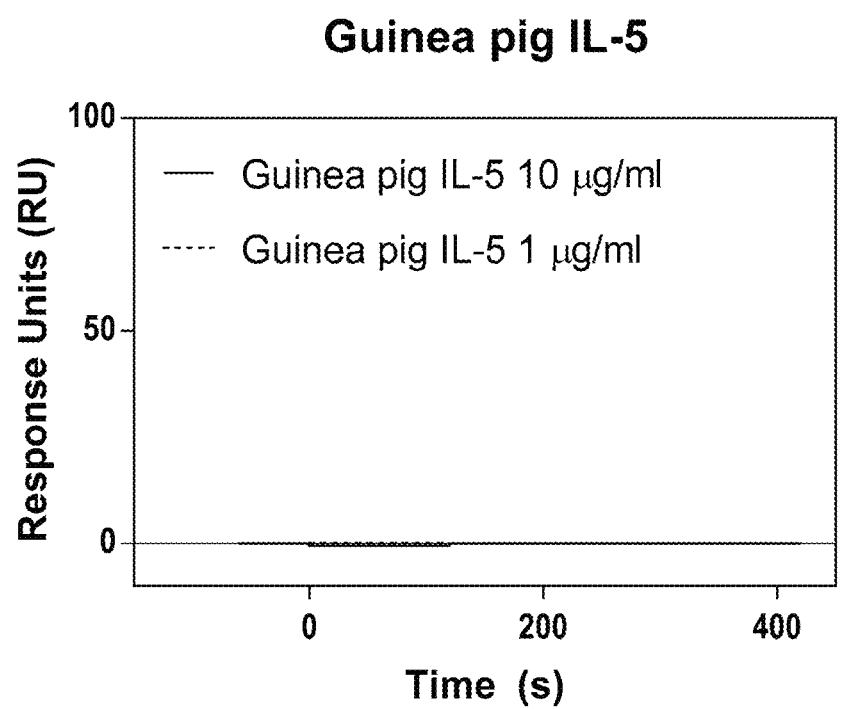
Figure 11A:
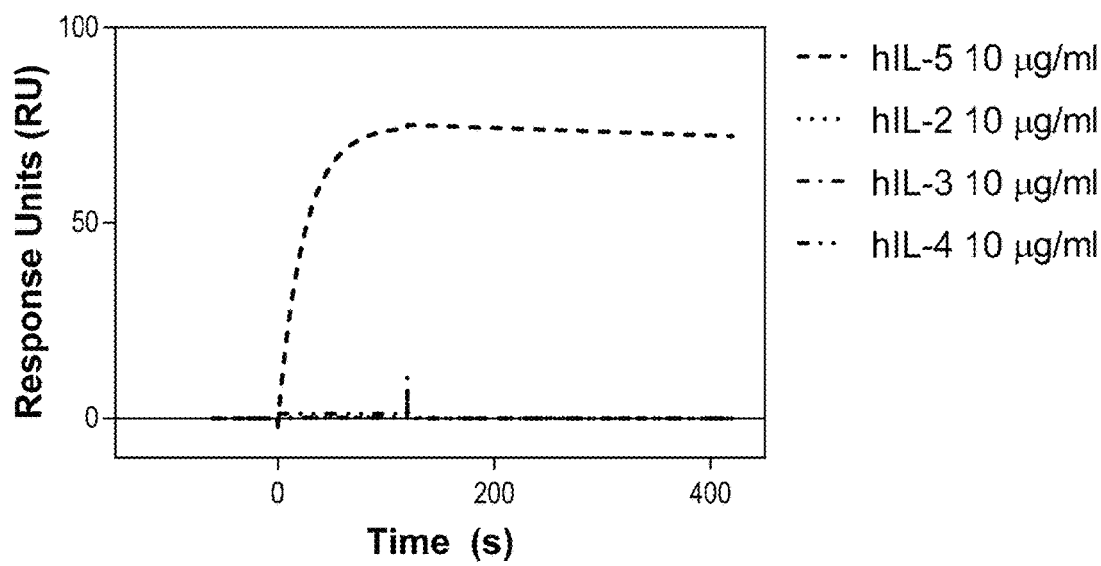
FIG. 11A, FIG. 11B, FIG. 11C, and FIG. 11D illustrate the results of a Biacore specificity analysis of antibody 3A5.046. Double-referenced sensorgrams are shown for binding to cytokines at 10 µg/ml (FIG. 11A and FIG. 11B) or 1 µg/ml (FIG. 11C and FIG. 11D).
Figure 11B:
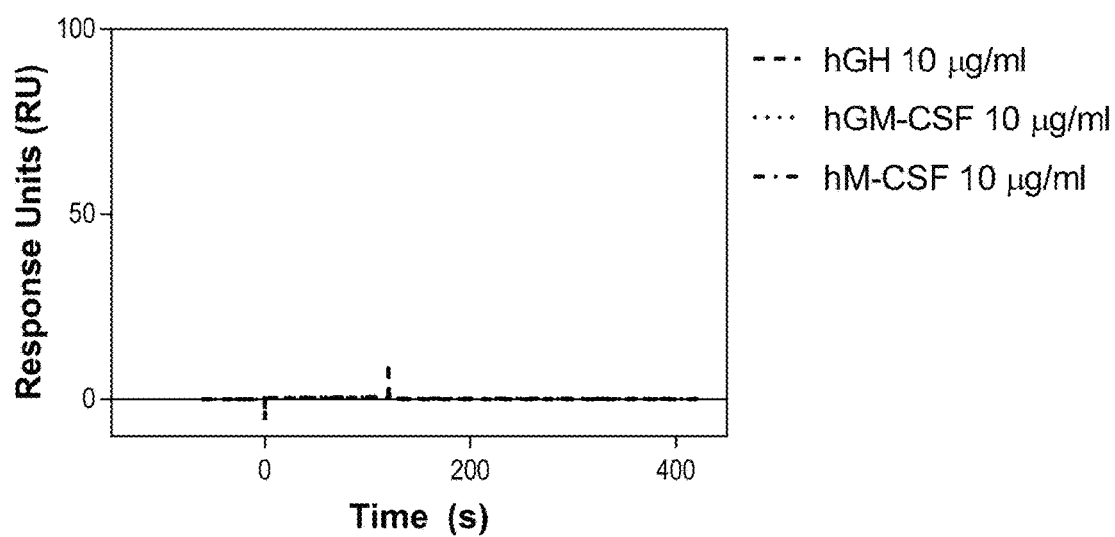
Figure 11C:
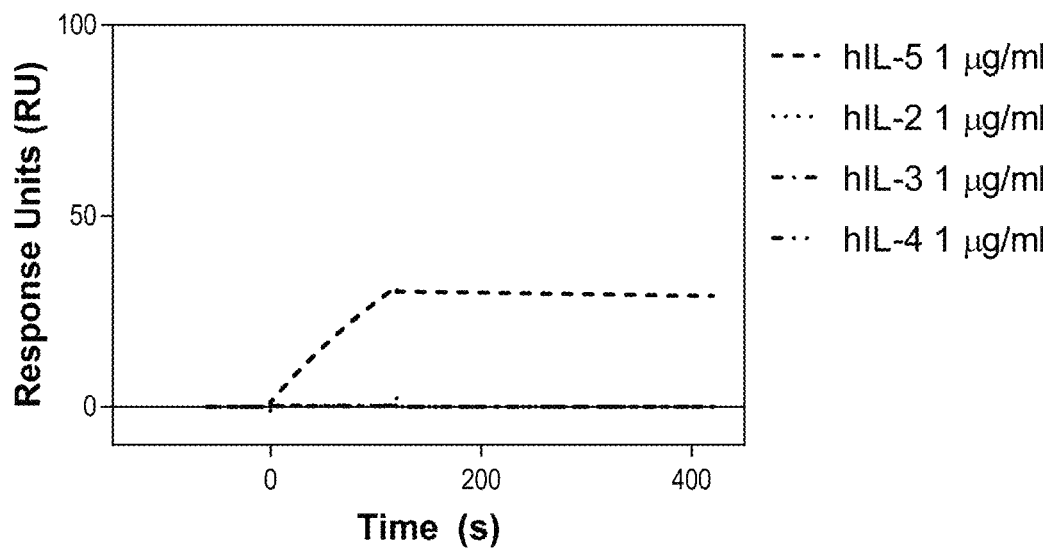
Figure 11D:
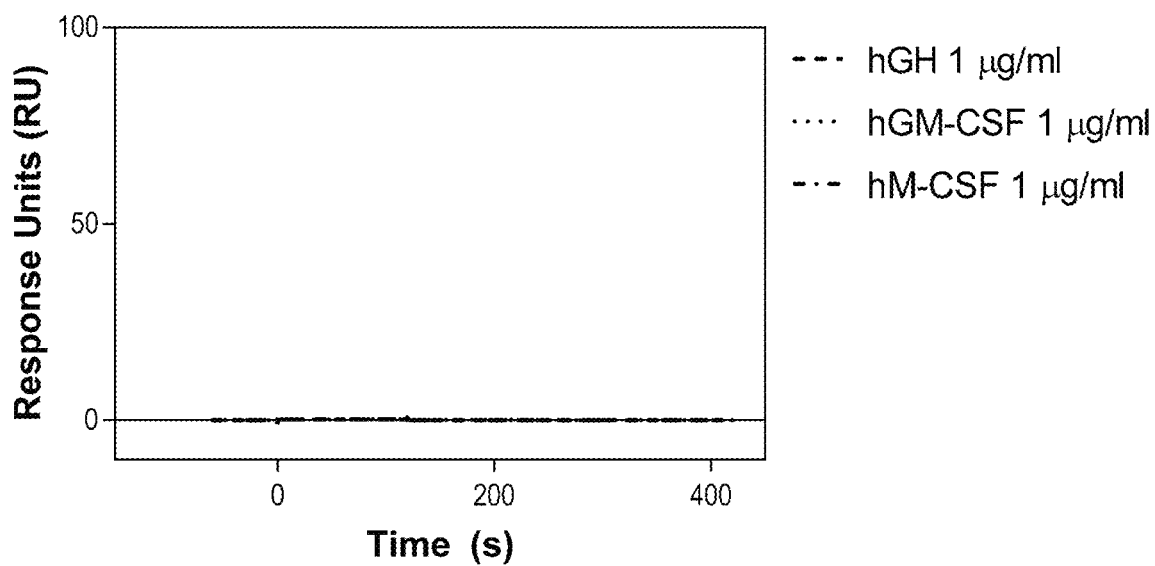

A survival assay using CD34+ cord blood cells was used to assess the capacity of anti-IL-5 antibodies to inhibit the IL-5 dependent differentiation of bone marrow progenitors to eosinophils and to assess the capacity of anti-IL-5 antibodies to inhibit phenotypically mature eosinophil survival. In IL-5 treated control cells, phenotypically mature eosinophils were the predominant population at day 28 (FIG. 9, shaded region in graph). Antibody 3A5.046 was able to inhibit the differentiation of CD34+ cord blood cells, incubated with IL-5 for 28-days, into eosinophils. Antibody 3A5.046 was a more potent inhibitor of IL-5 mediated eosinophil differentiation than mepolizumab (FIG. 9).

X-Ray Crystallography Analysis

The molecular structure of the complex between antibody 3A5.046 Fab and recombinant human IL-5 is investigated by X-ray crystallography. To prepare for X-ray crystallography experiments, 3A5.046 is digested by papain, which cleaves the intact antibody in the hinge region, separating the Fc and Fab domains. The 3A5.046 Fab is purified by standard Protein A affinity chromatography and complexed with recombinant non-glycosylated human IL-5. The 3A5.046 Fab:human IL-5 complex is purified for crystallization experiments using standard size-exclusion chromatography. The complex is set up in variable concentrations, into commercially available sparse-matrix crystallization screens for broad sampling of crystallization conditions. Optimisations of any 'hit' conditions that provide crystals of the complex from the sparse-matrix screens are performed to improve upon crystal morphology and crystal diffraction as required.

Crystals of the 3A5.046 Fab:human IL-5 complex are harvested, flash-frozen in liquid nitrogen and transported to a synchrotron facility for diffraction tests and data collection. Crystal diffraction testing is performed at a synchrotron, which houses high energy X-ray micro beam lines for producing high-resolution diffraction. In this way, X-ray diffraction data on crystals of 3A5.046 Fab:human IL-5 complex is collected. An initial structure model of the complex may be obtained using standard molecular replacement techniques with published molecular structures of IL-5 and Fab as templates. The final structure of the 3A5.046 Fab and human IL-5 complex may be obtained by iterative refinement of the structure model, until the errors of fitting are better than 30% (final $R_{free}$ of 0.3) and chemical bonding parameters (e.g. the distribution of bond lengths and angles, stereochemistry and hydrogen bonds) are within acceptable limits.

Characterisation of Antibody 3A5.046 Binding to IL-5 from Non-Human Model Species Antibody 3A5.046 was tested by Biacore assay using a T200 system (GE Healthcare) for binding to recombinant cytokines human IL-5, rat IL-5, mouse IL-5, and guinea pig IL-5. This panel of non-human IL-5s was chosen to represent major animal model species used in preclinical development. An isotype control antibody (IgG4) and antibody 3A5.046 were immobilized on flowcells 1 and 2 of a Series S CM5 chip (GE Healthcare), respectively, using standard amine coupling methods. Cytokines were diluted to 1 and 10 µg/ml in HBS-EP+ running buffer (GE Healthcare) and injected across flowcells 1 and 2. Buffer-only injections across flowcells 1 and 2 were included for double-referencing. Data analysis was performed using Biacore T200 evaluation software. The resulting sensorgrams were double-referenced (test flowcell values subtracted from control flowcell values and also a buffer blank).

Antibody 3A5.046 was found to bind to human IL-5 and cynomolgus monkey IL-5, but not to mouse IL-5, rat IL-5, or guinea pig IL-5 (FIG. 10A-FIG. 10E). This indicated that 3A5.046 could be used in cynomolgus macaque preclinical models.

Antibody 3A5.046 does not Bind to Other Human Cytokines Closely Related to IL-5

Antibody 3A5.046 was tested by Biacore assay using a T200 system (GE Healthcare) for binding to recombinant human cytokines IL-2, IL-3, IL-4, IL-5, granulocyte macrophage colony stimulating factor (GM-CSF), macrophage colony stimulating factor (M-CSF), and growth hormone (GH). This representative panel of closely-related human cytokines was chosen based on their structural and functional similarity to human IL-5. An isotype control antibody (IgG4) and antibody 3A5.046 were immobilized on flowcells 1 and 2 of a Series S CM5 chip (GE Healthcare), respectively, using standard amine coupling methods. Cytokines were diluted to 1 and 10 µg/ml in HBS-EP+ running buffer (GE Healthcare) and injected across flowcells 1 and 2. Buffer-only injections across flowcells 1 and 2 were included for double-referencing. Data analysis was performed using Biacore T200 evaluation software. The resulting sensorgrams were double-referenced (test flowcell values subtracted from control flowcell values and also a buffer blank).

Antibody 3A5.046 was found to bind only to human IL-5 and not human cytokines IL-2, IL-3, IL-4, GM-CSF, M-CSF, or GH (FIG. 11A-FIG. 11D), thus demonstrating high specificity of 3A5.046 for human IL-5.

Evaluation of Antibody 3A5.046 in an *Ascaris suum*-Induced Cynomolgus Monkey Airways Eosinophilia Model Antibody 3A5.046 was tested using the *Ascaris suum* cynomolgus model of acute airways eosinophilia as described in Hart, T. K., et al., Preclinical efficacy and safety of mepolizumab (SB-240563), a humanized monoclonal antibody to IL-5, in cynomolgus monkeys. J Allergy Clin Immunol, 2001. 108(2): p. 250-7.

Sixteen female cynomolgus macaques that had been previously sensitized to *Ascaris suum* were assessed for level of retained sensitivity by intradermal challenge with *A. suum*. Fourteen of these animals were selected for participation in the study based on the skin wheal response to challenge and randomized into two groups of n=7 per group. Two weeks after intradermal skin wheal testing, baseline blood and bronchoalveolar lavage fluid (BALF) samples were collected (Day 8). About 24 hours after baseline sample collection, animals were treated with either placebo (comprising aqueous buffer pH 6.3 with 200 mM arginine and 25 mM histidine) or antibody 3A5.046 (10 mg/kg intravenously, in aqueous buffer pH 6.3 with 200 mM arginine and 25 mM histidine) in a blinded manner (Day 7). One week after treatment with placebo or antibody a second intradermal *A. suum* challenge was performed and an *A. suum* inhalation challenge was given to all animals by delivery of an equal amount of *A. suum* extract (Greer Laboratories Inc.; 5 mg/ml in sterile water) administered via PARI LC nebulizer (Day 0). Skin wheal diameter was measured 15 minutes after challenge. Two days after *A. suum* inhalation challenge, blood and BALF samples were collected. Additional blood samples for haematology endpoints and PK analysis were collected weekly starting on Day 10 until Day 45.

Figure 12:
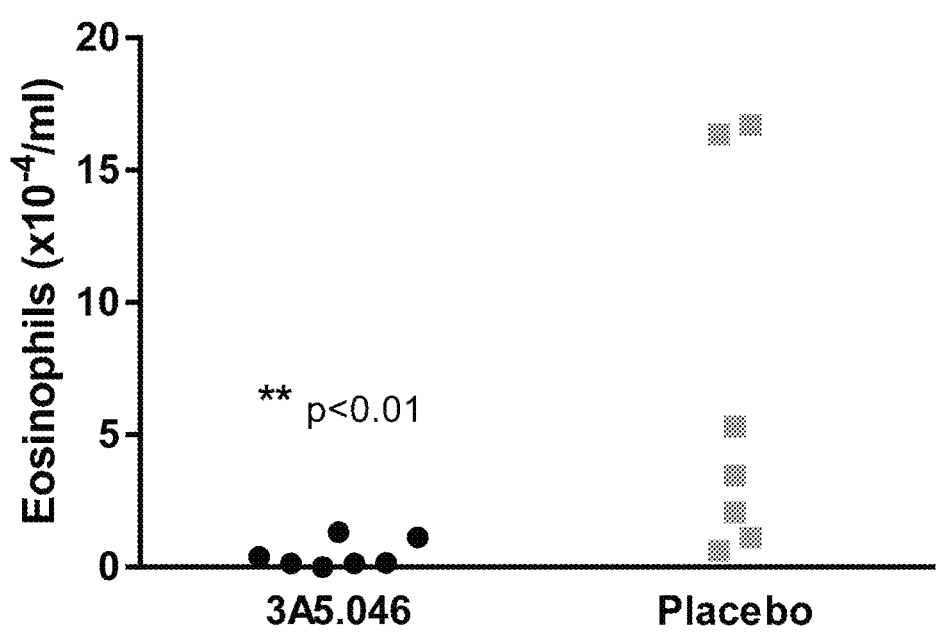
FIG. 12 illustrates the results of *Ascaris suum* (*A. suum*) challenge in a cynomolgus monkey model of airway eosinophilia. At day 2 there was a substantial difference in lung (BALF) eosinophil numbers when comparing 3A5.046-treated and vehicle (placebo)-treated animals (p<0.01; Mann-Whitney test).

There was no significant difference in the skin wheal responses between the first and second intradermal *A. suum* challenges. All animals showed an increase in eosinophils in the BALF as a result of *A. suum* challenge but in animals treated with antibody 3A5.046, this increase was negligible. There were significantly fewer eosinophils in the BALF of animals treated with antibody 3A5.046, compared to placebo-treated animals 48 hours after *A. suum* challenge (p<0.01; Mann-Whitney test; FIG. 12).

Figure 13A:
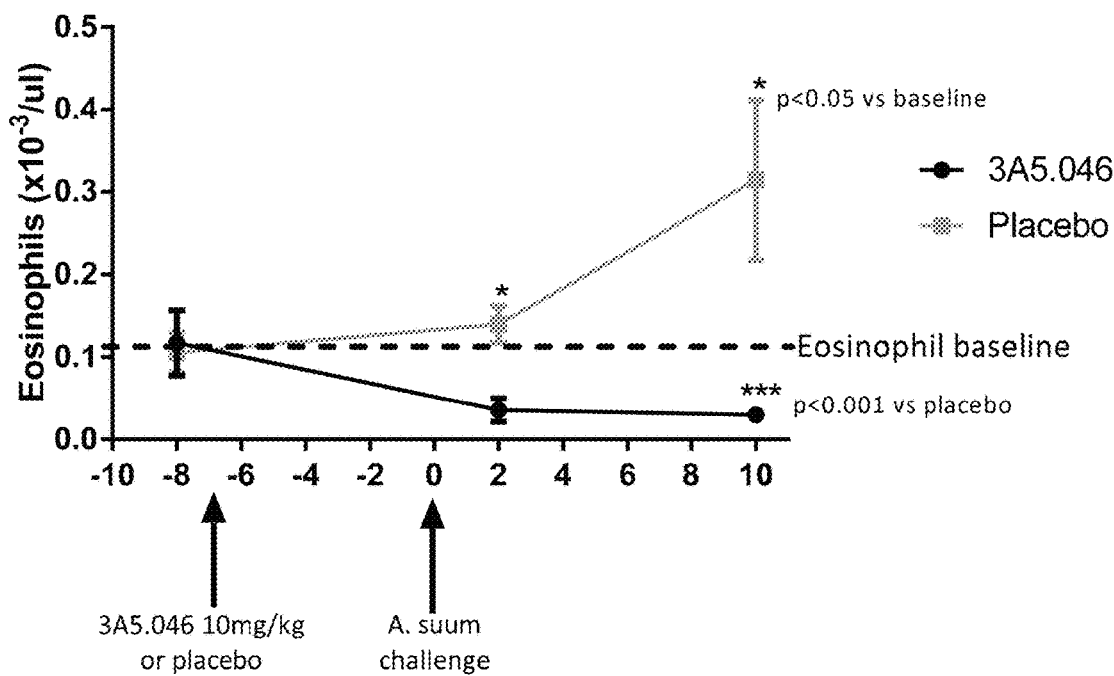
FIG. 13A and FIG. 13B illustrate the blood eosinophil response over 10 days following an *A. suum* challenge in cynomolgus monkeys which were pre-treated with 3A5.046 or a isotype-matched control antibody ("placebo") one week before *A. suum* challenge (FIG. 13A).
Figure 13B:
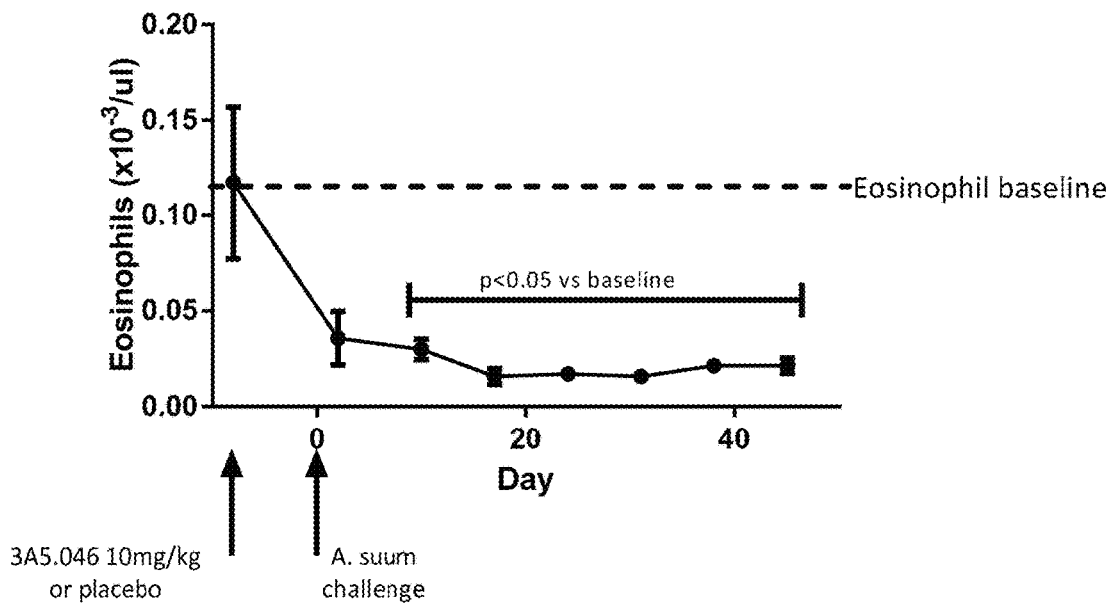

*A. suum* challenge also led to significantly increased blood eosinophils over baseline in placebo-treated animals to day 10 post-challenge (FIG. 13A). Treatment with antibody 3A5.046 led to a significant decrease in blood eosinophils to levels below baseline (FIG. 13A), and this depression in blood eosinophil numbers was maintained over a period of at least 52 days after initial dose (FIG. 13B).

In summary, treatment with 3A5.046 significantly reduced *A. suum*-induced airways eosinophilia 48 hours after challenge, and significantly decreased blood eosinophils, to below baseline levels, for at least 52 days following a single intravenous (IV) 10 mg/kg dose.

Investigation of Antibody Function in a Humanized IL-5 Rat Model of Airways Eosinophilia

Figure 14:
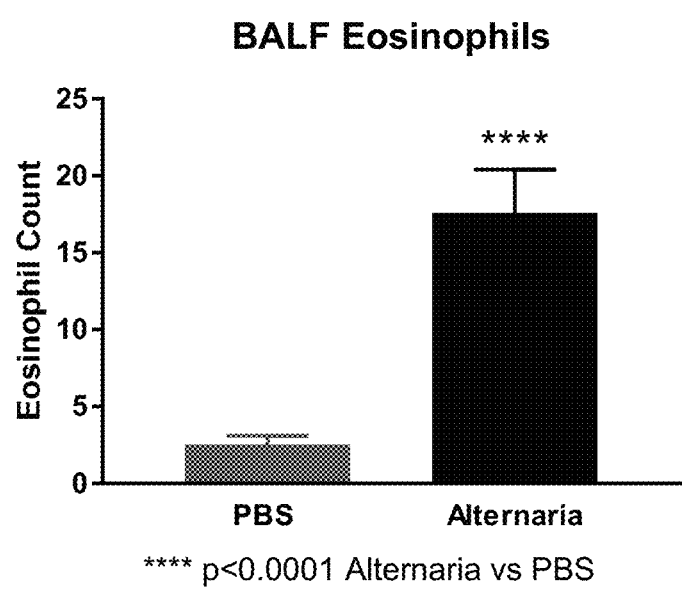
FIG. 14 illustrates BALF eosinophil levels in a human IL-5 knock-in (KI) rat model in response to a challenge with *Alternaria alternata*. This model may be used to test the potency of an anti-IL-5 antibody to modulate the numbers of BALF eosinophils following *Alternaria* challenge.

*Alternaria alternata* (*Alternaria*) is a fungal allergen that is known to trigger asthma in humans and can cause eosinophilia and asthma-like symptoms in rodents. When challenged with *Alternaria*, humanized IL-5 knock-in rats (animals in which the rat IL-5 has been replaced by human IL-5) show elevated eosinophil levels in bronchoalveolar lavage fluid (BALF) from lungs (FIG. 14).

A single intratracheal instillation of *Alternaria* suspension is administered to humanized IL-5 rats, and blood and BALF samples are collected 2, 3 or 4 days after *Alternaria* administration. Typically in this model eosinophils are significantly increased in BALF samples and may be either increased or unchanged in blood samples. Test antibodies are administered prior to induction of eosinophilia with *Alternaria* and assessed for their ability to reduce eosinophil numbers in BALF and blood.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 15

Sequences

| Protein chain | Sequence | Protein Chain | Sequence |
|---|---|---|---|
| Consensus LCDR1 | GX$_1$X$_2$X$_3$X$_4$X$_5$X$_6$KX$_7$X$_8$Y<br>SEQ ID NO: 1 | | |
| Consensus LCDR2 | DDX$_8$X$_9$RPS<br>SEQ ID NO: 2 | | |
| Consensus LCDR3 | QVWX$_{10}$SSSDX$_{11}$VX$_{12}$<br>SEQ ID NO: 3 | | |
| Antibody 3A5 | | | |
| 3A5 HCDR1 | GGSISNGGYYWS<br>SEQ ID NO: 4 | 3A5 LCDR1 | GGNNIGSKNVY<br>SEQ ID NO: 5 |
| 3A5 HCDR2 | YIYYSGSTY<br>SEQ ID NO: 6 | 3A5 LCDR2 | DDSDRPS<br>SEQ ID NO: 7 |
| 3A5 HCDR3 | LGNWFDY<br>SEQ ID NO: 8 | 3A5 LCDR3 | QVWYSSSDHVV<br>SEQ ID NO: 9 |
| 3A5 VH | QVQLQESGPGLVKPSQTLSLTCTVSGGSISNGGYYWSWIRQHPGKGLEWI<br>GYIYYSGSTYYNPSLKSRVSISVDTSKNQFSLKLNSVTAADTAVYYCASL<br>GNWFDYWGQGTLVTVSS<br>SEQ ID NO: 10 | | |
| 3A5 VL | SSILTQPPSVSVAPGQTARITCGGNNIGSKNVYWYQQKPGQAPVLVVHDD<br>SDRPSGIPERFSGSNSGNTATLTISRVEVGDEADYSCQVWYSSSDHVVFGG<br>GTKLTVLG<br>SEQ ID NO: 11 | | |
| 3A5 HC | QVQLQESGPGLVKPSQTLSLTCTVSGGSISNGGYYWSWIRQHPGKGLEWI<br>GYIYYSGSTYYNPSLKSRVSISVDTSKNQFSLKLNSVTAADTAVYYCASL<br>GNWFDYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYIC<br>NVNHKPSNTKVDKKVEPKSCDKTHTCPPCPAPELLGGPSVFLFPPKPKDT<br>LMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPG<br>SEQ ID NO: 12 | | |
| 3A5 LC | SSILTQPPSVSVAPGQTARITCGGNNIGSKNVYWYQQKPGQAPVLVVHDD<br>SDRPSGIPERFSGSNSGNTATLTISRVEVGDEADYSCQVWYSSSDHVVFGG<br>GTKLTVLGQPKAAPSVTLFPPSSEELQANKATLVCLISDFYPGAVTVAWK | | |

TABLE 15-continued

Sequences

| Protein chain | Sequence | Protein Chain | Sequence |
|---|---|---|---|
| | ADSSPVKAGVETTTPSKQSNNKYAASSYLSLTPEQWKSHRSYSCQVTHEG<br>STVEKTVAPTECS<br>SEQ ID NO: 13 | | |
| Antibody 3A5.001 | | | |
| 3A5.001 HCDR1 | GGSISNGGYYWS<br>SEQ ID NO: 4 | 3A5.001 LCDR1 | GGNNIGSKNVY<br>SEQ ID NO: 5 |
| 3A5.001 HCDR2 | YIYYSGSTY<br>SEQ ID NO: 6 | 3A5.001 LCDR2 | DDSDRPS<br>SEQ ID NO: 7 |
| 3A5.001 HCDR3 | LGNWFDY<br>SEQ ID NO: 8 | 3A5.001 LCDR3 | QVWYSSSDHVV<br>SEQ ID NO: 9 |
| 3A5.001 VH | QVQLQESGPGLVKPSQTLSLTCTVSGGSISNGGYYWSWIRQHPGKGLEWI<br>GYIYYSGSTYYNPSLKSRVSISVDTSKNQFSLKLNSVTAADTAVYYCASL<br>GNWFDYWGQGTLVTVSS<br>SEQ ID NO: 10 | | |
| 3A5.001 VL | SSILTQPPSVSVAPGQTARITCGGNNIGSKNVYWYQQKPGQAPVLVVHDD<br>SDRPSGIPERFSGSNSGNTATLTISRVEVGDEADYSCQVWYSSSDHVVFGG<br>GTKLTVLG<br>SEQ ID NO: 11 | | |
| 3A5.001 HC | QVQLQESGPGLVKPSQTLSLTCTVSGGSISNGGYYWSWIRQHPGKGLEWI<br>GYIYYSGSTYYNPSLKSRVSISVDTSKNQFSLKLNSVTAADTAVYYCASL<br>GNWFDYWGQGTLVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 14 | | |
| 3A5.001 LC | SSILTQPPSVSVAPGQTARITCGGNNIGSKNVYWYQQKPGQAPVLVVHDD<br>SDRPSGIPERFSGSNSGNTATLTISRVEVGDEADYSCQVWYSSSDHVVFGG<br>GTKLTVLGQPKAAPSVTLFPPSSEELQANKATLVCLISDFYPGAVTVAWK<br>ADSSPVKAGVETTTPSKQSNNKYAASSYLSLTPEQWKSHRSYSCQVTHEG<br>STVEKTVAPTECS<br>SEQ ID NO: 13 | | |
| Antibody 3A5.040 | | | |
| 3A5.040 HCDR1 | GGSISNGGYYWS<br>SEQ ID NO: 4 | 3A5.040 LCDR1 | GGNNIGSKNVY<br>SEQ ID NO: 5 |
| 3A5.040 HCDR2 | YIYYSGSTY<br>SEQ ID NO: 6 | 3A5.040 LCDR2 | DDSDRPS<br>SEQ ID NO: 7 |
| 3A5.040 HCDR3 | LGNWFDY<br>SEQ ID NO: 8 | 3A5.040 LCDR3 | QVWDSSSDHVV<br>SEQ ID NO: 15 |
| 3A5.040 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.040 VL | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 17 | | |
| 3A5.040 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |

TABLE 15-continued

Sequences

| Protein chain | Sequence | Protein Chain | Sequence |
|---|---|---|---|
| 3A5.040 LC | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 19 | | |

Antibody 3A5.046

| 3A5.046 HCDR1 | GGSISNGGYYWS<br>SEQ ID NO: 4 | 3A5.046 LCDR1 | GGNNIGSKNVY<br>SEQ ID NO: 5 |
| 3A5.046 HCDR2 | YIYYSGSTY<br>SEQ ID NO: 6 | 3A5.046 LCDR2 | DDSDRPS<br>SEQ ID NO: 7 |
| 3A5.046 HCDR3 | LGNWFDY<br>SEQ ID NO: 8 | 3A5.046 LCDR3 | QVWDSSSDHVV<br>SEQ ID NO: 15 |
| 3A5.046 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.046 VL | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 17 | | |
| 3A5.046 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLYITR<br>EPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 20 | | |
| 3A5.046 LC | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 19 | | |

Antibody 3A5.063

| 3A5.063 HCDR1 | GGSISNGGYYWS<br>SEQ ID NO: 4 | 3A5.063 LCDR1 | GKNNIGSKNVY<br>SEQ ID NO: 21 |
| 3A5.063 HCDR2 | YIYYSGSTY<br>SEQ ID NO: 6 | 3A5.063 LCDR2 | DDSDRPS<br>SEQ ID NO: 7 |
| 3A5.063 HCDR3 | LGNWFDY<br>SEQ ID NO: 8 | 3A5.063 LCDR3 | QVWDSSSDHVV<br>SEQ ID NO: 15 |
| 3A5.063 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.063 VL<br>G25K | SYVLTQPPSVSVAPGQTARITCGKNNIGSKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 22 | | |
| 3A5.063 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV | | |

TABLE 15-continued

Sequences

| Protein chain | Sequence | Protein Chain | Sequence |
| --- | --- | --- | --- |
| | SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.063 LC<br>G25K | SYVLTQPPSVSVAPGQTARITCGKNNIGSKNVYWYQQKPGQAPVLVVHD<br>DSDRPSGIPERFSGSNSGNTATLTISRVEVGDEADYSCQVWDSSSDHVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 23 | | |

Antibody 3A5.070

| Protein chain | Sequence | Protein Chain | Sequence |
| --- | --- | --- | --- |
| 3A5.070 HCDR1 | GGSISNGGYYWS<br>SEQ ID NO: 4 | 3A5.070 LCDR1 | GGDNIGSKNVY<br>SEQ ID NO: 24 |
| 3A5.070 HCDR2 | YIYYSGSTY<br>SEQ ID NO: 6 | 3A5.070 LCDR2 | DDSDRPS<br>SEQ ID NO: 7 |
| 3A5.070 HCDR3 | LGNWFDY<br>SEQ ID NO: 8 | 3A5.070 LCDR3 | QVWDSSSDHVV<br>SEQ ID NO: 15 |
| 3A5.070 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.070 VL<br>N26D | SYVLTQPPSVSVAPGQTARITCGGDNIGSKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 25 | | |
| 3A5.070 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.070 LC<br>N26D | SYVLTQPPSVSVAPGQTARITCGGDNIGSKNVYWYQQKPGQAPVLVVHD<br>DSDRPSGIPERFSGSNSGNTATLTISRVEVGDEADYSCQVWDSSSDHVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 26 | | |

Antibody 3A5.082

| Protein chain | Sequence | Protein Chain | Sequence |
| --- | --- | --- | --- |
| 3A5.082 HCDR1 | GGSISNGGYYWS<br>SEQ ID NO: 4 | 3A5.082 LCDR1 | GGNHIGSKNVY<br>SEQ ID NO: 27 |
| 3A5.082 HCDR2 | YIYYSGSTY<br>SEQ ID NO: 6 | 3A5.082 LCDR2 | DDSDRPS<br>SEQ ID NO: 7 |
| 3A5.082 HCDR3 | LGNWFDY<br>SEQ ID NO: 8 | 3A5.082 LCDR3 | QVWDSSSDHVV<br>SEQ ID NO: 15 |
| 3A5.082 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.082 VL<br>N27H | SYVLTQPPSVSVAPGQTARITCGGNHIGSKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 28 | | |
| 3A5.082 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN | | |

TABLE 15-continued

Sequences

| Protein chain | Sequence | Protein Chain | Sequence |
|---|---|---|---|
| | VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.082 LC<br>N27H | SYVLTQPPSVSVAPGQTARITCGGNHIGSKNVYWYQQKPGQAPVLVVHD<br>DSDRPSGIPERFSGSNSGNTATLTISRVEVGDEADYSCQVWDSSSDHVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 29 | | |

Antibody 3A5.084

| 3A5.084 HCDR1 | GGSISNGGYYWS<br>SEQ ID NO: 4 | 3A5.084 LCDR1 | GGNNAGSKNVY<br>SEQ ID NO: 30 |
| 3A5.084 HCDR2 | YIYYSGSTY<br>SEQ ID NO: 6 | 3A5.084 LCDR2 | DDSDRPS<br>SEQ ID NO: 7 |
| 3A5.084 HCDR3 | LGNWFDY<br>SEQ ID NO: 8 | 3A5.084 LCDR3 | QVWDSSSDHVV<br>SEQ ID NO: 15 |
| 3A5.084 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.084 VL<br>I28A | SYVLTQPPSVSVAPGQTARITCGGNNAGSKNVYWYQQKPGQAPVLVVH<br>DDSDRPSGIPERFSGSNSGNTATLTISRVEVGDEADYSCQVWDSSSDHVVF<br>GGGTKLTVLG<br>SEQ ID NO: 31 | | |
| 3A5.084 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.084 LC<br>I28A | SYVLTQPPSVSVAPGQTARITCGGNNAGSKNVYWYQQKPGQAPVLVVH<br>DDSDRPSGIPERFSGSNSGNTATLTISRVEVGDEADYSCQVWDSSSDHVVF<br>GGGTKLTVLGQPKAAPSVTLFPPSSEELQANKATLVCLISDFYPGAVTVA<br>WKADSSPVKAGVETTTPSKQSNNKYAASSYLSLTPEQWKSHRSYSCQVT<br>HEGSTVEKTVAPTECS<br>SEQ ID NO: 32 | | |

Antibody 3A5.107

| 3A5.107 HCDR1 | GGSISNGGYYWS<br>SEQ ID NO: 4 | 3A5.107 LCDR1 | GGNNIGKKNVY<br>SEQ ID NO: 33 |
| 3A5.107 HCDR2 | YIYYSGSTY<br>SEQ ID NO: 6 | 3A5.107 LCDR2 | DDSDRPS<br>SEQ ID NO: 7 |
| 3A5.107 HCDR3 | LGNWFDY<br>SEQ ID NO: 8 | 3A5.107 LCDR3 | QVWDSSSDHVV<br>SEQ ID NO: 15 |
| 3A5.107 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.107 VL<br>S30K | SYVLTQPPSVSVAPGQTARITCGGNNIGKKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 34 | | |
| 3A5.107 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG | | |

TABLE 15-continued

Sequences

| Protein chain | Sequence |
|---|---|
| | NWFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGS FFLYSRLTVDKSRWQEGNVFSCSVMHEALHNHYTQKSLSLSLG SEQ ID NO: 18 |
| 3A5.107 LC S30K | SYVLTQPPSVSVAPGQTARITCGGNNIGKKNVYWYQQKPGQAPVLVVHD DSDRPSGIPERFSGSNSGNTATLTISRVEVGDEADYSCQVWDSSSDHVVFG GGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHE GSTVEKTVAPTECS SEQ ID NO: 35 |

Antibody 3A5.125

| Protein chain | Sequence | Protein Chain | Sequence |
|---|---|---|---|
| 3A5.125 HCDR1 | GGSISNGGYYWS SEQ ID NO: 4 | 3A5.125 LCDR1 | GGNNIGSKHVY SEQ ID NO: 36 |
| 3A5.125 HCDR2 | YIYYSGSTY SEQ ID NO: 6 | 3A5.125 LCDR2 | DDSDRPS SEQ ID NO: 7 |
| 3A5.125 HCDR3 | LGNWFDY SEQ ID NO: 8 | 3A5.125 LCDR3 | QVWDSSSDHVV SEQ ID NO: 15 |

| Protein chain | Sequence |
|---|---|
| 3A5.125 VH | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSS SEQ ID NO: 16 |
| 3A5.125 VL N32H | SYVLTQPPSVSVAPGQTARITCGGNNIGSKHVYWYQQKPGQAPVLVVHD DSDRPSGIPERFSGSNSGNTATLTISRVEVGDEADYSCQVWDSSSDHVVFG GGTKLTVLG SEQ ID NO: 37 |
| 3A5.125 HC | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGS FFLYSRLTVDKSRWQEGNVFSCSVMHEALHNHYTQKSLSLSLG SEQ ID NO: 18 |
| 3A5.125 LC N32H | SYVLTQPPSVSVAPGQTARITCGGNNIGSKHVYWYQQKPGQAPVLVVHD DSDRPSGIPERFSGSNSGNTATLTISRVEVGDEADYSCQVWDSSSDHVVFG GGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHE GSTVEKTVAPTECS SEQ ID NO: 38 |

Antibody 3A5.127

| Protein chain | Sequence | Protein Chain | Sequence |
|---|---|---|---|
| 3A5.127 HCDR1 | GGSISNGGYYWS SEQ ID NO: 4 | 3A5.127 LCDR1 | GGNNIGSKNAY SEQ ID NO: 39 |
| 3A5.127 HCDR2 | YIYYSGSTY SEQ ID NO: 6 | 3A5.127 LCDR2 | DDSDRPS SEQ ID NO: 7 |
| 3A5.127 HCDR3 | LGNWFDY SEQ ID NO: 8 | 3A5.127 LCDR3 | QVWDSSSDHVV SEQ ID NO: 15 |

| Protein chain | Sequence |
|---|---|
| 3A5.127 VH | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSS SEQ ID NO: 16 |
| 3A5.127 VL V33A | SYVLTQPPSVSVAPGQTARITCGGNNIGSKNAYWYQQKPGQAPVLVVHD DSDRPSGIPERFSGSNSGNTATLTISRVEVGDEADYSCQVWDSSSDHVVFG GGTKLTVLG SEQ ID NO: 40 |

TABLE 15-continued

Sequences

| Protein chain | Sequence | Protein Chain | Sequence |
|---|---|---|---|
| 3A5.127 HC | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGS FFLYSRLTVDKSRWQEGNVFSCSVMHEALHNHYTQKSLSLSLG SEQ ID NO: 18 | | |
| 3A5.127 LC V33A | SYVLTQPPSVSVAPGQTARITCGGNNIGSKNAYWYQQKPGQAPVLVVHD DSDRPSGIPERFSGSNSGNTATLTISRVEVGDEADYSCQVWDSSSDHVVFG GGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHE GSTVEKTVAPTECS SEQ ID NO: 41 | | |
| Antibody 3A5.161 | | | |
| 3A5.161 HCDR1 | GGSISNGGYYWS SEQ ID NO: 4 | 3A5.161 LCDR1 | GGNNIGSKNVY SEQ ID NO: 5 |
| 3A5.161 HCDR2 | YIYYSGSTY SEQ ID NO: 6 | 3A5.161 LCDR2 | DDLDRPS SEQ ID NO: 42 |
| 3A5.161 HCDR3 | LGNWFDY SEQ ID NO: 8 | 3A5.161 LCDR3 | QVWDSSSDHVV SEQ ID NO: 15 |
| 3A5.161 VH | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSS SEQ ID NO: 16 | | |
| 3A5.161 VL S52L | SYVLTQPPSVSVAPGQTARITCGGNNIGSKNVYWYQQKPGQAPVLVVHD DLDRPSGIPERFSGSNSGNTATLTISRVEVGDEADYSCQVWDSSSDHVVF GGGTKLTVLG SEQ ID NO: 43 | | |
| 3A5.161 HC | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGS FFLYSRLTVDKSRWQEGNVFSCSVMHEALHNHYTQKSLSLSLG SEQ ID NO: 18 | | |
| 3A5.161 LC S52L | SYVLTQPPSVSVAPGQTARITCGGNNIGSKNVYWYQQKPGQAPVLVVHD DLDRPSGIPERFSGSNSGNTATLTISRVEVGDEADYSCQVWDSSSDHVVF GGGTKLTVLGQPKAAPSVTLFPPSSEELQANKATLVCLISDFYPGAVTVA WKADSSPVKAGVETTTPSKQSNNKYAASSYLSLTPEQWKSHRSYSCQVT HEGSTVEKTVAPTECS SEQ ID NO: 44 | | |
| Antibody 3A5.169 | | | |
| 3A5.169 HCDR1 | GGSISNGGYYWS SEQ ID NO: 4 | 3A5.169 LCDR1 | GGNNIGSKNVY SEQ ID NO: 5 |
| 3A5.169 HCDR2 | YIYYSGSTY SEQ ID NO: 6 | 3A5.169 LCDR2 | DDSSRPS SEQ ID NO: 45 |
| 3A5.169 HCDR3 | LGNWFDY SEQ ID NO: 8 | 3A5.169 LCDR3 | QVWDSSSDHVV SEQ ID NO: 15 |
| 3A5.169 VH | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSS SEQ ID NO: 16 | | |

TABLE 15-continued

Sequences

| Protein chain | Sequence | Protein Chain | Sequence |
|---|---|---|---|
| 3A5.169 VL D53S | SYVLTQPPSVSVAPGQTARITCGGNNIGSKNVYWYQQKPGQAPVLVVHD DSSRPSGIPERFSGSNSGNTATLTISRVEVGDEADYSCQVWDSSSDHVVFG GGTKLTVLG<br>SEQ ID NO: 46 | | |
| 3A5.169 HC | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTPREEQFNSTYRVV SVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGS FFLYSRLTVDKSRWQEGNVFSCSVMHEALHNHYTQKSLSLSLG<br>SEQ ID NO: 18 | | |
| 3A5.169 LC D53S | SYVLTQPPSVSVAPGQTARITCGGNNIGSKNVYWYQQKPGQAPVLVVHD DSSRPSGIPERFSGSNSGNTATLTISRVEVGDEADYSCQVWDSSSDHVVFG GGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHE GSTVEKTVAPTECS<br>SEQ ID NO: 47 | | |

Antibody 3A5.232

| Protein chain | Sequence | Protein Chain | Sequence |
|---|---|---|---|
| 3A5.232 HCDR1 | GGSISNGGYYWS<br>SEQ ID NO: 4 | 3A5.232 LCDR1 | GGNNIGSKNVY<br>SEQ ID NO: 5 |
| 3A5.232 HCDR2 | YIYYSGSTY<br>SEQ ID NO: 6 | 3A5.232 LCDR2 | DDSDRPS<br>SEQ ID NO: 7 |
| 3A5.232 HCDR3 | LGNWFDY<br>SEQ ID NO: 8 | 3A5.232 LCDR3 | QVWLSSSDHVV<br>SEQ ID NO: 48 |
| 3A5.232 VH | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSS<br>SEQ ID NO: 16 | | |
| 3A5.232 VL D92L | SYVLTQPPSVSVAPGQTARITCGGNNIGSKNVYWYQQKPGQAPVLVVHD DSDRPSGIPERFSGSNSGNTATLTISRVEVGDEADYSCQVWLSSSDHVVFG GGTKLTVLG<br>SEQ ID NO: 49 | | |
| 3A5.232 HC | QVQLQESGPGLVKPSQTLSLTCTVSGGSISNGGYYWSWIRQHPGKGLEWI GYIYYSGSTYYNPSLKSRVTISVDTSKNQFSLKLSSVTAADTAVYYCASLG NWFDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTPREEQFNSTYRVV SVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGS FFLYSRLTVDKSRWQEGNVFSCSVMHEALHNHYTQKSLSLSLG<br>SEQ ID NO: 18 | | |
| 3A5.232 LC D92L | SYVLTQPPSVSVAPGQTARITCGGNNIGSKNVYWYQQKPGQAPVLVVHD DSDRPSGIPERFSGSNSGNTATLTISRVEVGDEADYSCQVWLSSSDHVVFG GGTKLTVLGQPKAAPSVTLFPPSSEELQANKATLVCLISDFYPGAVTVAW KADSSPVKAGVETTTPSKQSNNKYAASSYLSLTPEQWKSHRSYSCQVTHE GSTVEKTVAPTECS<br>SEQ ID NO: 50 | | |

Antibody 3A5.276

| Protein chain | Sequence | Protein Chain | Sequence |
|---|---|---|---|
| 3A5.276 HCDR1 | GGSISNGGYYWS<br>SEQ ID NO: 4 | 3A5.276 LCDR1 | GGNNIGSKNVY<br>SEQ ID NO: 5 |
| 3A5.276 HCDR2 | YIYYSGSTY<br>SEQ ID NO: 6 | 3A5.276 LCDR2 | DDSDRPS<br>SEQ ID NO: 7 |
| 3A5.276 HCDR3 | LGNWFDY<br>SEQ ID NO: 8 | 3A5.276 LCDR3 | QVWDSSSDSVV<br>SEQ ID NO: 51 |

TABLE 15-continued

Sequences

| Protein chain | Sequence |
|---|---|
| 3A5.276 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 |
| 3A5.276 VL<br>H95bS | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDSVVFG<br>GGTKLTVLG<br>SEQ ID NO: 52 |
| 3A5.276 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 |
| 3A5.276 LC<br>H95bS | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDSVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 53 |

Antibody 3A5.278

| Protein chain | Sequence | Protein Chain | Sequence |
|---|---|---|---|
| 3A5.278 HCDR1 | GGSISNGGYYWS<br>SEQ ID NO: 4 | 3A5.278 LCDR1 | GGNNIGSKNVY<br>SEQ ID NO: 5 |
| 3A5.278 HCDR2 | YIYYSGSTY<br>SEQ ID NO: 6 | 3A5.278 LCDR2 | DDSDRPS<br>SEQ ID NO: 7 |
| 3A5.278 HCDR3 | LGNWFDY<br>SEQ ID NO: 8 | 3A5.278 LCDR3 | QVWDSSSDYVV<br>SEQ ID NO: 54 |

| Protein chain | Sequence |
|---|---|
| 3A5.278 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 |
| 3A5.278 VL<br>H95bY | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDYVVFG<br>GGTKLTVLG<br>SEQ ID NO: 55 |
| 3A5.278 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 |
| 3A5.278 LC<br>H95bY | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDYVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 56 |

Antibody 3A5.279

| Protein chain | Sequence | Protein Chain | Sequence |
|---|---|---|---|
| 3A5.279 HCDR1 | GGSISNGGYYWS<br>SEQ ID NO: 4 | 3A5.279 LCDR1 | GGNNIGSKNVY<br>SEQ ID NO: 5 |
| 3A5.279 HCDR2 | YIYYSGSTY<br>SEQ ID NO: 6 | 3A5.279 LCDR2 | DDSDRPS<br>SEQ ID NO: 7 |

TABLE 15-continued

Sequences

| Protein chain | Sequence | Protein Chain | Sequence |
|---|---|---|---|
| 3A5.279 HCDR3 | LGNWFDY<br>SEQ ID NO: 8 | 3A5.279 LCDR3 | QVWDSSSDDVV<br>SEQ ID NO: 57 |
| 3A5.279 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.279 VL<br>H95bD | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDDVVFG<br>GGTKLTVLG<br>SEQ ID NO: 58 | | |
| 3A5.279 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.279 LC<br>H95bD | SYVLTQPP SVSVAPGQTARITCGGNNIGSKNVYWYQQKPGQAPVLVVHD<br>DSDRPSGIPERFSGSNSGNTATLTISRVEVGDEADYSCQVWDSSSDDVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 59 | | |
| Antibody 3A5.294 | | | |
| 3A5.294 HCDR1 | GGSISNGGYYWS<br>SEQ ID NO: 4 | 3A5.294 LCDR1 | GGNNIGSKNVY<br>SEQ ID NO: 5 |
| 3A5.294 HCDR2 | YIYYSGSTY<br>SEQ ID NO: 6 | 3A5.294 LCDR2 | DDSDRPS<br>SEQ ID NO: 7 |
| 3A5.294 HCDR3 | LGNWFDY<br>SEQ ID NO: 8 | 3A5.294 LCDR3 | QVWDSSSDHVA<br>SEQ ID NO: 60 |
| 3A5.294 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.294 VL<br>V97A | SYVLTQPP SVSVAPGQTARITCGGNNIGSKNVYWYQQKPGQAPVLVVHD<br>DSDRPSGIPERFSGSNSGNTATLTISRVEVGDEADYSCQVWDSSSDHVAFG<br>GGTKLTVLG<br>SEQ ID NO: 61 | | |
| 3A5.294 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.294 LC<br>V97A | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVAFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 62 | | |
| Antibody 3A5.302 | | | |
| 3A5.302 HCDR1 | GGSISNGGYYWS<br>SEQ ID NO: 4 | 3A5.302 LCDR1 | GGNNIGSKNVY<br>SEQ ID NO: 5 |

TABLE 15-continued

Sequences

| Protein chain | Sequence | Protein Chain | Sequence |
| --- | --- | --- | --- |
| 3A5.302 HCDR2 | YIYYSGSTY<br>SEQ ID NO: 6 | 3A5.302 LCDR2 | DDSDRPS<br>SEQ ID NO: 7 |
| 3A5.302 HCDR3 | LGNWFDY<br>SEQ ID NO: 8 | 3A5.302 LCDR3 | QVWDSSSDHVW<br>SEQ ID NO: 63 |
| 3A5.302 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.302 VL<br>V97W | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVWF<br>GGGTKLTVLG<br>SEQ ID NO: 64 | | |
| 3A5.302 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.302 LC<br>V97W | SYVLTQPPSVSVAPGQTARITCGGNNIGSKNVYWYQQKPGQAPVLVVHD<br>DSDRPSGIPERFSGSNSGNTATLTISRVEVGDEADYSCQVWDSSSDHVWF<br>GGGTKLTVLGQPKAAPSVTLFPPSSEELQANKATLVCLISDFYPGAVTVA<br>WKADSSPVKAGVETTTPSKQSNNKYAASSYLSLTPEQWKSHRSYSCQVT<br>HEGSTVEKTVAPTECS<br>SEQ ID NO: 65 | | |
| 3A5.097 | | | |
| 3A5.097 HCDR1 | GGSISNGGYYWS<br>SEQ ID NO: 4 | 3A5.097 LCDR1 | GGNNIDSKNVY<br>SEQ ID NO: 66 |
| 3A5.097 HCDR2 | YIYYSGSTY<br>SEQ ID NO: 6 | 3A5.097 LCDR2 | DDSDRPS<br>SEQ ID NO: 7 |
| 3A5.097 HCDR3 | LGNWFDY<br>SEQ ID NO: 8 | 3A5.097 LCDR3 | QVWDSSSDHVV<br>SEQ ID NO: 15 |
| 3A5.097 VH | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSS<br>SEQ ID NO: 16 | | |
| 3A5.097 VL<br>G29D | SYVLTQPPSVSVAPGQTARITCGGNNIDSKNVYWYQQKPGQAPVLVVHD<br>DSDRPSGIPERFSGSNSGNTATLTISRVEVGDEADYSCQVWDSSSDHVVFG<br>GGTKLTVLG<br>SEQ ID NO: 67 | | |
| 3A5.097 HC | QVQLQESGPGLVKPSQTLSLTCTVSGGSISNGGYYWSWIRQHPGKGLEWI<br>GYIYYSGSTYYNPSLKSRVTISVDTSKNQFSLKLSSVTAADTAVYYCASLG<br>NWFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLG<br>SEQ ID NO: 18 | | |
| 3A5.097 LC<br>G29D | SYVLTQPPSVSVAPGQTARITCGGNNIDSKNVYWYQQKPGQAPVLVVHD<br>DSDRPSGIPERFSGSNSGNTATLTISRVEVGDEADYSCQVWDSSSDHVVFG<br>GGTKLTVLGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS<br>SEQ ID NO: 68 | | |
| 3A5.046 VH<br>nucleotide | CAGGTGCAGCTGCAGGAATCTGGCCCTGGCCTGGTCAAGCCCAGCCA<br>GACCCTGAGCCTGACCTGTACCGTGTCCGGCGGCAGCATCAGCAACGG | | |

TABLE 15-continued

Sequences

| Protein chain | Sequence |
|---|---|
| sequence (synthetic) | CGGCTACTACTGGTCCTGGATCAGACAGCACCCCGGCAAGGGCCTGG<br>AATGGATCGGCTACATCTACTACAGCGGCAGCACCTACTACAACCCCA<br>GCCTGAAGTCCAGAGTGACCATCAGCGTGGACACCAGCAAGAACCAG<br>TTCAGCCTGAAGCTGAGCAGCGTGACAGCCGCCGACACCGCCGTGTAC<br>TACTGCGCCAGCCTGGGCAATTGGTTCGACTACTGGGGCCAGGGCACC<br>CTCGTGACAGTGTCCTCA<br>SEQ ID NO: 69 |
| 3A5.046 human HC constant region nucleotide sequence (synthetic) | GCTAGCACCAAGGGCCCCAGCGTGTTCCCCCTGGCCCCTTGTAGCAGA<br>AGCACCAGCGAGAGCACAGCCGCCCTGGGCTGCCTGGTGAAAGACTA<br>CTTCCCCGAGCCCGTCACCGTGTCCTGGAACAGCGGAGCCCTGACCAG<br>CGGCGTGCACACCTTTCCAGCCGTGCTGCAGAGCAGCGGCCTGTACAG<br>CCTGAGCAGCGTGGTGACAGTGCCCTCCAGCAGCCTGGGCACCAAGA<br>CCTACACCTGTAACGTGGACCACAAGCCCAGCAACACCAAGGTGGAC<br>AAGCGGGTGGAATCTAAGTACGGCCCACCCTGCCCCCCCTGCCCTGCC<br>CCTGAATTTCTGGGCGGACCCTCCGTGTTCCTGTTCCCCCCAAAGCCCA<br>AGGACACCCTGTATATCACTCGGGAGCCCGAAGTGACCTGCGTGGTGG<br>TGGACGTGTCCCAGGAAGATCCCGAGGTCCAGTTCAATTGGTACGTGG<br>ACGGCGTGGAAGTGCACAACGCCAAGACCAAGCCCAGAGAGGAACA<br>GTTCAACAGCACCTACCGGGTGGTGTCCGTGCTGACCGTGCTGCACCA<br>GGACTGGCTGAACGGCAAAGAGTACAAGTGCAAAGTCTCCAACAAGG<br>GCCTGCCCAGCTCCATCGAGAAAACCATCAGCAAGGCCAAGGGCCAG<br>CCCCGCGAGCCTCAGGTGTACACACTGCCCCCCAGCCAGGAAGAGAT<br>GACCAAGAACCAGGTGTCCCTGACCTGTCTGGTGAAAGGCTTCTACCC<br>CAGCGATATCGCCGTGGAATGGGAGAGCAACGGCCAGCCCGAGAACA<br>ACTACAAGACCACCCCCCCTGTGCTGGACAGCGACGGCAGCTTCTTCC<br>TGTACTCCCGGCTGACCGTGGACAAGAGCCGGTGGCAGGAAGGCAAC<br>GTCTTCAGCTGCAGCGTGATGCACGAGGCCCTGCACAACCACTACACC<br>CAGAAGTCCCTGAGCCTGAGCCTGGGC<br>SEQ ID NO: 70 |
| 3A5.046 VL nucleotide sequence (synthetic) | AGCTACGTGCTGACCCAGCCTCCTAGCGTGTCCGTGGCCCCTGGCCAG<br>ACCGCCAGAATCACCTGTGGCGGCAACAACATCGGCAGCAAGAACGT<br>GTACTGGTATCAGCAGAAGCCCGGCCAGGCCCCCGTGCTGGTGGTGCA<br>CGACGACAGCGACAGACCCAGCGGCATCCCCGAGCGGTTCAGCGGCA<br>GCAACAGCGGCAATACCGCCACCCTGACCATCAGCGGGTGGAAGTG<br>GGCGACGAGGCCGACTACAGCTGCCAGGTCTGGGACAGCAGCAGCGA<br>CCACGTGGTGTTCGGCGGAGGCACCAAGCTGACCGTCCTAGGT<br>SEQ ID NO: 71 |
| 3A5.046 human LC constant region nucleotide sequence (synthetic) | CAGCCCAAGGCCGCTCCCAGCGTGACCCTGTTCCCCCCAAGCAGCGAG<br>GAACTGCAGGCCAACAAGGCCACCCTGGTGTGCCTGATCAGCGACTTC<br>TACCCTGGGGCCGTGACCGTGGCCTGGAAGGCCGATAGCAGCCCTGTG<br>AAGGCCGGCGTGGAAACCACCACCCCCTCCAAGCAGAGCAACAACAA<br>ATACGCCGCCAGCAGCTACCTGTCCCTGACCCCCGAGCAGTGGAAGTC<br>CCACCGGTCCTACAGCTGCCAGGTGACACACGAGGGCAGCACCGTGG<br>AAAAGACCGTGGCCCCCACCGAGTGCAGC<br>SEQ ID NO: 72 |

EMBODIMENTS

The following list of embodiments is intended to complement, rather than displace or supersede, the previous descriptions.

Embodiment 1

A human antibody molecule that immunospecifically binds to human IL-5 with an equilibrium affinity constant ($K_D$) of at least about 40 pM as determined by surface plasmon resonance.

Embodiment 2

A human antibody molecule that immunospecifically binds to human IL-5, the antibody molecule comprising:
a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NOs: 5, 21, 24, 27, 30, 33, 36, 39, or 66, a light chain CDR2 comprising the amino acid sequence of SEQ ID NOs: 7, 42, or 45, and a light chain CDR3 comprising the amino acid sequence of SEQ ID NOs: 15, 48, 51, 54, 57, 60, or 63.

Embodiment 3

The antibody molecule of embodiment 1 or 2, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, and
  a. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 15;
  b. a light chain CDR1 comprising the amino acid sequence of SEQ ID NO: 21, a light chain CDR2 comprising the amino acid sequence of SEQ ID NO: 7, and a light chain CDR3 comprising the amino acid sequence of SEQ ID NO: 15;
c. a light chain CDR1 comprising the amino acid sequence of SEQ ID NO: 24, a light chain CDR2 comprising the amino acid sequence of SEQ ID NO: 7, and a light chain CDR3 comprising the amino acid sequence of SEQ ID NO: 15;
d. a light chain CDR1 comprising the amino acid sequence of SEQ ID NO: 27, a light chain CDR2 comprising the amino acid sequence of SEQ ID NO: 7, and a light chain CDR3 comprising the amino acid sequence of SEQ ID NO: 15;
e. a light chain CDR1 comprising the amino acid sequence of SEQ ID NO: 30, a light chain CDR2 comprising the amino acid sequence of SEQ ID NO: 7, and a light chain CDR3 comprising the amino acid sequence of SEQ ID NO: 15;
f. a light chain CDR1 comprising the amino acid sequence of SEQ ID NO: 33, a light chain CDR2 comprising the amino acid sequence of SEQ ID NO: 7, and a light chain CDR3 comprising the amino acid sequence of SEQ ID NO: 15;
g. a light chain CDR1 comprising the amino acid sequence of SEQ ID NO: 36, a light chain CDR2 comprising the amino acid sequence of SEQ ID NO: 7, and a light chain CDR3 comprising the amino acid sequence of SEQ ID NO: 15;
h. a light chain CDR1 comprising the amino acid sequence of SEQ ID NO: 39, a light chain CDR2 comprising the amino acid sequence of SEQ ID NO: 7, and a light chain CDR3 comprising the amino acid sequence of SEQ ID NO: 15;
i. a light chain CDR1 comprising the amino acid sequence of SEQ ID NO: 66, a light chain CDR2 comprising the amino acid sequence of SEQ ID NO: 7, and a light chain CDR3 comprising the amino acid sequence of SEQ ID NO: 15;
j. a light chain CDR1 comprising the amino acid sequence of SEQ ID NO: 5, a light chain CDR2 comprising the amino acid sequence of SEQ ID NO: 42, and a light chain CDR3 comprising the amino acid sequence of SEQ ID NO: 15;
k. a light chain CDR1 comprising the amino acid sequence of SEQ ID NO: 5, a light chain CDR2 comprising the amino acid sequence of SEQ ID NO: 45, and a light chain CDR3 comprising the amino acid sequence of SEQ ID NO: 15;
l. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 48;
m. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 51;
n. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 54;
o. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 57;
p. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 60; or
q. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 63;
wherein the position of the amino acid residues of the CDR is determined according to AbM.

Embodiment 4

The antibody molecule of embodiment 3, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 15.

Embodiment 5

The antibody molecule of any one of the previous embodiments, wherein the antibody molecule comprises a heavy chain variable region comprising an amino acid sequence that is at least 90%, 95%, 96%, 97%, 98%, 99%, or 100% identical to the amino acid sequence of SEQ ID NO: 16 and
a. a light chain variable region comprising an amino acid sequence that is at least 90%, 95%, 96%, 97%, 98%, 99%, or 100% identical to the amino acid sequence of SEQ ID NO: 17;
b. a light chain variable region comprising an amino acid sequence that is at least 90%, 95%, 96%, 97%, 98%, 99%, or 100% identical to the amino acid sequence of SEQ ID NO: 22;
c. a light chain variable region comprising an amino acid sequence that is at least 90%, 95%, 96%, 97%, 98%, 99%, or 100% identical to the amino acid sequence of SEQ ID NO: 25;
d. a light chain variable region comprising an amino acid sequence that is at least 90%, 95%, 96%, 97%, 98%, 99%, or 100% identical to the amino acid sequence of SEQ ID NO: 28;
e. a light chain variable region comprising an amino acid sequence that is at least 90%, 95%, 96%, 97%, 98%, 99%, or 100% identical to the amino acid sequence of SEQ ID NO: 31;
f. a light chain variable region comprising an amino acid sequence that is at least 90%, 95%, 96%, 97%, 98%, 99%, or 100% identical to the amino acid sequence of SEQ ID NO: 34;
g. a light chain variable region comprising an amino acid sequence that is at least 90%, 95%, 96%, 97%, 98%, 99%, or 100% identical to the amino acid sequence of SEQ ID NO: 37;
h. a light chain variable region comprising an amino acid sequence that is at least 90%, 95%, 96%, 97%, 98%, 99%, or 100% identical to the amino acid sequence of SEQ ID NO: 40;

i. a light chain variable region comprising an amino acid sequence that is at least 90%, 95%, 96%, 97%, 98%, 99%, or 100% identical to the amino acid sequence of SEQ ID NO: 43;
j. a light chain variable region comprising an amino acid sequence that is at least 90%, 95%, 96%, 97%, 98%, 99%, or 100% identical to the amino acid sequence of SEQ ID NO: 46;
k. a light chain variable region comprising an amino acid sequence that is at least 90%, 95%, 96%, 97%, 98%, 99%, or 100% identical to the amino acid sequence of SEQ ID NO: 49;
l. a light chain variable region comprising an amino acid sequence that is at least 90%, 95%, 96%, 97%, 98%, 99%, or 100% identical to the amino acid sequence of SEQ ID NO: 52;
m. a light chain variable region comprising an amino acid sequence that is at least 90%, 95%, 96%, 97%, 98%, 99%, or 100% identical to the amino acid sequence of SEQ ID NO: 55;
n. a light chain variable region comprising an amino acid sequence that is at least 90%, 95%, 96%, 97%, 98%, 99%, or 100% identical to the amino acid sequence of SEQ ID NO: 58;
o. a light chain variable region comprising an amino acid sequence that is at least 90%, 95%, 96%, 97%, 98%, 99%, or 100% identical to the amino acid sequence of SEQ ID NO: 61;
p. a light chain variable region comprising an amino acid sequence that is at least 90%, 95%, 96%, 97%, 98%, 99%, or 100% identical to the amino acid sequence of SEQ ID NO: 64; or
q. a light chain variable region comprising an amino acid sequence that is at least 90%, 95%, 96%, 97%, 98%, 99%, or 100% identical to the amino acid sequence of SEQ ID NO: 67.

Embodiment 6

The antibody molecule of any one of the previous embodiments, wherein the antibody molecule comprises a heavy chain variable region comprising an amino acid sequence that is at least 90%, 95%, 96%, 97%, 98%, 99%, or 100% identical to the amino acid sequence of SEQ ID NO: 16 and a light chain variable region comprising an amino acid sequence that is at least 90%, 95%, 96%, 97%, 98%, 99%, or 100% identical to the amino acid sequence of SEQ ID NO: 17.

Embodiment 7

The antibody molecule of any one of the previous embodiments, wherein the antibody molecule comprises:
a. a S228P mutation;
b. a M252Y mutation, a S254T mutation, and a T256E mutation;
c. a deletion of a heavy chain C-terminal lysine residue; or
d. any combination of a to c.

Embodiment 8

The antibody molecule of embodiment 7, wherein the antibody molecule comprises a S228P mutation and a deletion of a heavy chain C-terminal lysine residue.

Embodiment 9

The antibody molecule of embodiment 7, wherein the antibody molecule comprises a S228P mutation, a M252Y mutation, a S254T mutation, a T256E mutation, and a deletion of a heavy chain C-terminal lysine residue.

Embodiment 10

The antibody molecule of any one of the previous embodiments, wherein the antibody molecule comprises an IgG4 heavy chain constant region and a lambda light chain constant region.

Embodiment 11

The antibody molecule of any one of the previous embodiments, wherein the antibody molecule comprises a heavy chain comprising an amino acid sequence that is at least 90%, 95%, 96%, 97%, 98%, 99%, or 100% identical to the amino acid sequence of SEQ ID NO: 18 and
a. a light chain comprising an amino acid sequence that is at least 90%, 95%, 96%, 97%, 98%, 99%, or 100% identical to the amino acid sequence of SEQ ID NO: 19;
b. a light chain comprising an amino acid sequence that is at least 90%, 95%, 96%, 97%, 98%, 99%, or 100% identical to the amino acid sequence of SEQ ID NO: 23;
c. a light chain comprising an amino acid sequence that is at least 90%, 95%, 96%, 97%, 98%, 99%, or 100% identical to the amino acid sequence of SEQ ID NO: 26;
d. a light chain comprising an amino acid sequence that is at least 90%, 95%, 96%, 97%, 98%, 99%, or 100% identical to the amino acid sequence of SEQ ID NO: 29;
e. a light chain comprising an amino acid sequence that is at least 90%, 95%, 96%, 97%, 98%, 99%, or 100% identical to the amino acid sequence of SEQ ID NO: 32;
f. a light chain comprising an amino acid sequence that is at least 90%, 95%, 96%, 97%, 98%, 99%, or 100% identical to the amino acid sequence of SEQ ID NO: 35;
g. a light chain comprising an amino acid sequence that is at least 90%, 95%, 96%, 97%, 98%, 99%, or 100% identical to the amino acid sequence of SEQ ID NO: 38;
h. a light chain comprising an amino acid sequence that is at least 90%, 95%, 96%, 97%, 98%, 99%, or 100% identical to the amino acid sequence of SEQ ID NO: 41;
i. a light chain comprising an amino acid sequence that is at least 90%, 95%, 96%, 97%, 98%, 99%, or 100% identical to the amino acid sequence of SEQ ID NO: 44;
j. a light chain comprising an amino acid sequence that is at least 90%, 95%, 96%, 97%, 98%, 99%, or 100% identical to the amino acid sequence of SEQ ID NO: 47;
k. a light chain comprising an amino acid sequence that is at least 90%, 95%, 96%, 97%, 98%, 99%, or 100% identical to the amino acid sequence of SEQ ID NO: 50;
l. a light chain comprising an amino acid sequence that is at least 90%, 95%, 96%, 97%, 98%, 99%, or 100% identical to the amino acid sequence of SEQ ID NO: 53;

m. a light chain comprising an amino acid sequence that is at least 90%, 95%, 96%, 97%, 98%, 99%, or 100% identical to the amino acid sequence of SEQ ID NO: 56;
n. a light chain comprising an amino acid sequence that is at least 90%, 95%, 96%, 97%, 98%, 99%, or 100% identical to the amino acid sequence of SEQ ID NO: 59;
o. a light chain comprising an amino acid sequence that is at least 90%, 95%, 96%, 97%, 98%, 99%, or 100% identical to the amino acid sequence of SEQ ID NO: 62;
p. a light chain comprising an amino acid sequence that is at least 90%, 95%, 96%, 97%, 98%, 99%, or 100% identical to the amino acid sequence of SEQ ID NO: 65; or
q. a light chain comprising an amino acid sequence that is at least 90%, 95%, 96%, 97%, 98%, 99%, or 100% identical to the amino acid sequence of SEQ ID NO: 68.

Embodiment 12

The antibody molecule of any one of embodiments 1-10, wherein the antibody molecule comprises a heavy chain comprising an amino acid sequence that is at least 90%, 95%, 96%, 97%, 98%, 99%, or 100% identical to the amino acid sequence of SEQ ID NO: 20 and a light chain comprising an amino acid sequence that is at least 90%, 95%, 96%, 97%, 98%, 99%, or 100% identical to the amino acid sequence of SEQ ID NO: 19.

Embodiment 13

The antibody molecule of embodiment 2 or embodiment 3, wherein the antibody molecule is a Fab fragment, a Fab2 fragment, or a single chain antibody.

Embodiment 14

The antibody molecule of any one of the previous embodiments, wherein the antibody molecule has one or more of the following properties:
a. reduces binding of IL-5 to the IL-5 receptor;
b. has a serum half-life of at least about 20 days; or
c. binds human and cynomolgus monkey IL-5 but not mouse, rat, or guinea pig IL-5.

Embodiment 15

The antibody molecule of embodiment 2, wherein the antibody molecule binds to human IL-5 with an equilibrium affinity constant ($K_D$) of at least about 40 pM as determined by surface plasmon resonance.

Embodiment 16

A pharmaceutical composition comprising the antibody molecule of any one of embodiments 1 to 15.

Embodiment 17

A nucleic acid molecule encoding the antibody molecule of any one of embodiments 1 to 15.

Embodiment 18

A vector comprising the nucleic acid molecule of embodiment 17.

Embodiment 19

A cell transformed to express the antibody molecule of any one of embodiments 1 to 15.

Embodiment 20

A method of treating a subject having eosinophilic asthma, hypereosinophilic syndrome, nasal polyposis with eosinophilic involvement, eosinophilic granulomatosis with polyangiitis, atopic dermatitis, or eosinophilic esophagitis comprising:
administering to the subject a therapeutically effective amount of the antibody molecule of any one of embodiments 1 to 15 or the pharmaceutical composition of embodiment 16 to treat the eosinophilic asthma, hypereosinophilic syndrome, nasal polyposis with eosinophilic involvement, eosinophilic granulomatosis with polyangiitis, atopic dermatitis or eosinophilic esophagitis.

Embodiment 21

Use of an effective amount of the antibody molecule of any one of embodiments 1 to 15 or the pharmaceutical composition of embodiment 16 in the treatment of eosinophilic asthma, hypereosinophilic syndrome, nasal polyposis with eosinophilic involvement, eosinophilic granulomatosis with polyangiitis, atopic dermatitis, or eosinophilic esophagitis.

Embodiment 22

Use of the antibody molecule of any one of embodiments 1 to 15 or the pharmaceutical composition of embodiment 16 in the manufacture of a medicament for the treatment of eosinophilic asthma, hypereosinophilic syndrome, nasal polyposis with eosinophilic involvement, eosinophilic granulomatosis with polyangiitis, atopic dermatitis or eosinophilic esophagitis.

What is claimed:

1. A human antibody molecule that immunospecifically binds to human IL-5 with an equilibrium affinity constant ($K_D$) of at least about 40 pM as determined by surface plasmon resonance, wherein the human antibody molecule comprises:
a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NOs: 5, 21, 24, 27, 30, 33, 36, 39, or 66, a light chain CDR2 comprising the amino acid sequence of SEQ ID NOs: 7, 42, or 45, and a light chain CDR3 comprising the amino acid sequence of SEQ ID NOs: 15, 48, 51, 54, 57, 60, or 63.

2. The antibody molecule of claim 1, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, and
  a. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 15;
  b. a light chain CDR1 comprising the amino acid sequence of SEQ ID NO: 21, a light chain CDR2 comprising the amino acid sequence of SEQ ID NO: 7, and a light chain CDR3 comprising the amino acid sequence of SEQ ID NO: 15;
  c. a light chain CDR1 comprising the amino acid sequence of SEQ ID NO: 24, a light chain CDR2 comprising the amino acid sequence of SEQ ID NO: 7, and a light chain CDR3 comprising the amino acid sequence of SEQ ID NO: 15;
  d. a light chain CDR1 comprising the amino acid sequence of SEQ ID NO: 27, a light chain CDR2 comprising the amino acid sequence of SEQ ID NO: 7, and a light chain CDR3 comprising the amino acid sequence of SEQ ID NO: 15;
  e. a light chain CDR1 comprising the amino acid sequence of SEQ ID NO: 30, a light chain CDR2 comprising the amino acid sequence of SEQ ID NO: 7, and a light chain CDR3 comprising the amino acid sequence of SEQ ID NO: 15;
  f. a light chain CDR1 comprising the amino acid sequence of SEQ ID NO: 33, a light chain CDR2 comprising the amino acid sequence of SEQ ID NO: 7, and a light chain CDR3 comprising the amino acid sequence of SEQ ID NO: 15;
  g. a light chain CDR1 comprising the amino acid sequence of SEQ ID NO: 36, a light chain CDR2 comprising the amino acid sequence of SEQ ID NO: 7, and a light chain CDR3 comprising the amino acid sequence of SEQ ID NO: 15;
  h. a light chain CDR1 comprising the amino acid sequence of SEQ ID NO: 39, a light chain CDR2 comprising the amino acid sequence of SEQ ID NO: 7, and a light chain CDR3 comprising the amino acid sequence of SEQ ID NO: 15;
  i. a light chain CDR1 comprising the amino acid sequence of SEQ ID NO: 66, a light chain CDR2 comprising the amino acid sequence of SEQ ID NO: 7, and a light chain CDR3 comprising the amino acid sequence of SEQ ID NO: 15;
  j. a light chain CDR1 comprising the amino acid sequence of SEQ ID NO: 5, a light chain CDR2 comprising the amino acid sequence of SEQ ID NO: 42, and a light chain CDR3 comprising the amino acid sequence of SEQ ID NO: 15;
  k. a light chain CDR1 comprising the amino acid sequence of SEQ ID NO: 5, a light chain CDR2 comprising the amino acid sequence of SEQ ID NO: 45, and a light chain CDR3 comprising the amino acid sequence of SEQ ID NO: 15;
  l. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 48;
  m. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 51;
  n. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 54;
  o. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 57;
  p. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 60; or
  q. a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 63;
  wherein the position of the amino acid residues of the CDR is determined according to AbM.

3. The antibody molecule of claim 2, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NO: 5, a light chain CDR2 comprising the amino acid sequence of SEQ ID NO: 7, and a light chain CDR3 comprising the amino acid sequence of SEQ ID NO: 15.

4. The antibody molecule of claim 1, wherein the antibody is an IgG molecule comprising:
   a. a S228P mutation in the hinge region;
   b. a M252Y mutation, a S254T mutation, and a T256E mutation in the CH2 domain of the heavy chain;
   c. a deletion of a heavy chain C-terminal lysine residue; or
   d. any combination of a to c.

5. The antibody molecule of claim 4, wherein the antibody molecule comprises a S228P mutation and a deletion of a heavy chain C-terminal lysine residue.

6. The antibody molecule of claim 4, wherein the antibody molecule comprises a S228P mutation, a M252Y mutation, a S254T mutation, a T256E mutation, and a deletion of a heavy chain C-terminal lysine residue.

7. The antibody molecule of claim 1, wherein the antibody molecule comprises an IgG4 heavy chain constant region and a lambda light chain constant region.

8. The antibody molecule of claim 1, wherein the antibody molecule comprises a heavy chain comprising an amino acid sequence that is at least 90%, 95%, 96%, 97%, 98%, 99%, or 100% identical to the amino acid sequence of SEQ ID NO: 18 and
   a. a light chain comprising an amino acid sequence that is at least 90%, 95%, 96%, 97%, 98%, 99%, or 100% identical to the amino acid sequence of SEQ ID NO: 19;
   b. a light chain comprising an amino acid sequence that is at least 90%, 95%, 96%, 97%, 98%, 99%, or 100% identical to the amino acid sequence of SEQ ID NO: 23;
   c. a light chain comprising an amino acid sequence that is at least 90%, 95%, 96%, 97%, 98%, 99%, or 100% identical to the amino acid sequence of SEQ ID NO: 26;
   d. a light chain comprising an amino acid sequence that is at least 90%, 95%, 96%, 97%, 98%, 99%, or 100% identical to the amino acid sequence of SEQ ID NO: 29;
   e. a light chain comprising an amino acid sequence that is at least 90%, 95%, 96%, 97%, 98%, 99%, or 100% identical to the amino acid sequence of SEQ ID NO: 32;
   f. a light chain comprising an amino acid sequence that is at least 90%, 95%, 96%, 97%, 98%, 99%, or 100% identical to the amino acid sequence of SEQ ID NO: 35;
   g. a light chain comprising an amino acid sequence that is at least 90%, 95%, 96%, 97%, 98%, 99%, or 100% identical to the amino acid sequence of SEQ ID NO: 38;
   h. a light chain comprising an amino acid sequence that is at least 90%, 95%, 96%, 97%, 98%, 99%, or 100% identical to the amino acid sequence of SEQ ID NO: 41;
   i. a light chain comprising an amino acid sequence that is at least 90%, 95%, 96%, 97%, 98%, 99%, or 100% identical to the amino acid sequence of SEQ ID NO: 44;
   j. a light chain comprising an amino acid sequence that is at least 90%, 95%, 96%, 97%, 98%, 99%, or 100% identical to the amino acid sequence of SEQ ID NO: 47;
   k. a light chain comprising an amino acid sequence that is at least 90%, 95%, 96%, 97%, 98%, 99%, or 100% identical to the amino acid sequence of SEQ ID NO: 50;
   l. a light chain comprising an amino acid sequence that is at least 90%, 95%, 96%, 97%, 98%, 99%, or 100% identical to the amino acid sequence of SEQ ID NO: 53;
   m. a light chain comprising an amino acid sequence that is at least 90%, 95%, 96%, 97%, 98%, 99%, or 100% identical to the amino acid sequence of SEQ ID NO: 56;
   n. a light chain comprising an amino acid sequence that is at least 90%, 95%, 96%, 97%, 98%, 99%, or 100% identical to the amino acid sequence of SEQ ID NO: 59;
   o. a light chain comprising an amino acid sequence that is at least 90%, 95%, 96%, 97%, 98%, 99%, or 100% identical to the amino acid sequence of SEQ ID NO: 62;
   p. a light chain comprising an amino acid sequence that is at least 90%, 95%, 96%, 97%, 98%, 99%, or 100% identical to the amino acid sequence of SEQ ID NO: 65; or
   q. a light chain comprising an amino acid sequence that is at least 90%, 95%, 96%, 97%, 98%, 99%, or 100% identical to the amino acid sequence of SEQ ID NO: 68.

9. The antibody molecule of claim 1, wherein the antibody molecule comprises a heavy chain comprising an amino acid sequence that is at least 90%, 95%, 96%, 97%, 98%, 99%, or 100% identical to the amino acid sequence of SEQ ID NO: 20 and a light chain comprising an amino acid sequence that is at least 90%, 95%, 96%, 97%, 98%, 99%, or 100% identical to the amino acid sequence of SEQ ID NO: 19.

10. The antibody molecule of claim 1, wherein the antibody molecule is a Fab fragment, a Fab2 fragment, or a single chain antibody.

11. The antibody molecule of claim 1, wherein the antibody molecule has one or more of the following properties:
   a. reduces binding of IL-5 to the IL-5 receptor;
   b. has a serum half-life of at least about 20 days; or
   c. binds human and cynomolgus monkey IL-5 but not mouse, rat, or guinea pig IL-5.

12. A pharmaceutical composition comprising the antibody molecule of claim 1.

13. A nucleic acid molecule encoding the antibody molecule of claim 1.

14. A vector comprising the nucleic acid molecule of claim 13.

15. A cell transformed to express the antibody molecule of claim 1.

16. A method of treating a subject having eosinophilic asthma, hypereosinophilic syndrome, nasal polyposis with eosinophilic involvement, eosinophilic granulomatosis with polyangiitis, atopic dermatitis or eosinophilic esophagitis comprising:
   administering to the subject a therapeutically effective amount of the antibody molecule of claim 1 to treat the eosinophilic asthma, hypereosinophilic syndrome, nasal polyposis with eosinophilic involvement, eosinophilic granulomatosis with polyangiitis, atopic dermatitis or eosinophilic esophagitis.

17. The antibody molecule of claim 1, wherein the antibody molecule comprises a heavy chain variable region comprising the amino acid sequence of SEQ ID NO: 16 and
- a. a light chain variable region comprising the amino acid sequence of SEQ ID NO: 17;
- b. a light chain variable region comprising the amino acid sequence of SEQ ID NO: 22;
- c. a light chain variable region comprising the amino acid sequence of SEQ ID NO: 25;
- d. a light chain variable region comprising the amino acid sequence of SEQ ID NO: 28;
- e. a light chain variable region comprising the amino acid sequence of SEQ ID NO: 31;
- f. a light chain variable region comprising the amino acid sequence of SEQ ID NO: 34;
- g. a light chain variable region comprising the amino acid sequence of SEQ ID NO: 37;
- h. a light chain variable region comprising the amino acid sequence of SEQ ID NO: 40;
- i. a light chain variable region comprising the amino acid sequence of SEQ ID NO: 43;
- j. a light chain variable region comprising the amino acid sequence of SEQ ID NO: 46;
- k. a light chain variable region comprising the amino acid sequence of SEQ ID NO: 49;
- l. a light chain variable region comprising the amino acid sequence of SEQ ID NO: 52;
- m. a light chain variable region comprising the amino acid sequence of SEQ ID NO: 55;
- n. a light chain variable region comprising the amino acid sequence of SEQ ID NO: 58;
- o. a light chain variable region comprising the amino acid sequence of SEQ ID NO: 61;
- p. a light chain variable region comprising the amino acid sequence of SEQ ID NO: 64; or
- q. a light chain variable region comprising the amino acid sequence of SEQ ID NO: 67.

18. The antibody molecule of claim 17, wherein the antibody molecule comprises a heavy chain variable region comprising the amino acid sequence of SEQ ID NO: 16 and a light chain variable region comprising the amino acid sequence of SEQ ID NO: 17.

19. The antibody molecule of claim 17, wherein the antibody molecule comprises a heavy chain variable region comprising the amino acid sequence of SEQ ID NO: 16 and a light chain variable region comprising the amino acid sequence of SEQ ID NO: 22.

20. The antibody molecule of claim 17, wherein the antibody molecule comprises a heavy chain variable region comprising the amino acid sequence of SEQ ID NO: 16 and a light chain variable region comprising the amino acid sequence of SEQ ID NO: 25.

21. The antibody molecule of claim 17, wherein the antibody molecule comprises a heavy chain variable region comprising the amino acid sequence of SEQ ID NO: 16 and a light chain variable region comprising the amino acid sequence of SEQ ID NO: 28.

22. The antibody molecule of claim 1, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NO: 21, a light chain CDR2 comprising the amino acid sequence of SEQ ID NO: 7, and a light chain CDR3 comprising the amino acid sequence of SEQ ID NO: 15.

23. The antibody molecule of claim 1, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NO: 24, a light chain CDR2 comprising the amino acid sequence of SEQ ID NO: 7, and a light chain CDR3 comprising the amino acid sequence of SEQ ID NO: 15.

24. The antibody molecule of claim 1, wherein the antibody molecule comprises a heavy chain CDR1 comprising the amino acid sequence of SEQ ID NO: 4, a heavy chain CDR2 comprising the amino acid sequence of SEQ ID NO: 6, a heavy chain CDR3 comprising the amino acid sequence of SEQ ID NO: 8, a light chain CDR1 comprising the amino acid sequence of SEQ ID NO: 27, a light chain CDR2 comprising the amino acid sequence of SEQ ID NO: 7, and a light chain CDR3 comprising the amino acid sequence of SEQ ID NO: 15.

* * * * *

SEQUENCE LISTING

```
<160> NUMBER OF SEQ ID NOS: 75

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Gly or Lys
<220> FEATURE:
<221> NAME/KEY: MOD_RES
<222> LOCATION: (3)..(3)
<223> OTHER INFORMATION: Asn or Asp
<220> FEATURE:
<221> NAME/KEY: MOD_RES
<222> LOCATION: (4)..(4)
<223> OTHER INFORMATION: Asn or His
<220> FEATURE:
<221> NAME/KEY: MOD_RES
<222> LOCATION: (5)..(5)
<223> OTHER INFORMATION: Ile or Ala
<220> FEATURE:
<221> NAME/KEY: MOD_RES
<222> LOCATION: (6)..(6)
<223> OTHER INFORMATION: Gly or Asp
<220> FEATURE:
<221> NAME/KEY: MOD_RES
<222> LOCATION: (7)..(7)
<223> OTHER INFORMATION: Ser or Lys
<220> FEATURE:
<221> NAME/KEY: MOD_RES
<222> LOCATION: (9)..(9)
<223> OTHER INFORMATION: Asn or His
<220> FEATURE:
<221> NAME/KEY: MOD_RES
<222> LOCATION: (10)..(10)
<223> OTHER INFORMATION: Val or Ala

<400> SEQUENCE: 1

Gly Xaa Xaa Xaa Xaa Xaa Xaa Lys Xaa Xaa Tyr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Leu
<220> FEATURE:
<221> NAME/KEY: MOD_RES
<222> LOCATION: (4)..(4)
<223> OTHER INFORMATION: Asp or Ser

<400> SEQUENCE: 2

Asp Asp Xaa Xaa Arg Pro Ser
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp or Leu
<220> FEATURE:
<221> NAME/KEY: MOD_RES
<222> LOCATION: (9)..(9)
<223> OTHER INFORMATION: His, Ser, Tyr or Asp
<220> FEATURE:
<221> NAME/KEY: MOD_RES
<222> LOCATION: (11)..(11)
<223> OTHER INFORMATION: Val, Ala or Trp
```

<400> SEQUENCE: 3

Gln Val Trp Xaa Ser Ser Ser Asp Xaa Val Xaa
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Ile Ser Asn Gly Gly Tyr Tyr Trp Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Asn Asn Ile Gly Ser Lys Asn Val Tyr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Tyr Tyr Ser Gly Ser Thr Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Ser Asp Arg Pro Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gly Asn Trp Phe Asp Tyr
1               5

<210> SEQ ID NO 9
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Val Trp Tyr Ser Ser Asp His Val Val
1               5                   10

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Ser Leu Gly Asn Trp Phe Asp Tyr Trp Gly Gln Gly Thr Leu
            100                 105                 110

Val Thr Val Ser Ser
        115

<210> SEQ ID NO 11
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Ser Ile Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Tyr Ser Ser Ser Asp His
                85                  90                  95

Val Val Phe Gly Gly Gly Thr Lys Leu Thr Val Leu Gly
            100                 105
```

```
<210> SEQ ID NO 12
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Ser Leu Gly Asn Trp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Ser Ile Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
                20                  25                  30

Tyr Trp Tyr Gln Gln Lys Pro Gly Gln Ala Pro Val Leu Val Val His
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Tyr Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 14
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

-continued

```
Gln Val Gln Leu Gln Glu Ser Gly Pro Gly Leu Val Lys Pro Ser Gln
  1               5                  10                  15
Thr Leu Ser Leu Thr Cys Thr Val Ser Gly Gly Ser Ile Ser Asn Gly
             20                  25                  30
Gly Tyr Tyr Trp Ser Trp Ile Arg Gln His Pro Gly Lys Gly Leu Glu
         35                  40                  45
Trp Ile Gly Tyr Ile Tyr Tyr Ser Gly Ser Thr Tyr Tyr Asn Pro Ser
 50                  55                  60
Leu Lys Ser Arg Val Ser Ile Ser Val Asp Thr Ser Lys Asn Gln Phe
 65                  70                  75                  80
Ser Leu Lys Leu Asn Ser Val Thr Ala Ala Asp Thr Ala Val Tyr Tyr
             85                  90                  95
Cys Ala Ser Leu Gly Asn Trp Phe Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
```

```
                420              425              430
Tyr Thr Gln Lys Ser Leu Ser Leu Ser Leu Gly
        435              440

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Val Trp Asp Ser Ser Ser Asp His Val Val
1               5                   10

<210> SEQ ID NO 16
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Leu Gly Asn Trp Phe Asp Tyr Trp Gly Gln Gly Thr Leu
            100                 105                 110

Val Thr Val Ser Ser
        115

<210> SEQ ID NO 17
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80
```

```
Asp Glu Ala Asp Tyr Ser Cys Gln Val Trp Asp Ser Ser Asp His
                85                  90                  95

Val Val Phe Gly Gly Thr Lys Leu Thr Val Leu Gly
            100                 105

<210> SEQ ID NO 18
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Leu Gly Asn Trp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
```

```
                    325                 330                 335
Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
                435                 440
```

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 20
<211> LENGTH: 443

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Ser Leu Gly Asn Trp Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Tyr Ile Thr Arg Glu Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

```
Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Lys Asn Asn Ile Gly Ser Lys Asn Val Tyr
1               5                   10

<210> SEQ ID NO 22
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Tyr Val Leu Thr Gln Pro Pro Ser Val Ser Val Ala Pro Gly Gln
1               5                   10                  15

Thr Ala Arg Ile Thr Cys Gly Lys Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Tyr Val Leu Thr Gln Pro Pro Ser Val Ser Val Ala Pro Gly Gln
1               5                   10                  15

Thr Ala Arg Ile Thr Cys Gly Lys Asn Asn Ile Gly Ser Lys Asn Val
            20                  25                  30

Tyr Trp Tyr Gln Gln Lys Pro Gly Gln Ala Pro Val Leu Val Val His
        35                  40                  45
```

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Val Gly
 65                  70                  75                  80

Asp Glu Ala Asp Tyr Ser Cys Gln Val Trp Asp Ser Ser Asp His
                 85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
210

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Asp Asn Ile Gly Ser Lys Asn Val Tyr
1               5                   10

<210> SEQ ID NO 25
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Tyr Val Leu Thr Gln Pro Pro Ser Val Ser Val Ala Pro Gly Gln
1               5                   10                  15

Thr Ala Arg Ile Thr Cys Gly Gly Asp Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Tyr Val Leu Thr Gln Pro Pro Ser Val Ser Val Ala Pro Gly Gln
1               5                   10                  15

Thr Ala Arg Ile Thr Cys Gly Gly Asp Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Asp His
                85                  90                  95

Val Val Phe Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Asn His Ile Gly Ser Lys Asn Val Tyr
1               5                   10

<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Tyr Val Leu Thr Gln Pro Pro Ser Val Ser Val Ala Pro Gly Gln

```
                1               5                   10                  15
            Thr Ala Arg Ile Thr Cys Gly Gly Asn His Ile Gly Ser Lys Asn Val
                            20                  25                  30

Tyr Trp Tyr Gln Gln Lys Pro Gly Gln Ala Pro Val Leu Val Val His
                            35                  40                  45

Asp Asp Ser Asp Arg Pro Ser Gly Ile Pro Glu Arg Phe Ser Gly Ser
                50                  55                  60

Asn Ser Gly Asn Thr Ala Thr Leu Thr Ile Ser Arg Val Glu Val Gly
            65                  70                  75                  80

Asp Glu Ala Asp Tyr Ser Cys Gln Val Trp Asp Ser Ser Ser Asp His
                            85                  90                  95

Val Val Phe Gly Gly Gly Thr Lys Leu Thr Val Leu Gly
                            100                 105

<210> SEQ ID NO 29
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Tyr Val Leu Thr Gln Pro Pro Ser Val Ser Val Ala Pro Gly Gln
            1               5                   10                  15

Thr Ala Arg Ile Thr Cys Gly Gly Asn His Ile Gly Ser Lys Asn Val
                            20                  25                  30

Tyr Trp Tyr Gln Gln Lys Pro Gly Gln Ala Pro Val Leu Val Val His
                            35                  40                  45

Asp Asp Ser Asp Arg Pro Ser Gly Ile Pro Glu Arg Phe Ser Gly Ser
                50                  55                  60

Asn Ser Gly Asn Thr Ala Thr Leu Thr Ile Ser Arg Val Glu Val Gly
            65                  70                  75                  80

Asp Glu Ala Asp Tyr Ser Cys Gln Val Trp Asp Ser Ser Ser Asp His
                            85                  90                  95

Val Val Phe Gly Gly Gly Thr Lys Leu Thr Val Leu Gly Gln Pro Lys
                            100                 105                 110

Ala Ala Pro Ser Val Thr Leu Phe Pro Pro Ser Ser Glu Glu Leu Gln
                            115                 120                 125

Ala Asn Lys Ala Thr Leu Val Cys Leu Ile Ser Asp Phe Tyr Pro Gly
                        130                 135                 140

Ala Val Thr Val Ala Trp Lys Ala Asp Ser Ser Pro Val Lys Ala Gly
            145                 150                 155                 160

Val Glu Thr Thr Thr Pro Ser Lys Gln Ser Asn Asn Lys Tyr Ala Ala
                            165                 170                 175

Ser Ser Tyr Leu Ser Leu Thr Pro Glu Gln Trp Lys Ser His Arg Ser
                        180                 185                 190

Tyr Ser Cys Gln Val Thr His Glu Gly Ser Thr Val Glu Lys Thr Val
                            195                 200                 205

Ala Pro Thr Glu Cys Ser
                        210

<210> SEQ ID NO 30
<211> LENGTH: 11
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 30

Gly Gly Asn Asn Ala Gly Ser Lys Asn Val Tyr
1               5                   10

<210> SEQ ID NO 31
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ala Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Asp His
                85                  90                  95

Val Val Phe Gly Gly Gly Thr Lys Leu Thr Val Leu Gly
                100                 105

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ala Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Asp His
                85                  90                  95

Val Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly

```
                145                 150                 155                 160
Val Glu Thr Thr Thr Pro Ser Lys Gln Ser Asn Asn Lys Tyr Ala Ala
                    165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
        210

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Asn Asn Ile Gly Lys Lys Asn Val Tyr
1               5                   10

<210> SEQ ID NO 34
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Lys Lys Asn Val
                20                  25                  30

Tyr Trp Tyr Gln Gln Lys Pro Gly Gln Ala Pro Val Leu Val Val His
                35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly
                100                 105

<210> SEQ ID NO 35
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Lys Lys Asn Val
                20                  25                  30

Tyr Trp Tyr Gln Gln Lys Pro Gly Gln Ala Pro Val Leu Val Val His
                35                  40                  45
```

```
Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Val Gly
 65                  70                  75                  80

Asp Glu Ala Asp Tyr Ser Cys Gln Val Trp Asp Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Asn Asn Ile Gly Ser Lys His Val Tyr
1               5                   10

<210> SEQ ID NO 37
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys His Val
            20                  25                  30

Tyr Trp Tyr Gln Gln Lys Pro Gly Gln Ala Pro Val Leu Val Val His
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Val Gly
 65                  70                  75                  80

Asp Glu Ala Asp Tyr Ser Cys Gln Val Trp Asp Ser Ser Asp His
                85                  90                  95

Val Val Phe Gly Gly Gly Thr Lys Leu Thr Val Leu Gly
            100                 105
```

```
<210> SEQ ID NO 38
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys His Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Asn Asn Ile Gly Ser Lys Asn Ala Tyr
1               5                   10

<210> SEQ ID NO 40
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Ala
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly
                100                 105
```

<210> SEQ ID NO 41
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Ala
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 42
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 42

Asp Asp Leu Asp Arg Pro Ser
1               5

<210> SEQ ID NO 43
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Leu Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 44
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Leu Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140
```

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Ser Ser Arg Pro Ser
1               5
```

```
<210> SEQ ID NO 46
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Ser Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Asp His
                85                  90                  95

Val Val Phe Gly Gly Gly Thr Lys Leu Thr Val Leu Gly
            100                 105
```

```
<210> SEQ ID NO 47
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
```

```
                35                  40                  45
Asp Asp Ser Ser Arg Pro Ser Gly Ile Pro Glu Arg Phe Ser Gly Ser
 50                  55                  60
Asn Ser Gly Asn Thr Ala Thr Leu Thr Ile Ser Arg Val Glu Val Gly
 65                  70                  75                  80
Asp Glu Ala Asp Tyr Ser Cys Gln Val Trp Asp Ser Ser Ser Asp His
                 85                  90                  95
Val Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser
    210

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Val Trp Leu Ser Ser Ser Asp His Val Val
1               5                   10

<210> SEQ ID NO 49
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Asn Val
             20                  25                  30
Tyr Trp Tyr Gln Gln Lys Pro Gly Gln Ala Pro Val Leu Val Val His
         35                  40                  45
Asp Asp Ser Asp Arg Pro Ser Gly Ile Pro Glu Arg Phe Ser Gly Ser
 50                  55                  60
Asn Ser Gly Asn Thr Ala Thr Leu Thr Ile Ser Arg Val Glu Val Gly
 65                  70                  75                  80
Asp Glu Ala Asp Tyr Ser Cys Gln Val Trp Leu Ser Ser Ser Asp His
                 85                  90                  95
Val Val Phe Gly Gly Gly Thr Lys Leu Thr Val Leu Gly
            100                 105
```

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Leu Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Val Trp Asp Ser Ser Ser Asp Ser Val Val
1               5                   10

<210> SEQ ID NO 52
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp Ser
                85                  90                  95

Val Val Phe Gly Gly Gly Thr Lys Leu Thr Val Leu Gly
            100                 105
```

<210> SEQ ID NO 53
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp Ser
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 54
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 54

Gln Val Trp Asp Ser Ser Ser Asp Tyr Val Val
1               5                   10

<210> SEQ ID NO 55
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp Tyr
                85                  90                  95

Val Val Phe Gly Gly Gly Thr Lys Leu Thr Val Leu Gly
            100                 105

<210> SEQ ID NO 56
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp Tyr
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140
```

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Val Trp Asp Ser Ser Ser Asp Val Val
1               5                   10

<210> SEQ ID NO 58
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp Asp
                85                  90                  95

Val Val Phe Gly Gly Gly Thr Lys Leu Thr Val Leu Gly
            100                 105

<210> SEQ ID NO 59
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30
```

Tyr Trp Tyr Gln Gln Lys Pro Gly Gln Ala Pro Val Leu Val Val His
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Val Gly
 65                  70                  75                  80

Asp Glu Ala Asp Tyr Ser Cys Gln Val Trp Asp Ser Ser Asp Asp
             85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Val Trp Asp Ser Ser Ser Asp His Val Ala
1               5                   10

<210> SEQ ID NO 61
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Val Gly
 65                  70                  75                  80

Asp Glu Ala Asp Tyr Ser Cys Gln Val Trp Asp Ser Ser Ser Asp His
                85                  90                  95

```
Val Ala Phe Gly Gly Gly Thr Lys Leu Thr Val Leu Gly
            100                 105
```

<210> SEQ ID NO 62
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Ala Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Gln Val Trp Asp Ser Ser Ser Asp His Val Trp
1               5                   10
```

<210> SEQ ID NO 64
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Trp Phe Gly Gly Gly Thr Lys Leu Thr Val Leu Gly
            100                 105

<210> SEQ ID NO 65
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Trp Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 66
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Asn Asn Ile Asp Ser Lys Asn Val Tyr
1               5                   10

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Asp Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 68
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Asp Ser Lys Asn Val
            20                  25                  30

Tyr Trp Tyr Gln Gln Lys Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
```

```
                130                 135                 140
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
    210

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgcagc tgcaggaatc tggccctggc ctggtcaagc ccagccagac cctgagcctg      60
acctgtaccg tgtccggcgg cagcatcagc aacgcggct actactggtc ctggatcaga     120
cagcaccccg gcaagggcct ggaatggatc ggctacatct actacagcgg cagcacctac     180
tacaacccca gcctgaagtc cagagtgacc atcagcgtgg acaccagcaa gaaccagttc     240
agcctgaagc tgagcagcgt gacagccgcc gacaccgccg tgtactactg cgccagcctg     300
ggcaattggt tcgactactg gggccagggc accctcgtga cagtgtcctc a              351

<210> SEQ ID NO 70
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gctagcacca agggcccag cgtgttcccc ctggccccctt gtagcagaag caccagcgag      60
agcacagccg ccctgggctg cctggtgaaa gactacttcc ccgagcccgt caccgtgtcc     120
tggaacagcg gagccctgac cagcggcgtg cacacctttc cagccgtgct gcagagcagc     180
ggcctgtaca gcctgagcag cgtggtgaca gtgccctcca gcagcctggg caccaagacc     240
tacacctgta acgtggacca caagcccagc aacaccaagg tggacaagcg ggtggaatct     300
aagtacggcc cacccctgccc ccctgccct gccctgaat ttctgggcgg accctccgtg     360
ttcctgttcc cccaaagcc caaggacacc ctgtatatca ctcgggagcc cgaagtgacc     420
tgcgtggtgg tggacgtgtc ccaggaagat cccgaggtcc agttcaattg gtacgtggac     480
ggcgtggaag tgcacaacgc caagaccaag cccagagagg aacagttcaa cagcacctac     540
cgggtggtgt ccgtgctgac cgtgctgcac caggactggc tgaacggcaa agagtacaag     600
tgcaaagtct ccaacaaggg cctgcccagc tccatcgaga aaaccatcag caaggccaag     660
ggccagcccc gcgagcctca ggtgtacaca ctgccccca gccaggaaga gatgaccaag     720
aaccaggtgt ccctgacctg tctggtgaaa ggcttctacc ccagcgatat cgccgtggaa     780
tgggagagca acggccagcc cgagaacaac tacaagacca cccccctgt gctggacagc     840
```

```
gacggcagct tcttcctgta ctcccggctg accgtggaca agagccggtg gcaggaaggc    900
aacgtcttca gctgcagcgt gatgcacgag gccctgcaca accactacac ccagaagtcc    960
ctgagcctga gcctgggc                                                  978
```

```
<210> SEQ ID NO 71
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
agctacgtgc tgacccagcc tcctagcgtg tccgtggccc ctggccagac cgccagaatc    60
acctgtggcg gcaacaacat cggcagcaag aacgtgtact ggtatcagca gaagcccggc   120 caggccccg tgctggtggt gcacgacgac agcgacagac ccagcggcat ccccgagcgg    180
ttcagcggca gcaacagcgg caataccgcc accctgacca tcagccgggt ggaagtgggc   240
gacgaggccg actacagctg ccaggtctgg gacagcagca gcgaccacgt ggtgttcggc   300
ggaggcacca agctgaccgt cctaggt                                       327
```

```
<210> SEQ ID NO 72
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cagcccaagg ccgctcccag cgtgaccctg ttcccccaa gcagcgagga actgcaggcc     60
aacaaggcca ccctggtgtg cctgatcagc gacttctacc ctggggccgt gaccgtggcc   120
tggaaggccg atagcagccc tgtgaaggcc ggcgtggaaa ccaccacccc ctccaagcag   180
agcaacaaca aatacgccgc cagcagctac ctgtccctga ccccgagca gtggaagtcc    240 caccggtcct acagctgcca ggtgacacac gagggcagca ccgtggaaaa gaccgtggcc   300
cccaccgagt gcagc                                                    315
```

```
<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Gly, Ala, Ser, Leu, Tyr, Asp, Gln, Lys, His or
      Trp
<220> FEATURE:
<221> NAME/KEY: MOD_RES
<222> LOCATION: (27)..(27)
<223> OTHER INFORMATION: Gly, Ala, Ser, Leu, Tyr, Asp, Gln, Lys, His or
      Trp
<220> FEATURE:
<221> NAME/KEY: MOD_RES
<222> LOCATION: (28)..(28)
<223> OTHER INFORMATION: Ser, Ala, Leu, Tyr, Asp, Gln, Lys, His or Trp
<220> FEATURE:
<221> NAME/KEY: MOD_RES
<222> LOCATION: (29)..(29)
<223> OTHER INFORMATION: Ile, Ala, Ser, Leu, Tyr, Asp, Gln, Lys, His or
      Trp
```

```
<220> FEATURE:
<221> NAME/KEY: MOD_RES
<222> LOCATION: (30)..(30)
<223> OTHER INFORMATION: Ser, Ala, Leu, Tyr, Asp, Gln, Lys, His or Trp
<220> FEATURE:
<221> NAME/KEY: MOD_RES
<222> LOCATION: (31)..(31)
<223> OTHER INFORMATION: Asn, Ala, Ser, Leu, Tyr, Asp, Gln, Lys, His or
     Trp
<220> FEATURE:
<221> NAME/KEY: MOD_RES
<222> LOCATION: (32)..(32)
<223> OTHER INFORMATION: Gly, Ala, Ser, Leu, Tyr, Asp, Gln, Lys, His or
     Trp
<220> FEATURE:
<221> NAME/KEY: MOD_RES
<222> LOCATION: (33)..(33)
<223> OTHER INFORMATION: Gly, Ala, Ser, Leu, Tyr, Asp, Gln, Lys, His or
     Trp
<220> FEATURE:
<221> NAME/KEY: MOD_RES
<222> LOCATION: (34)..(34)
<223> OTHER INFORMATION: Tyr, Ala, Ser, Leu, Asp, Gln, Lys, His or Trp
<220> FEATURE:
<221> NAME/KEY: MOD_RES
<222> LOCATION: (35)..(35)
<223> OTHER INFORMATION: Tyr, Ala, Ser, Leu, Asp, Gln, Lys, His or Trp
<220> FEATURE:
<221> NAME/KEY: MOD_RES
<222> LOCATION: (36)..(36)
<223> OTHER INFORMATION: Trp, Ala, Ser, Leu, Tyr, Asp, Gln, Lys or His
<220> FEATURE:
<221> NAME/KEY: MOD_RES
<222> LOCATION: (37)..(37)
<223> OTHER INFORMATION: Ser, Ala, Leu, Tyr, Asp, Gln, Lys, His or Trp
<220> FEATURE:
<221> NAME/KEY: MOD_RES
<222> LOCATION: (52)..(52)
<223> OTHER INFORMATION: Tyr, Ala, Ser, Leu, Asp, Gln, Lys, His or Trp
<220> FEATURE:
<221> NAME/KEY: MOD_RES
<222> LOCATION: (53)..(53)
<223> OTHER INFORMATION: Ile, Ala, Ser, Leu, Tyr, Asp, Gln, Lys, His or
     Trp
<220> FEATURE:
<221> NAME/KEY: MOD_RES
<222> LOCATION: (54)..(54)
<223> OTHER INFORMATION: Tyr, Ala, Ser, Leu, Asp, Gln, Lys, His or Trp
<220> FEATURE:
<221> NAME/KEY: MOD_RES
<222> LOCATION: (55)..(55)
<223> OTHER INFORMATION: Tyr, Ala, Ser, Leu, Asp, Gln, Lys, His or Trp
<220> FEATURE:
<221> NAME/KEY: MOD_RES
<222> LOCATION: (56)..(56)
<223> OTHER INFORMATION: Ser, Ala, Leu, Asp, Gln, Lys, His or Trp
<220> FEATURE:
<221> NAME/KEY: MOD_RES
<222> LOCATION: (57)..(57)
<223> OTHER INFORMATION: Gly, Ala, Ser, Leu, Tyr, Asp, Gln, Lys, His or
     Trp
<220> FEATURE:
<221> NAME/KEY: MOD_RES
<222> LOCATION: (58)..(58)
<223> OTHER INFORMATION: Ser, Ala, Leu, Tyr, Asp, Gln, Lys, His or Trp
<220> FEATURE:
<221> NAME/KEY: MOD_RES
<222> LOCATION: (59)..(59)
<223> OTHER INFORMATION: Thr, Ala, Ser, Leu, Tyr, Asp, Gln, Lys, His or
     Trp
<220> FEATURE:
<221> NAME/KEY: MOD_RES
<222> LOCATION: (60)..(60)
<223> OTHER INFORMATION: Tyr, Ala, Ser, Leu, Asp, Gln, Lys, His or Trp
<220> FEATURE:
<221> NAME/KEY: MOD_RES
<222> LOCATION: (98)..(98)
<223> OTHER INFORMATION: Ala, Ser, Leu, Tyr, Asp, Gln, Lys, His, Trp or
     Pro
```

```
<220> FEATURE:
<221> NAME/KEY: MOD_RES
<222> LOCATION: (99)..(99)
<223> OTHER INFORMATION: Ser, Ala, Leu, Tyr, Asp, Gln, Lys, His, Trp or
      Pro
<220> FEATURE:
<221> NAME/KEY: MOD_RES
<222> LOCATION: (100)..(100)
<223> OTHER INFORMATION: Leu, Ala, Ser, Tyr, Asp, Gln, Lys, His, Trp or
      Pro
<220> FEATURE:
<221> NAME/KEY: MOD_RES
<222> LOCATION: (101)..(101)
<223> OTHER INFORMATION: Gly, Ala, Ser, Leu, Tyr, Asp, Gln, Lys, His,
      Trp or Pro
<220> FEATURE:
<221> NAME/KEY: MOD_RES
<222> LOCATION: (102)..(102)
<223> OTHER INFORMATION: Asn, Ala, Ser, Leu, Tyr, Asp, Gln, Lys, His,
      Trp or Pro
<220> FEATURE:
<221> NAME/KEY: MOD_RES
<222> LOCATION: (103)..(103)
<223> OTHER INFORMATION: Trp, Ala, Ser, Leu, Tyr, Asp, Gln, Lys, His or
      Pro
<220> FEATURE:
<221> NAME/KEY: MOD_RES
<222> LOCATION: (104)..(104)
<223> OTHER INFORMATION: Phe, Ala, Ser, Leu, Tyr, Asp, Gln, Lys, His,
      Trp or Pro
<220> FEATURE:
<221> NAME/KEY: MOD_RES
<222> LOCATION: (105)..(105)
<223> OTHER INFORMATION: Asp, Ala, Ser, Leu, Tyr, Gln, Lys, His, Trp or
      Pro
<220> FEATURE:
<221> NAME/KEY: MOD_RES
<222> LOCATION: (106)..(106)
<223> OTHER INFORMATION: Tyr, Ala, Ser, Leu, Asp, Gln, Lys, His, Trp or
      Pro

<400> SEQUENCE: 73

Gln Val Gln Leu Gln Glu Ser Gly Pro Gly Leu Val Lys Pro Ser Gln
1               5                   10                  15

Thr Leu Ser Leu Thr Cys Thr Val Ser Xaa Xaa Xaa Xaa Xaa Xaa
            20                  25                  30

Xaa Xaa Xaa Xaa Xaa Trp Ile Arg Gln His Pro Gly Lys Gly Leu Glu
        35                  40                  45

Trp Ile Gly Xaa Xaa Xaa Xaa Xaa Xaa Xaa Xaa Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Xaa Xaa Xaa Xaa Xaa Xaa Xaa Xaa Trp Gly Gln Gly Thr Leu
            100                 105                 110

Val Thr Val Ser Ser
        115

<210> SEQ ID NO 74
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Gly, Ala, Ser, Leu, Tyr, Asp, Gln, Lys, His or
```

```
        Trp
<220> FEATURE:
<221> NAME/KEY: MOD_RES
<222> LOCATION: (24)..(24)
<223> OTHER INFORMATION: Gly, Ala, Ser, Leu, Tyr, Asp, Gln, Lys, His or
      Trp
<220> FEATURE:
<221> NAME/KEY: MOD_RES
<222> LOCATION: (25)..(25)
<223> OTHER INFORMATION: Asn, Ala, Ser, Leu, Tyr, Asp, Gln, Lys, His or
      Trp
<220> FEATURE:
<221> NAME/KEY: MOD_RES
<222> LOCATION: (26)..(26)
<223> OTHER INFORMATION: Asn, Ala, Ser, Leu, Tyr, Asp, Gln, Lys, His or
      Trp
<220> FEATURE:
<221> NAME/KEY: MOD_RES
<222> LOCATION: (27)..(27)
<223> OTHER INFORMATION: Ile, Ala, Ser, Leu, Tyr, Asp, Gln, Lys, His or
      Trp
<220> FEATURE:
<221> NAME/KEY: MOD_RES
<222> LOCATION: (28)..(28)
<223> OTHER INFORMATION: Gly, Ala, Ser, Leu, Tyr, Asp, Gln, Lys, His or
      Trp
<220> FEATURE:
<221> NAME/KEY: MOD_RES
<222> LOCATION: (29)..(29)
<223> OTHER INFORMATION: Ser, Ala, Leu, Tyr, Asp, Gln, Lys, His or Trp
<220> FEATURE:
<221> NAME/KEY: MOD_RES
<222> LOCATION: (30)..(30)
<223> OTHER INFORMATION: Lys, Ala, Ser, Leu, Tyr, Asp, Gln, His or Trp
<220> FEATURE:
<221> NAME/KEY: MOD_RES
<222> LOCATION: (31)..(31)
<223> OTHER INFORMATION: Asn, Ala, Ser, Leu, Tyr, Asp, Gln, Lys, His or
      Trp
<220> FEATURE:
<221> NAME/KEY: MOD_RES
<222> LOCATION: (32)..(32)
<223> OTHER INFORMATION: Val, Ala, Ser, Leu, Tyr, Asp, Gln, Lys, His or
      Trp
<220> FEATURE:
<221> NAME/KEY: MOD_RES
<222> LOCATION: (33)..(33)
<223> OTHER INFORMATION: Tyr, Ala, Ser, Leu, Asp, Gln, Lys, His or Trp
<220> FEATURE:
<221> NAME/KEY: MOD_RES
<222> LOCATION: (49)..(49)
<223> OTHER INFORMATION: Asp, Ala, Ser, Leu, Tyr, Gln, Lys, His or Trp
<220> FEATURE:
<221> NAME/KEY: MOD_RES
<222> LOCATION: (50)..(50)
<223> OTHER INFORMATION: Asp, Ala, Ser, Leu, Tyr, Gln, Lys, His or Trp
<220> FEATURE:
<221> NAME/KEY: MOD_RES
<222> LOCATION: (51)..(51)
<223> OTHER INFORMATION: Ser, Ala, Leu, Tyr, Asp, Gln, Lys, His or Trp
<220> FEATURE:
<221> NAME/KEY: MOD_RES
<222> LOCATION: (52)..(52)
<223> OTHER INFORMATION: Asp, Ala, Ser, Leu, Tyr, Gln, Lys, His or Trp
<220> FEATURE:
<221> NAME/KEY: MOD_RES
<222> LOCATION: (53)..(53)
<223> OTHER INFORMATION: Arg, Ala, Ser, Leu, Tyr, Asp, Gln, Lys, His or
      Trp
<220> FEATURE:
<221> NAME/KEY: MOD_RES
<222> LOCATION: (54)..(54)
<223> OTHER INFORMATION: Pro, Ala, Ser, Leu, Tyr, Asp, Gln, Lys, His or
      Trp
<220> FEATURE:
<221> NAME/KEY: MOD_RES
<222> LOCATION: (55)..(55)
<223> OTHER INFORMATION: Ser, Ala, Leu, Tyr, Asp, Gln, Lys, His or Trp
<220> FEATURE:
```

```
<221> NAME/KEY: MOD_RES
<222> LOCATION: (88)..(88)
<223> OTHER INFORMATION: Gln, Ala, Ser, Leu, Tyr, Asp, Lys, His, Trp or
      Pro
<220> FEATURE:
<221> NAME/KEY: MOD_RES
<222> LOCATION: (89)..(89)
<223> OTHER INFORMATION: Val, Ala, Ser, Leu, Tyr, Asp, Gln, Lys, His,
      Trp or Pro
<220> FEATURE:
<221> NAME/KEY: MOD_RES
<222> LOCATION: (90)..(90)
<223> OTHER INFORMATION: Trp, Ala, Ser, Leu, Tyr, Asp, Gln, Lys, His or
      Pro
<220> FEATURE:
<221> NAME/KEY: MOD_RES
<222> LOCATION: (91)..(91)
<223> OTHER INFORMATION: Asp, Ala, Ser, Leu, Tyr, Gln, Lys, His, Trp or
      Pro
<220> FEATURE:
<221> NAME/KEY: MOD_RES
<222> LOCATION: (92)..(92)
<223> OTHER INFORMATION: Ser, Ala, Leu, Tyr, Asp, Gln, Lys, His, Trp or
      Pro
<220> FEATURE:
<221> NAME/KEY: MOD_RES
<222> LOCATION: (93)..(93)
<223> OTHER INFORMATION: Ser, Ala, Leu, Tyr, Asp, Gln, Lys, His, Trp or
      Pro
<220> FEATURE:
<221> NAME/KEY: MOD_RES
<222> LOCATION: (94)..(94)
<223> OTHER INFORMATION: Ser, Ala, Leu, Tyr, Asp, Gln, Lys, His, Trp or
      Pro
<220> FEATURE:
<221> NAME/KEY: MOD_RES
<222> LOCATION: (95)..(95)
<223> OTHER INFORMATION: Asp, Ala, Ser, Leu, Tyr, Gln, Lys, His, Trp or
      Pro
<220> FEATURE:
<221> NAME/KEY: MOD_RES
<222> LOCATION: (96)..(96)
<223> OTHER INFORMATION: His, Ala, Ser, Leu, Tyr, Asp, Gln, Lys, Trp or
      Pro
<220> FEATURE:
<221> NAME/KEY: MOD_RES
<222> LOCATION: (97)..(97)
<223> OTHER INFORMATION: Val, Ala, Ser, Leu, Tyr, Asp, Gln, Lys, His,
      Trp or Pro
<220> FEATURE:
<221> NAME/KEY: MOD_RES
<222> LOCATION: (98)..(98)
<223> OTHER INFORMATION: Val, Ala, Ser, Leu, Tyr, Asp, Gln, Lys, His,
      Trp or Pro

<400> SEQUENCE: 74

Ser Tyr Val Leu Thr Gln Pro Pro Ser Val Ser Val Ala Pro Gly Gln
1               5                   10                  15

Thr Ala Arg Ile Thr Cys Xaa Xaa Xaa Xaa Xaa Xaa Xaa Xaa Xaa
            20                  25                  30

Xaa Trp Tyr Gln Gln Lys Pro Gly Gln Ala Pro Val Leu Val Val His
35                  40                  45

Xaa Xaa Xaa Xaa Xaa Xaa Xaa Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80

Asp Glu Ala Asp Tyr Ser Cys Xaa Xaa Xaa Xaa Xaa Xaa Xaa Xaa
                85                  90                  95

Xaa Xaa Phe Gly Gly Gly Thr Lys Leu Thr Val Leu Gly
        100                 105
```

-continued

```
<210> SEQ ID NO 75
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Gly or Lys
<220> FEATURE:
<221> NAME/KEY: MOD_RES
<222> LOCATION: (25)..(25)
<223> OTHER INFORMATION: Asn or Asp
<220> FEATURE:
<221> NAME/KEY: MOD_RES
<222> LOCATION: (26)..(26)
<223> OTHER INFORMATION: Asn or His
<220> FEATURE:
<221> NAME/KEY: MOD_RES
<222> LOCATION: (27)..(27)
<223> OTHER INFORMATION: Ile or Ala
<220> FEATURE:
<221> NAME/KEY: MOD_RES
<222> LOCATION: (28)..(28)
<223> OTHER INFORMATION: Gly or Asp
<220> FEATURE:
<221> NAME/KEY: MOD_RES
<222> LOCATION: (29)..(29)
<223> OTHER INFORMATION: Ser or Lys
<220> FEATURE:
<221> NAME/KEY: MOD_RES
<222> LOCATION: (31)..(31)
<223> OTHER INFORMATION: Asn or His
<220> FEATURE:
<221> NAME/KEY: MOD_RES
<222> LOCATION: (32)..(32)
<223> OTHER INFORMATION: Val or Ala
<220> FEATURE:
<221> NAME/KEY: MOD_RES
<222> LOCATION: (51)..(51)
<223> OTHER INFORMATION: Ser or Leu
<220> FEATURE:
<221> NAME/KEY: MOD_RES
<222> LOCATION: (52)..(52)
<223> OTHER INFORMATION: Asp or Ser
<220> FEATURE:
<221> NAME/KEY: MOD_RES
<222> LOCATION: (91)..(91)
<223> OTHER INFORMATION: Asp or Leu
<220> FEATURE:
<221> NAME/KEY: MOD_RES
<222> LOCATION: (96)..(96)
<223> OTHER INFORMATION: His, Ser, Tyr or Asp
<220> FEATURE:
<221> NAME/KEY: MOD_RES
<222> LOCATION: (98)..(98)
<223> OTHER INFORMATION: Val, Ala or Trp

<400> SEQUENCE: 75

Ser Tyr Val Leu Thr Gln Pro Pro Ser Val Ser Val Ala Pro Gly Gln
1               5                   10                  15

Thr Ala Arg Ile Thr Cys Gly Xaa Xaa Xaa Xaa Xaa Lys Xaa Xaa
            20                  25                  30

Tyr Trp Tyr Gln Gln Lys Pro Gly Gln Ala Pro Val Leu Val Val His
        35                  40                  45

Asp Asp Xaa Xaa Arg Pro Ser Gly Ile Pro Glu Arg Phe Ser Gly Ser
    50                  55                  60

Asn Ser Gly Asn Thr Ala Thr Leu Thr Ile Ser Arg Val Glu Val Gly
65                  70                  75                  80
```

```
Asp Glu Ala Asp Tyr Ser Cys Gln Val Trp Xaa Ser Ser Ser Asp Xaa
                    85                  90                  95
Val Xaa Phe Gly Gly Gly Thr Lys Leu Thr Val Leu Gly
        100                 105
```